United States Patent
Esnault et al.

(10) Patent No.: US 7,109,182 B2
(45) Date of Patent: Sep. 19, 2006

(54) SYNTHETIC OLIGOMANNOSIDES, PREPARATION AND USES THEREOF

(75) Inventors: Jacques Esnault, Orléans (FR); Pierre Sinay, Paris (FR); Reynald Chevalier, Toronto (CA); Jean-Frédéric Colombel, La Madeleine (FR); Jean-Maurice Mallet, Le Kremlin-Bicêtre (FR); Boualem Sendid, Loos (FR); Thierry Jouault, Villeneuve d'Ascq (FR); Daniel Poulain, Templeuve (FR); Pierre-André Trinel, Villeneuve d'Ascq (FR)

(73) Assignee: Centre Hospitalier Regional Universitaire (CHRU), (FR)

( * ) Notice: Subject to any disclaimer, the term of this patent is extended or adjusted under 35 U.S.C. 154(b) by 0 days.

(21) Appl. No.: 10/153,936

(22) Filed: May 23, 2002

(65) Prior Publication Data

US 2003/0105060 A1    Jun. 5, 2003

Related U.S. Application Data

(63) Continuation of application No. PCT/FR00/03265, filed on Nov. 23, 2000.

(30) Foreign Application Priority Data

Nov. 23, 1999 (FR) ................................... 99 14747

(51) Int. Cl.
A61K 31/715 (2006.01)
(52) U.S. Cl. .............................. 514/61; 514/2; 514/54; 514/25; 536/4.1; 536/18.5; 536/18.6; 536/123.1; 536/12.4; 435/69.1; 435/320.1; 435/252.1; 435/254.1

(58) Field of Classification Search ................ 536/4.1, 536/18.5, 18.6, 123.1, 124; 514/25, 54, 61, 514/2; 435/69.1, 320.1, 252.1, 254.1
See application file for complete search history.

(56) References Cited

U.S. PATENT DOCUMENTS 4,749,566 A * 6/1988 Casellas et al. .......... 424/182.1
4,939,123 A * 7/1990 Neeser et al. .................. 514/8

FOREIGN PATENT DOCUMENTS

| JP | 57 054199 A | 3/1982 |
| JP | 57 072996 A | 5/1982 |
| JP | 57 072997 A | 5/1982 |
| JP | 59 036690 A | 2/1984 |
| JP | 59 036691 A | 2/1984 |
| JP | 60 045587 A | 3/1985 |
| JP | 60 045588 A | 3/1985 |
| JP | 60 045589 A | 3/1985 |

OTHER PUBLICATIONS

Suzuki et al. "Immunichemical study on mammans of genus candida I. Structural investigation of antigenic factors 1,4,5,6,8,9,11,13,13b and 34." Current Topics in Medical Mycology, vol. 8,No. 1-2,pp. 57-70, 1997.*

(Continued)

*Primary Examiner*—Shaojia Anna Jiang
*Assistant Examiner*—Devesh Khare
(74) *Attorney, Agent, or Firm*—DLA Piper Rudnick Gray Cary US LLP

(57) ABSTRACT

A pharmaceutical composition including a therapeutically effective amount of at least one oligomannoside produced by chemical synthesis which is homologous to a wall oligomannoside of an infectious organism or pathogen, or a derivative thereof, and a pharmaceutically acceptable vehicle.

12 Claims, 10 Drawing Sheets

OTHER PUBLICATIONS

Han et al. "a vaccine and monoclonal antibodies that enhance mouse resistance to Candida albicans vaginal infection." Infection and Immunity, vol. 66, No. 12, pp. 5771-5776, Dec. 1998.*

Hideya Yuasa et al., *Synthesis of 5-Thiomannose-Containing Oligomannoside Mimics: Binding Abilities to Concanavalin A*, Bioorganic & Medicinal Chemistry Letters, vol. 8, No. 11, Jun. 2, 1998, pp. 1297-1300.

Osamu Tsuruta et al., *Syntheses of Two Trimannose Analogs Each Containing C-Mannosyl or 5-Thio-C-Mannosyl Residue: Their Affinities to Concanavalin A*, Bioorganic & Medicinal Chemistry Letters, vol. 9, No. 6, Mar. 22, 1999, pp. 807-810.

Hideya Yuasa et al., *Solid Phase Synthesis of Oligomannopeptoids That Mimic the concanavaline A-Binding Trimannoside*, Bioorganic & Medicinal Chemistry Letters, vol. 8, No. 16, Aug. 18, 1998, pp. 2139-2144.

Pierre-André Trinel et al., *Mapping of Candida albicans Oligomannosidic Epitopes by Using Monoclonal Antibodies*, Infection and Immunity, vol. 60, No. 9, Sep. 1992, pp. 3845-3851.

Yongmoon Han et al., *A Vaccine and Monoclonal Antibodies That Enhance Mouse Resistance to Candida albicans Vaginal Infection*, Infection and Immunity, vol. 66, No. 12, Dec. 1998, pp. 5771-5776.

Mia Young et al., *Characterization of Oligosaccharides From an Antigenic Mannan of Saccharomyces cerevisiae*, Glyocconjugate Journal, vol. 15, 1998, pp. 815-822.

Mason X. Zhang et al., *Contrasting Roles of Mannan-Specific Monoclonal Immunoglobulin M Antibodies in the Activation of Classical and Alternative Pathways by Candida albicans*, Infection and Immunity, vol. 66, No. 12, Dec. 1998, pp. 6027-6029.

B. Sendid et al., *Specific Antibody Response to Oligomannosidic Epitopes in Crohn's Disease*, Clinical and Diagnostic Laboratory Immunology, vol. 3, No. 2, Mar. 1996, pp. 219-226.

Pierre Marie Jacquinot et al., *Nature of Candida albicans-Derived Carbohydrate Antigen Recognized by a Monoclonal Antibody in Patient Sera and Distribution Over Candida Species*, FEMS Microbiology Letters, vol. 169, Dec. 1, 1998, pp. 131-138.

Shigeo Suzuki, *Immunochemical Study on Mannans of Genus Candida. I. Structural Investigation of Antigenic Factors 1, 4, 5, 6, 8, 9, 11, 13, 13b and 34*, Current Topics in Medical Mycology, vol. 8, No. 1-2, 1997, pp. 57-70.

* cited by examiner

SYNTHETIC OLIGOMANNOSIDES, PREPARATION AND USES THEREOF

RELATED APPLICATION

This is a continuation of International Application No. PCT/FR00/03265, with an international filing date of Nov. 23, 2000, which is based on French Patent Application No. 99/14747, filed Nov. 23, 1999.

FIELD OF THE INVENTION

This invention relates to synthetic oligomannosides, their preparation and their use for detecting antibodies and preventing infections.

BACKGROUND

In the opportunistic yeast *Candida albicans*, as with all fungi, a considerable part of the metabolism is derived toward the synthesis of wall polysaccharides whose organization finely modulates the adaptation of the cell to the medium. Numerous research teams have established the preponderant importance of the mannans of *C. albicans* in the physiopathology of candidiasis. It has been demonstrated that the diverse interactions of mannans with the humoral and cellular components of the host are based on a specificity dependent on the oligomannosides sequences synthesized by the yeast. It is the bond anomery of the mannose residues and the length of the oligomannoside chain which determine the nature of the interaction which influences the outcome of the infection.

Research concerning the biological properties and the structure of these oligomannosides, as well as the development of diagnostic methods or preventive procedures for these infections, requires the availability of large amounts of oligomannosides. However, the production of natural oligomannosides from strains of *C. albicans* is complicated and expensive. It is, of course, necessary to have available such strains, to store them, and culture them in fermenters under very standardized conditions because the nature of the sugars is strictly dependent on the medium, temperature, oxygenation, culture time, etc. The fermenter culturing of *C. albicans* requires sophisticated expertise and numerous precautionary measures of a microbiological nature. The batches of mannans must then be recovered from the cultures and characterized by their antigenic and especially chemical properties. This requires depolymerization of the mannans and NMR analysis of the liberated sugars.

These natural oligomannosides are used to prepare immunological diagnostic tests of *C. albicans* infections. However, sensitization of the plates with the mannans antigen is performed with different production batches and according to a protocol which does not enable monitoring of the amount deposited. Thus, several tests use natural yeast mannans for the diagnosis of candidiasis (Sendid, B. et al., 1999, J. Clin. Microbiol. 37(5): 1510–7) and Crohn's disease (Sendid, B. et al., 1996, Clin. Diagn. Lab. Immunol. 3(2): 219: 26). These tests detect antibodies directed against the mixtures of oligomannoside sequences present in the mannans of *C. albicans* and *S. cerevisiae*.

SUMMARY OF THE INVENTION

This invention relates to a pharmaceutical composition including a therapeutically effective amount of at least one oligomannoside produced by chemical synthesis which is homologous to a wall oligomanoside of an infectious organism or pathogen, or a derivative thereof, and a pharmaceutically acceptable vehicle.

BRIEF DESCRIPTION OF THE DRAWINGS

Other advantages and characteristics of the invention will become apparent from the examples below concerning preparation of synthetic oligomannosides and their use for the diagnosis, prevention and treatment of infections, and in which reference will be made to the attached drawings in which.

DETAILED DESCRIPTION

Figure 1A:
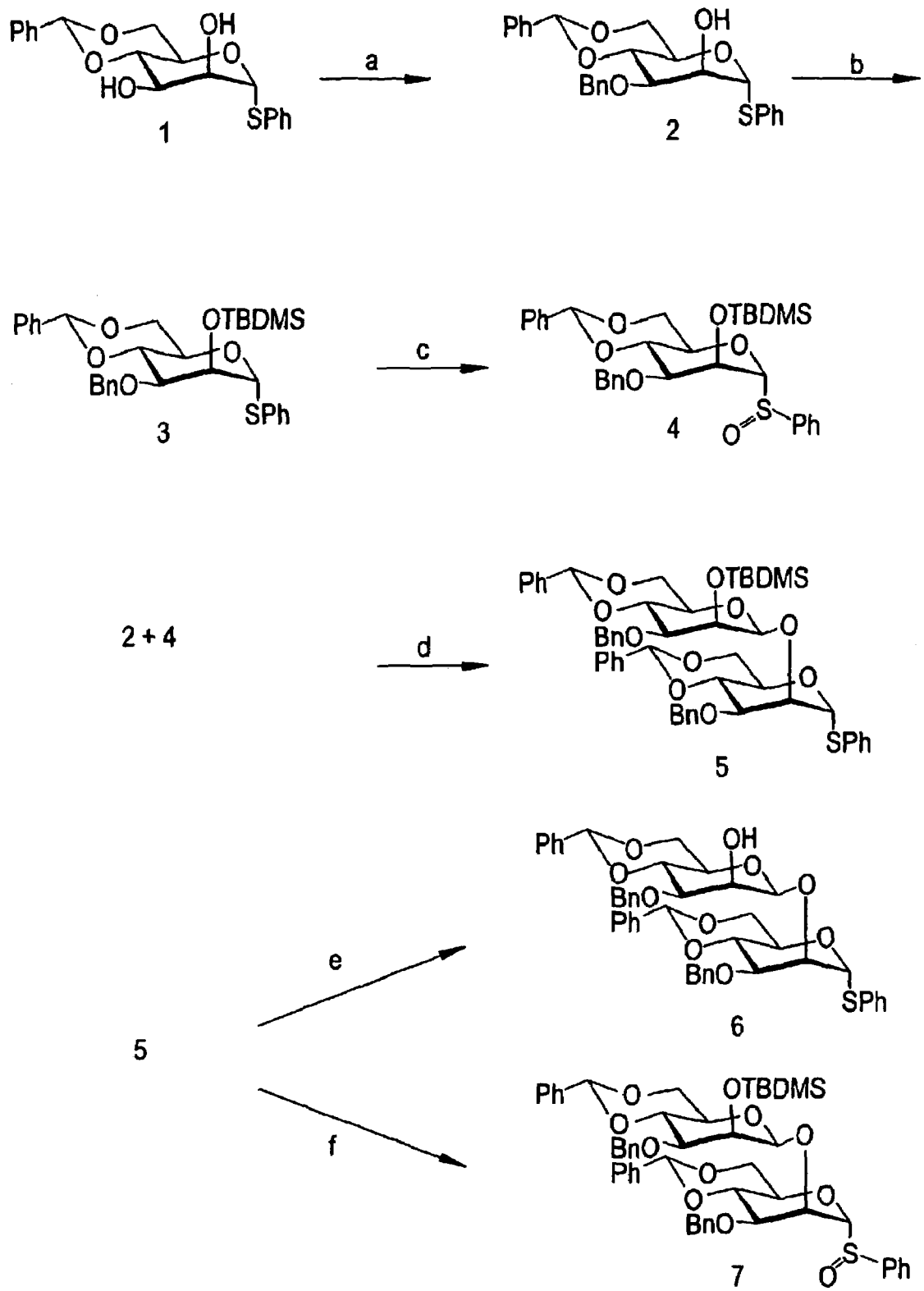
FIG. 1 is a reaction diagram for the preparation of D-Man β(1-2) D-Man β(1-2) D-Man β(1-2) D-Man of formula (I).

In order to resolve the drawbacks specified above, we have succeeded in producing by chemical synthesis in large quantities and in a reproducible manner analogues of the oligomannosides of the cellular envelopes of yeasts, referred to below as "synthetic oligomannosides", which can advantageously replace the natural mannans. The research studies performed with these synthetic oligomannosides have shown that they replicate the biological properties of the natural sugars of *C. albicans*, especially with regard to antigenicity, adherence to mammal cells and molecules, and cellular stimulation. We have found that synthetic oligomannosides can be used successfully for sensitizing microtitration plates by covalent coupling for the detection of specific antibodies of each structure whose diagnostic and prognostic significance is different (Jouault, T., 1997, Clin. Diagn. Lab. Immunol. 4(3): 328–33).

Furthermore, we found that these synthetic oligomannosides exhibited remarkable properties of inhibiting colonization by *C. albicans* such that they can be used for the prevention and treatment of candidiasis.

Thus, the invention relates to an oligomannoside produced by chemical synthesis which is homologous to a wall oligomannoside of an infectious organism or pathogen. More particularly, the organism is a yeast, a fungus, a virus or a *bacterium* whose cellular envelope contains oligomannosides. The term "cellular envelope" is understood to mean the cellular membrane, wall or capsule. The invention concerns more particularly the yeasts, and specifically *Candida albicans* or *Saccharomyces cerevisiae*.

The term "homologous" is understood to mean the fact that the synthetic oligomannosides of the invention have the same mannose motifs according to the same α or β bond linking, (1-2), (1-3), (1-6), as the natural oligomannosides of yeasts, especially *Candida albicans* or *Saccharomyces cerevisiae*, but are devoid of the other cellular components, notably proteins, sugars and lipids which are inevitably associated with the natural oligomannosides described in the prior art.

The term "synthetic oligomannoside derivative of the invention" is understood to mean an oligomannoside in which one or more functional groups are substituted, for example, by a protector group or synthetic oligomannosides groups conjugated with a binding group, also referred to as a "connector" for attachment to a support such as a microtitration plate.

The invention pertains more particularly to synthetic oligomannosides responding to the following general formula:

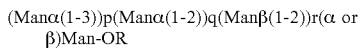

in which:

R represents a hydrogen atom, a $C_1$ to $C_{20}$ alkyl, preferably a $C_{15}$ to $C_{20}$ alkyl, a connector group, optionally labeled, for example, by a chromophoric or fluorescent group, or by a substance capable of making the synthetic oligomannosides immunogenic such as will be described below, p, q and r are whole numbers between 0 and 19, preferably between 0 and 11, and the sum p+q+r is between 1 and 19, preferably between 1 and 11, the three parts of the polymer (Manα(1-3))p(Manα(1-2))q(Manβ(1-2))r can be inverted or repeated.

Among the synthetic oligomannosides described above, the invention pertains more particularly to the tetramannosides, and most specifically to the following synthetic tetramannosides:

D-Man β(1-2) D-Man β(1-2) D-Man β(1-2) D-Man of *C. albicans*, also designated below as Mβ-1-2-tetramannosides, responding to formula (I) below:

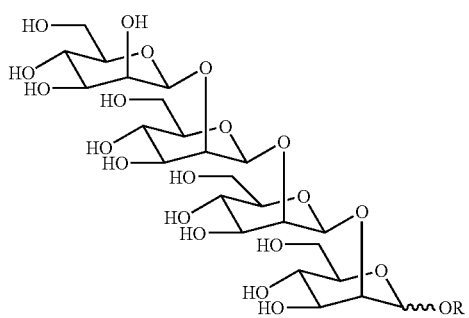

in which R represents a hydrogen atom, a $C_1$ to $C_{20}$ alkyl, preferably a $C_{15}$ to $C_{20}$ alkyl, or a connector group, optionally labeled, for example, by a chromophoric or fluorescent group or by a substance capable of making the synthetic oligomannosides immunogenic, or a derivative in which one or more of the hydroxyl groups are substituted.

D-Man α(1-2) D-Man α(1-2) D-Man α(1-2) D-Man of *C. albicans*, also designated below as Mα-1-2-tetramannosides, responding to formula (II) below:

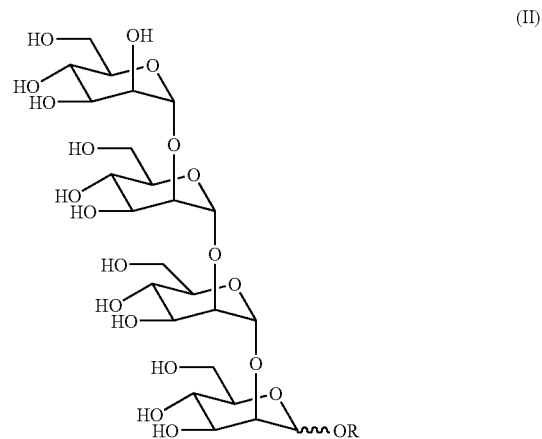

in which R has the same meaning as in formula (I).

D-Man α(1-3) D-Man α(1-2) D-Man α(1-2) D-Man α(1-2) of *S. cerevisiae*, responding to formula (III) below:

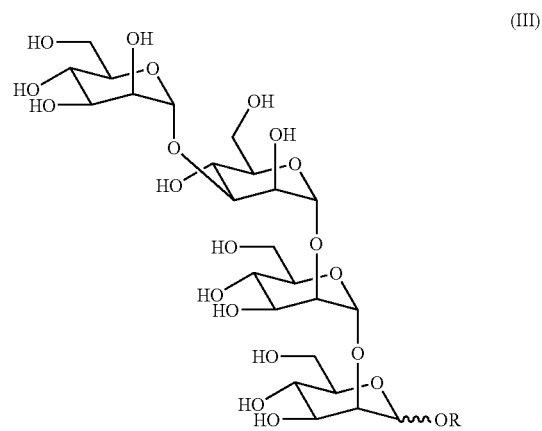

in which R has the same meaning as in formula (I).

The presence of an R group representing a connector is useful for preparing tests for the detection in a subject of specific antibodies of certain oligomannosides for diagnosis of a *C. albicans* infection or chronic inflammatory diseases of the intestine and, especially, of Crohn's disease as will be described below.

The connector can be any chemical group enabling coupling, preferably by covalence by also by other bonds, for example, of the hydrophobic type, of the synthetic oligomannosides onto a support such as a microtitration plate. Covalent coupling has the advantage of using a robust surface which is suitable for immunoanalytic tests. It allows better orientation of the synthetic oligomannosides, and provides a higher density of epitopes and avoids the problems of antibody recognition because the antigenic sites are very accessible.

Preference is given to connectors comprising a carboxylic acid functional group which can be activated for coupling onto a surface which is itself activated for reacting with the synthetic oligomannosides. An example of a connector is the connector of R. U. Lumieux (Lumieux, R. U. et al., 1975, J. Am. Chem. Soc. 97, 4076–4083) in which R represents a group of formula: —CH$_2$—(CH$_2$)$_7$—CO$_2$H.

Connectors bearing a carboxylic acid group, like the connector of R. U. Lemieux, can be activated by a carbodiimide to obtain an activated ester which enables formation of amide bonds with the primary amine groups on the surface of the support. The water-soluble carbodiimide (EDC: 1-ethyl-3-(3-dimethylaminopropyl)carbodiimide) is used to activate the —COOH groups of synthetic oligomannosides in the presence of sulfo-N-hydroxy succinimide (sulfo-NHS: N-hydroxysuccinimidine). Sulfo-NHS effectively suppresses hydrolysis of the activated product and enables attachment of the synthetic oligomannoside to the surface of the plate that has already been sensitized by the —NH$_2$ group.

The synthetic oligomannosides of the invention can be prepared by condensation of protected monosaccharides or disaccharides, preferably by condensation of protected dimannosides according to a diblock strategy.

One preferred form of implementation of a diblock strategy for the preparation of oligomannosides according to the invention includes
a) preparing diblocks in which:
    at least one of the two blocks is the intermediary block in which the free hydroxyl functional groups of each monosaccharide are substituted by one or more, identical or different protector groups, except for the hydroxyl functional group necessary for the condensation with another diblock which is activated by a starting group,
    one of the two blocks is the terminal block in which the free hydroxyl functional groups of each monosaccharide are substituted by one or more, identical or different protector groups, except for the hydroxyl functional group necessary for the condensation with another diblock, and possibly the hydroxyl functional group substituted by a binding group for attachment of the oligomannoside on a support, and
b) condensing the diblocks, then deprotecting the oligomannoside prepared in this manner.

One example of Man α(1-2) Man dimannosides for implementation of the above process responds to formula (IV) below:

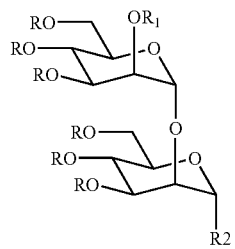

(IV)

in which:
    R is a permanent protector group. The term "permanent protector group" is understood to mean a protector group which is introduced at the beginning of synthesis and withdrawn at the end of the synthesis of the oligomannoside. A benzyl group can be cited as an example of a protector group of this type.
    R1 is a temporary protector group. The term "temporary protector group" is understood to mean a protector group which is removed to enable condensation. The acetate group can be cited as an example of a protector group of this type.
    R2 is:
        in the case of an intermediary block, a starting group and in this case the block can be associated with the rest of the polymer at α or β; —O—C(NH)—CCl$_3$ or PhS can be cited as an example of a starting group,
        in the case of a terminal block, a group selected from among an alkyl or benzyl group, or a connector at α or β.

One example of Man β(1-2) Man dimannosides for implementation of the above process responds to formula (V) below:

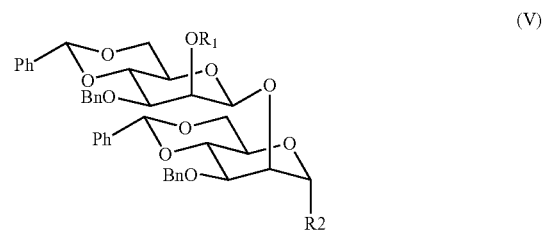

(V)

in which:
    R1 is a temporary protector group; a terbutyl dimethyl silyl group can be cited as an example of a such a temporary protector group.
    R2 is:
        in the case of an intermediary block, a starting group and in this case the block can be associated with the rest of the polymer at α or β; SPh or SOPh can be cited as an example of such a starting group,
        in the case of a terminal block, a group selected from among an alkyl or benzyl group, or a connector at α or β.

One example of Man α(1-3) Man dimannosides for implementation of the above process responds to formula (VI) below:

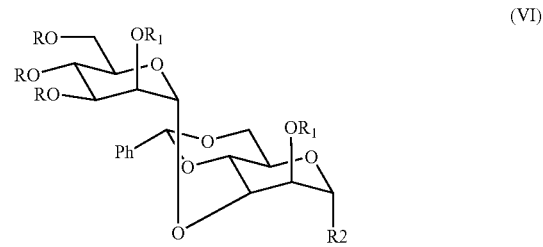

(VI)

in which:
    R is a permanent protector group; a benzyl group can be cited as an example of such a protector group.
    R1 is a temporary protector group; an acetate group can be cited as an example of such a protector group.
    R2 is:
        in the case of an intermediary block, a starting group and in this case the block can be associated with the rest of the polymer at α; a thiophenyl (SPh) can be cited as an example of such a starting group, in the case of a terminal block, a group selected from among an alkyl or benzyl group, or a connector at α or β.

The above dimannosides can be used for preparing tetramannosides of the invention.

The tetramannoside D-Man β(1-2) D-Man β(1-2) D-Man β(1-2) D-Man of formula (I) can be prepared from two Man β(1-2) blocks of formula (V), one of which is an intermediary diblock in which R2 is a starting group, for example R2=—SOPh, forming a β bond, and the other of which is a terminal diblock in which R2 is, for example, an SPh.

The tetramannoside D-Man α(1-2) D-Man α(1-2) D-Man α(1-2) D-Man of formula (II) can be prepared from Man α(1-2) Man blocks of formula (IV), one of which is an intermediary diblock in which R2 is a starting group, for example R2 represents a —C(NH)—CCl$_3$ group, and the other is a terminal diblock in which R2 is —Sph.

The tetramannoside D-Man α(1-3) D-Man α(1-2) D-Man α(1-2) D-Man α(1-2) of formula (III) can be prepared from a Man α(1-3) diblock of formula (VI) and a Man α(1-2) Man diblock of formula (IV). The intermediary diblock is Man α(1-3) Man of formula (VI) in which R2 is a starting group, for example, R2 is —SPh and the terminal diblock is Man α(1-2) Man in which R2 represents the R group defined in formula (III).

As previously stated, the synthetic oligomannosides of the invention are useful for the in vitro detection on a specimen from a patient of the presence of an infection by an infectious organism or pathogen, notably a yeast, a fungus, a virus or a *bacterium* whose cellular envelope contains oligomannosides. Such a process consists of bringing into contact at least one synthetic oligomannoside as defined previously, preferably affixed to a solid support, with a biological sample capable of containing antibodies directed against the infectious organism or pathogen, and then implementation of the detection by any appropriate means of an antigen-antibody complex. The invention concerns more particularly the diagnosis of an infection by *C. albicans* or *S. cerevisiae*, or in the case of Crohn's disease the disclosure of anti-*S. cerevisiae* antibodies.

We have found that the tetramannosides D-Man β(1-2) D-Man β(1-2) D-Man β(1-2) D-Man of formula (I) and D-Man α(1-2) D-Man α(1-2) D-Man α(1-2) D-Man of formula (II) enable specific detection of an infection by *C. albicans* and, thus, the diagnosis of candidiasis.

We have similarly found that the tetramannoside D-Man α(1-3) D-Man α(1-2) D-Man α(1-2) D-Man α(1-2) of formula (III) enables specific detection of anti-*S. cerevisiae* antibodies and can advantageously be employed in ASCA tests for the diagnosis of Crohn's disease.

We furthermore found that in a surprising manner the tetramannoside D-Man α(1-3) D-Man α(1-2) D-Man α(1-2) D-Man α(1-2) of formula (III) can be used in the framework of ASCA tests for diagnosing or predicting viral hepatitis, autoimmune diseases or inflammatory diseases.

Thus, the invention relates to a process for detecting anti-oligomannoside antibodies for diagnosing or predicting an infectious and/or inflammatory pathology, characterized in that at least one of the previously described synthetic oligomannosides is brought into contact with a biological specimen.

More particularly, the invention pertains to a process for detecting anti-*S. cerevisiae* antibodies for diagnosing Crohn's disease or viral hepatitis, characterized in that at least one of the previously described synthetic oligomannosides is brought into contact with a biological specimen.

The synthetic oligomannoside is advantageously the tetramannoside D-Man α(1-3) D-Man α(1-2) D-Man α(1-2) D-Man α(1-2) of formula (III).

The invention also relates to a kit for diagnosing on a biological specimen from a patient of an infection by an infectious organism or pathogen, notably a yeast, a fungus, a virus or a *bacterium* whose cellular envelope contains oligomannosides. Such a kit comprises at least one synthetic oligomannoside as previously defined, advantageously affixed on a solid support such as an ELISA plate, means for detecting formation of antigen-antibody complexes and optionally control reagents.

The research we performed in the framework of the invention led to our discovery that the previously defined synthetic oligomannosides can be used to inhibit colonization by infectious agents or pathogens whose membranes contain oligomannosides. The yeasts of the genus *Candida* use surface sugars from their wall to attach themselves to the cells of their host, cells of the vagina or of the gastrointestinal tract. We found that the sugars, notably from yeasts, protect against infections notably those caused by *C. albicans*, as well as other microbes expressing the same sugars, for example, LPS of *Salmonella, E. coli*.

More particularly, we found in a model of vaginal candidiasis that the tetramannoside D-Man β(1-2) D-Man β(1-2) D-Man β(1-2) D-Man of formula (I) reduced colonization by *C. albicans* in a very significant manner. Similarly, the tetramannoside D-Man β(1-2) D-Man β(1-2) D-Man β(1-2) D-Man of formula (I) was found to be very protective in experimental models of gastrointestinal colonization by *C. albicans*.

The invention consequently concerns therapeutic applications of the previously described synthetic oligomannosides or of conjugates formed by a synthetic oligomannoside coupled with a substance capable of making the sugar immunogenic such as, for example, tetanus anatoxin as well as the monoclonal or polyclonal antibodies directed specifically against said conjugates. These antibodies are useful as research tools and also for developing diagnostic tools.

Thus, the invention also concerns pharmaceutical compositions comprising as an active agent at least one synthetic oligomannoside as previously described, optionally conjugated, associated in the composition with a pharmaceutically acceptable vehicle. These pharmaceutical compositions can be applied locally or generally in a manner to induce inhibition of colonization or protection by local or general immunization depending on the type of infection observed.

The invention envisages more specifically the conjugates formed from D-Man β(1-2) D-Man β(1-2) D-Man β(1-2) D-Man.

Thus, in a surprising manner, we found the inhibitory properties of the nonconjugated oligomannosides, notably in the case of intestinal colonization by *C. albicans* and in the case of vaginal candidiasis.

EXAMPLE 1

Preparation of D-Man β(1-2) D-Man β(1-2) D-Man β(1-2) D-Man of formula (I)

I-Reaction Diagram

Figure 1B:
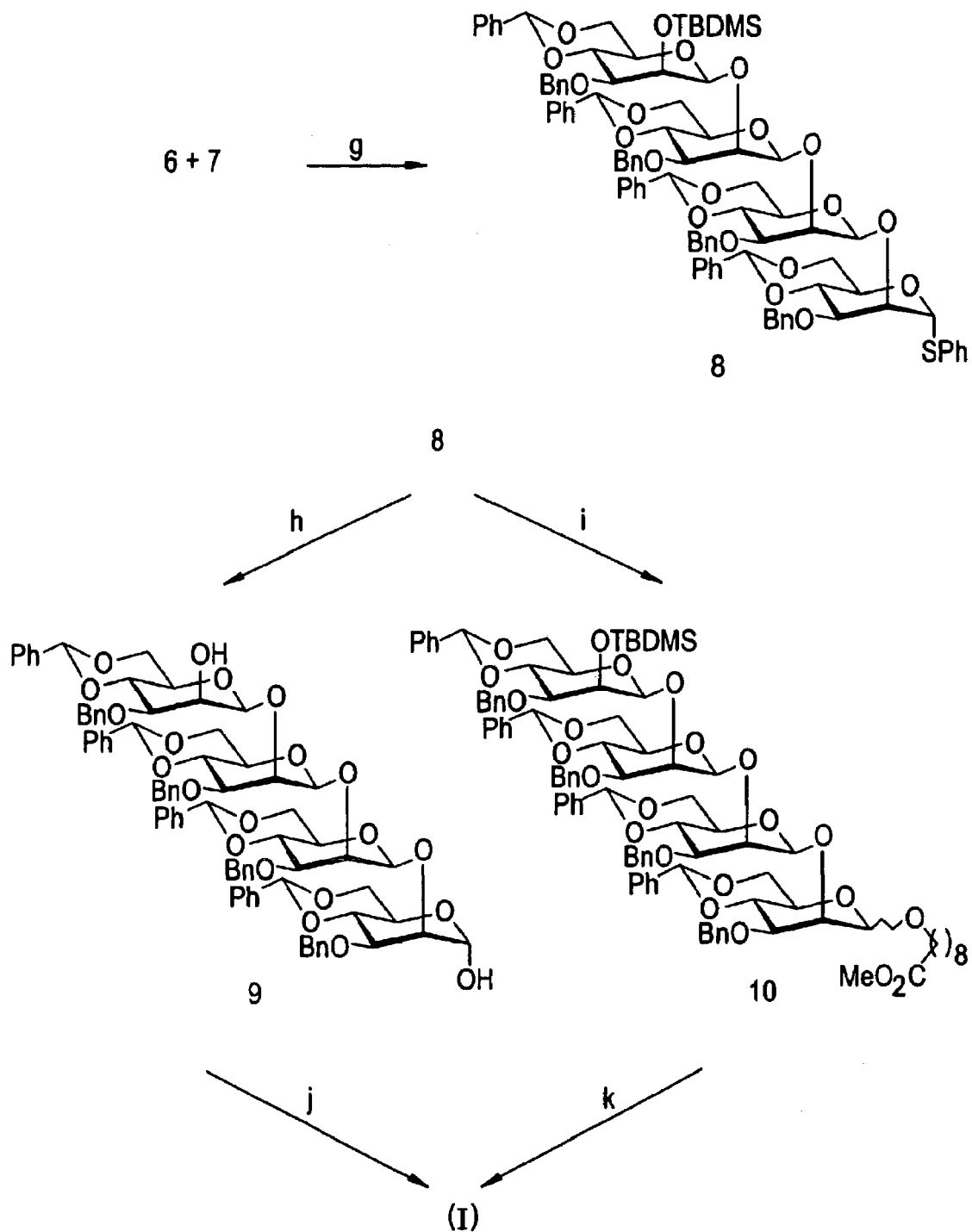

FIG. 1 is a reaction diagram for preparing D-Man β(1-2) D-Man β(1-2) D-Man β(1-2) D-Man of formula (I).

the compound of formula 1 (Stutz, A. et al., 1985, Carbohydr. Res. 137, 282–290) was prepared by reaction of PhCH(OMe)$_2$ on phenyl 1-thio-α-D-mannopyranoside (Maity, S. K. et al., 1994, Tetrahedron, 50, 6965–6974) in DMF in the presence of HBF$_4$Et$_2$O. Selective benzylation yielded compound 2. This compound was silylated and oxidized to yield compound 4.

Reaction (a) was performed under the following conditions: BnBr, Bu$_2$SnO, NBu$_4$Br, toluene, 110° C.

Reaction (b) was performed under the following conditions: TBDMSOTf, Et$_3$N, CH$_2$Cl$_2$.

Reaction (c) was performed under the following conditions: MCPBA, CH$_2$Cl$_2$, −40° C.

Disaccharides and tetrasaccharides bearing a thiophenyl were prepared by first condensing compounds 2 and 4. The condensation between 2 and 4 yielded the disaccharide 5, which was activated into sulfoxide to yield compound 7 or deprotected at position 2 to yield the acceptor 6. Condensation of compounds 6 and 7 yielded the key tetrasaccharide 8.

Reaction (d) was performed under the following conditions: Tf$_2$O, 2,6-diterbutyl pyridine or 2,6-diterbutyl-4-methyl pyridine (DBMP), CH$_2$Cl$_2$, −78° C.

Reaction (e) was performed under the following conditions: b) NBu$_4$F.3H$_2$O, THF.

Reaction (f) was performed under the following conditions: MCPBA, −40° C., CH$_2$Cl$_2$.

Reaction (g) was performed under the following conditions: Tf$_2$O, DBMP, CH$_2$Cl$_2$, −0° C.

8-methoxycarbonyloctanol was selected as the connector. This compound can be prepared according to Lemieux (Lemieux, R. U. et al., 1975, J. Am. Chem. Soc., 97, 4076–4083) from azelaic acid or preferably by ozonolysis of methyl oleate and reduction in situ of the aldehyde formed by NaBH$_4$ (Gerlach, H. et al., 1978, Helv. Chim. Acta, 61, 1226–1231).

Compound 8 was then transformed into 9 by elimination of the silyl by NBu$_4$NF, reaction with water in the presence of NBS, then into the tetramannoside of formula (I) in which R was H by deprotection of the benzyls and benzylidenes.

Glycosylation of compound 8 with 8-methoxycarbonyloctanol yields compound 10 which yields after deprotection the tetramannoside of formula (I) in which R is —(CH$_2$)$_8$—CO$_2$Me.

Reaction (h) was performed under the following conditions: NBu$_4$F.3H$_2$O, THF; then NBS, H$_2$O, acetone.

Reaction (i) was performed under the following conditions: NBS, TfOH, 8-methoxycarbonyloctanol, 4-Angstrom molecular sieve, CH$_2$Cl$_2$.

Reaction (j) was performed under the following conditions: H$_2$, Pd/C, MeOH, AcOEt.

Reaction (k) was performed under the following conditions: 1-NBu$_4$NF.3H$_2$O, THF; 2-H$_2$, Pd/C, MeOH, AcOEt, 3-NaOH, THF, H$_2$O.

II-Experimental Protocol

1) General

The melting points were measured on a Büchi 510 capillary apparatus and not corrected. The rotatory powers were measured at ambient temperature with a Perkin-Elmer 241 polarimeter. The mass spectra in chemical ionization mode (ammonia) were obtained with a Nermag R10-10 spectrometer. The elemental analyses were performed by the Microanalysis Department of Université Pierre et Marie Curie (Paris VI). The NMR proton spectra were recorded on Bruker devices at 250 or 400 MHz in solution in deuterized chloroform. The chemical displacements were given in ppm in relation to TMS; the following abbreviations were used: s (singlet), bs (broadened singlet), d (doublet), bd (broadened doublet), t (triplet), q (quadruplet) and m (multiplet); by (benzylidene). The thin-layer chromatographs were performed on Merck 60 F$_{254}$ silica plates and developed by vaporization of an alcohol solution of concentrated sulfuric acid (20% v/v) and heating. The column chromatographs (flash) were performed on silica gel 60 (230–400 mesh, Merck).

1) Phenyl 3-O-benzyl-4,6-O-benzylidene-1-thio-α-D-mannopyranoside (2)

This compound is described in the literature: Z. Szurmai, L. Balatoni, A. Liptak, Carbohydr. Res., 254 (1994) 301–309 and T. Oshitari, S. Kobayashi, Tetrahedron Lett. (1995) 1089–92. The description below applies to a synthesis that can be used for large quantities (with two variants corresponding to two different solvents).

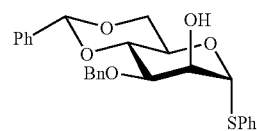

Method 1 (the Solvent is Toluene):

To a solution of 1 (known compound: H. Franzyk, M. Medal, H. Paulsen, K. Bock, J. Chem. Soc. Perkin Trans I, (1995) 2883–98, advantageously prepared according to R. Albert, K. Dax, R. Pleschko, A. Stütz, Carbohydr. Res. 137 (1985) 282–290) (10 g, 28 mmol) in 295 ml of anhydrous toluene, we added 7.5 g of dibutyltin oxide. The mixture was brought to reflux of toluene with a Dean Stark apparatus overnight. Tetrabutylammonium iodide (6.59 g), then benzyl bromide (4.3 ml) were added. Agitation was maintained for 3 h under reflux, then the mixture was brought to ambient temperature (cyclohexane/ethyl acetate control=3/1) and concentrated under vacuum. The resultant residue was purified by column chromatography (elution: cyclohexane/ethyl acetate=4/1) which yielded product 2 (11 g, 89%).

Method 2 (the solvent is acetonitrile):

Compound 1 (9.05 g, 25.11 mmol) and 450 ml of anhydrous acetonitrile were introduced into a flask. Heating was performed at the reflux of CH$_3$CN under argon (compose 1 dissolved in hot acetonitrile). When the solution was clear, we added 23.53 of screen 4 Å in powder form, 7.51 g of Bu$_2$SnO. This was left at reflux for 6 hours. It was allowed to return to ambient temperature. We added 8.10 g of nBu$_4$N$^+$Br$^-$ (1 eq), 6.3 ml of benzyl bromide (2.3 eq) and then performed agitation overnight at 45 ° C. Filtration was performed through a fritted funnel covered with Celite; the solids were rinsed with dichloromethane and concentrated under vacuum. The resultant residue was purified by column chromatography (elution: cyclohexane/ethyl acetate=3/1) which yielded product 2 (10.2 g, 90%).

$^1$H-NMR: (250 MHz, CDCl$_3$): δ 5.55 (s, 1H, By); 5.52 (s, 1H, H-1); 4.82 (d, 1H, J$_{gem}$=11.75 Hz, CHPh); 4.67 (d, 1H, J$_{gem}$=11.75 Hz, CHPh); 4.27 (ddd, 1H, H-5); 4.21 (d, 1H, J$_{2-3}$=3.54 Hz, H-2); 4,14 (dd, 1H, J$_{6a-6b}$=9.73 Hz and J$_{6a-5}$=4.80 Hz, H-6a); 4.11 (t, 1H, H-4); 3.89 (dd, 1H, J$_{3-4}$=9.50 Hz and J$_{3-2}$=3.37 Hz, H-3); 3.78 (t, 1H, J$_{6b-5}$=10.18 Hz and J$_{6b-6a}$=10.18 Hz, H-6b); 2.79 (s, 1H, O—H).

2) Phenyl 2-O-tertbutyldimethylsilyl-3-O-benzyl-4,6-benzylidene-1-thio-α-D-mannopyranoside (3)

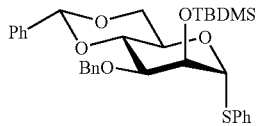

We introduced into a flask under argon atmosphere compound 2 (5.51 g, 12.23 mmol) and 55 ml of anhydrous dichloromethane. We added under agitation: 5.3 ml of triethylamine (3.1 eq), 4.65 ml of terbutyldimethylsilyl triflate (1.65 eq). Agitation was performed overnight at ambient temperature. CCM was used to monitor the advancement state of the reaction (elution: cyclohexane/ethyl acetate=3/1. Neutralization was performed with an aqueous solution of NaHCO$_3$. The organic phase was concentrated under vacuum which yielded a residue; the residue was purified by column chromatography (elution: cyclohexane/ethyl acetate=96/4), which yielded product 3 (6.2 g, 90%). Rf: (cyclohexane/AcOEt=96/4): 0.43. $(\alpha)_D$=+122 (c 1.2; CHCl$_3$).

$^1$H-NMR (250 MHz, CDCl$_3$): δ 5.55 (s, 1H, By); 5.24 (d, 1H, J$_{1-2}$=1.4 Hz, H-1); 4.69 (dd, 2H, CHPh); 4.26–4.08 (massive, 4H); 3.83–3.65 (massive, 2H); 0.81 (s, 9H, Si-tBu); 0.00 (s, 3H, Si—Me); −0.4 (s, 3H, Si—Me).

Analysis for C$_{32}$H$_{40}$O$_5$SSi (564.821): calculated=C: 68.04 H: 7.14; found: C: 68.15 H: 7.27.

3) Phenyl (2-O-tertbutyldimethylsilyl-3-O-benzyl-4,6-O-benzylidene-α-D-mannopyranoside) sulfoxide (4)

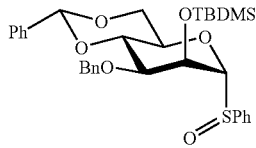

We introduced into a flask under argon atmosphere compound 3 (6.62 g, 10.97 mmol) and 125 ml of anhydrous dichloromethane. Into the flask cooled to −78° C., we added perbenzoic 3-chloro acid (12.06 mmol) in solution in 26 ml of dichloromethane. The temperature was maintained at −78° C. for 15 minutes and then allowed to gradually come to −30° C. We added (CH$_3$)$_2$S to eliminate the excess of peracid. Neutralization was performed with a saturated solution of NaHCO$_3$; the mixture was then washed with a saturated solution of NaCl and the aqueous phases were extracted with dichloromethane. The organic phase was dried (MgSO$_4$), filtered and then concentrated. The resultant residue was purified by column chromatography (elution: cyclohexane/ethyl acetate=5/1) which yielded 4 (5.04 g, 79% majority diastereoisomer). The other diastereoisomer was recovered during chromatography in a very small proportion (<5%).

Characteristics of the majority isomer: $(\alpha)_D$=−67 (c 1.0; CHCl$_3$).

$^1$H-NMR: (400 MHz, CDCl$_3$): δ 7.70–7.20 (m, 15H, arom.); 5.69 (s, 1H, By; 4.93 and 4.82 (2d, 2H, CHPh); 4.73 (dd, 1H, J$_{1,2}$=1.2, J$_{2,3}$=2.3 Hz, H-2); 4.39 (d, 1H, H-1); 4.30 (dd, 1H, J$_{3,4}$=9.9; J$_{4,5}$=9.9 Hz; H-4); 4.28 (dd, 1H, H-3); 4.26 (dd, 1H, J$_{61,6b}$=10.3; J$_{6b,5}$=5.8 Hz, H-6b); 4.14 (ddd, 1H, J$_{5,6a}$=120.1 Hz, H-5); 3.79 (dd, 1H, H-6a); 0.88 (s, 9H, tBu); 0.072 and −0.046 (2s, 6H, MeSi).

Mass spectrum: m/z 598 (M+NH$_4$)$^+$.

Analysis for C$_{32}$H$_{40}$O$_6$SSi(654.821): calculated=C: 66.17 H: 6.94; found=C: 66.30 H: 7.06.

4) Phenyl 2-O-(3-O-benzyl-4,6-O-benzylidene-2-O-tertbutyldimethylsilyl-β-D-mannopyranosyl)-3-O-benzyl-4,6-O-benzylidene-1-thio-α-D-mannopyranoside (5)

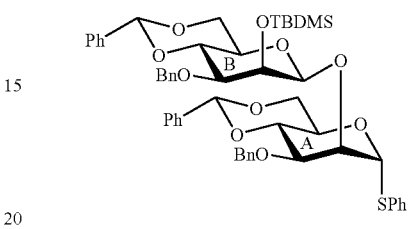

7.1 g (12.22 mmol, 1 eq) of 4 and 9.06 ml (40.3 mmol, 3.3 eq) of 2,6-ditertbutylpyridine were dissolved in 200 ml of anhydrous dichloromethane and placed under an argon atmosphere. After having cooled the solution to −78° C., 2.27 ml (13.44 mmol, 1.1 eq) of trifluoromethanesulfonic acid anhydride were added. After 5 min of agitation at −78° C., 11 g (24.4 mmol, 2 eq) of 2, previously diluted in 100 ml of anhydrous dichloromethane, were added drop by drop. The temperature was maintained for 1 hour at −78° C. and allowed to slowly climb to 0° C. The reactional medium was then neutralized with a solution of sodium bicarbonate. The organic phase was then washed with an aqueous solution of NaCl, dried over magnesium sulfate, filtered and evaporated under vacuum. Silica gel chromatography (elution: cyclohexane/ethyl acetate=96/4) of the crude product produced 5 (7.97 g, 72%) in the form of a white foam. m.p.: 81–83° C. (hexane); $(\alpha)_D$ +12.5 (c 1.02, chloroform).

$^1$H-NMR (400 MHz, CDCl$_3$): δ 7.58–7.34 (m, 25H, arom.), 5.66 and 5.65 (2s, 2H, by), 5.56 (d, 1H, J$_{1-2}$=1 Hz, H-1A), 4.85 (2d, 2H, J$_{gem}$=12 Hz, CHPh), 4.8 (d, 1H, J$_{gem}$=12 Hz, CHPh), 4.75 (d, 1H, J$_{gem}$12 Hz, CHPh), 4.53 (dd, 1H, J$_{2-1}$=1 Hz and J$_{2-3}$=3.3 Hz, H-2A), 4.52 (bs, 1H, H-1B), 4.45–4.4 (m, 1H, H-5A), 4.37 (t, 1H, J$_{4-3}$=J$_{4-5}$=9.5 Hz, H-4A), 4.31 (dd, 1H, J$_{6b-6a}$=10 Hz and J$_{6b-5}$=4.3 Hz, H-6Ab), 4.26 (dd, 1H, J$_{6b-6a}$=10.3 Hz and J$_{6b-5}$=4.8 Hz, H-6Bb), 4.21 (t, 1H, J$_{4-3}$=J$_{4-5}$=9.5H, H-4B), 4.19 (bd, 1H, J$_{2-3}$=2.7 Hz, H-2B), 4 (dd, 1H, J$_{3-2}$=2.7 Hz and J$_{3-4}$=9.5 Hz, H-3A), 3.91 (t, 1H, J$_{6a-6b}$=J$_{6a-5}$=10H, H-6Aa), 3.84 (t, 1H, J$_{6a-6b}$=J$_{6a-5}$=10.2 Hz, H-6Ba), 3.59 (dd, 1H, J$_{3-2}$=2.7 Hz and J$_{3-4}$=9.5 Hz, H-3B), 3.35 (dt, 1H, J$_{5-4}$=J$_{5-6a}$=10.2 Hz and J$_{5-6}$=4.8 Hz, H-5B), 1.0 (s, 9H, SiC(CH$_3$)$_3$), 0.30 and 0.23 (2s, 6H, Si(CH$_3$)$_2$).

$^{13}$C NMR (100 MHz): δ 138.44, 138.3, 137.5, 137.4, 133.6 (5 C arom.), 131.8–126.06 (25 CH arom.), 101.6 (CH by), 101.4 (CH by), 99.8 ($^1$J$_{CH}$=157 Hz, C-1B), 86.7 ($^1$J$_{CH}$=166 Hz, C-1A), 78.7 (C-4B), 78.2 (C-4A), 77.5 (C-3B), 76.4 (C-2A), 74 (C-3A), 72.2 (CH$_2$Ph), 71.7 (C-2B), 70.7 (CH$_2$Ph), 68.5 (C-6B), 68.47 (C-6A), 67.7 (C-5B), 65.2 (C-5A), 26 (C(CH$_3$)$_3$), 18.5 (C(CH$_3$)$_3$, −4 (SiCH$_3$), −4.5 (SiCH$_3$).

Mass spectrum: m/z 922 (M+NH4)$^+$.

Analysis for C$_{52}$H$_{60}$O$_{10}$SSi (905.199): calculated=C: 68.99 H: 6.68; found=C: 68.82 H: 6.69.

5) Phenyl 2-O-(3-O-benzyl-4,6-O-benzylidene-β-D-mannopyranosyl)-3-O-benzyl-4,6-O-benzylidene-1-thio-α-D-mannopyranoside (6)

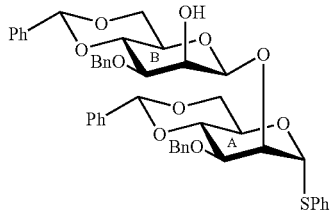

3.8 g (4.2 mmol, 1 eq) of product 5 and 6.6 g (21 mmol, 5 eq) of tetrabutylammonium trihydrate fluoride were dissolved in 60 ml of tetrahydrofuran. After 1 hour at ambient temperature, the medium was diluted with dichloromethane and the organic phase was washed with water. The organic phase was dried over magnesium sulfate, filtered and evaporated under reduced pressure. Silica gel chromatography (elution: cyclohexane/ethyl acetate=3/1) yielded 6 (3.0 g, 90%) in the form of a white powder. m.p.: 79–81° C. (hexane); $(\alpha)_D$ +30 (c 0.33, chloroform).

$^1$H-NMR (400 MHz, CDCl$_3$): δ 7.54–7.30 (m, 25H, arom.), 5.59 and 5.51 (2s, 2H, by), 5.54 (d, 1H, $J_{1-2}$=1 Hz, H-1A), 4.89 (d, 1H, $J_{gem}$=12.2 Hz, CHPh), 4.86 (d, 1H, $J_{gem}$=11.8 Hz, CHPh), 4.82 (d, 1H, $J_{gem}$=11.8 Hz, CHPh), 4.8 (d, 1H, $J_{gem}$=12.2 Hz, CHPh), 4.77 (d, 1H, $J_{1-2}$=0.8 Hz, H-1B), 4.66 (dd, 1H, $J_{2-1}$=1 Hz and $J_{2-3}$=3.3 Hz, H-2A), 4.33 (dt, 1H, $J_{5-4}$=9.7 Hz and $J_{5-6a}$=$J_{5-6b}$=4.9 Hz, H-5A), 4.32 (t, 1H, $J_{4-3}$=$J_{4-5}$=9.3 Hz, H-4B), 4.26 (dd, 1H, $J_{6b-6a}$=10.5 Hz, and $J_{6b-5a}$=4.9 Hz, H-6Bb), 4.3 (dd, 1H, $J_{6b-6a}$=10 Hz and $J_{6b-5}$=5 Hz, H-6Ab), 4.24 (t, 1H, $J_{4-3}$=$J_{4-5}$=9.7 Hz, H-4A), 4.19 (bd, 1H, $J_{2-3}$=3.9 Hz, H-2B), 4.04 (dd, 1H, $J_{3-2}$=3.3 Hz and $J_{3-4}$=9.7 Hz, H-3A), 3.8 (m, 2H, H-6Aa and H-6Ba), 3.72 (dd, 1H, $J_{3-2}$=3.9 Hz and $J_{3-4}$=9.2 Hz, H-3B), 3.43 (dt, 1H, $J_{5-4}$=$J_{5-6b}$=9.5 Hz and $J_{5-6a}$=4.9 Hz, H-5B), 3.2 (br, 1H, OH).

$^{13}$C-NMR (100 MHz): δ 138, 137.8, 137.3, 137.29, 131.7 (5 C arom.), 129.2–127.7 (25 CH arom.), 101.4 (CH by), 101.2 (CH by), 97.4 ($^1J_{CH}$=163 Hz, C-1B), 86.4 ($^1J_{CH}$=167 Hz, C-1A), 78.5 (C-4A), 78.4 (C-4B), 76.1 (C-3B), 74.4 (C-3A), 74.35 (C-2A), 72.4 (CH$_2$Ph), 72.3 (CH$_2$Ph), 69.4 (C-2B), 68.5 (C-6B), 68.25 (C-6A), 66.8 (C-5B), 65.2 (C-5A).

Mass spectrum: m/z 808 (M+NH4)$^+$.

Analysis for C$_{46}$H$_{46}$O$_{10}$S (790.93): calculated=C: 69.85 H: 5.86; found=C: 69.76 H: 6.01.

6) Phenyl (2-O-(3-O-benzyl-4,6-O-benzylidene-2-O-tertbutyldimethylsilyl-β-D-mannopyranosyl)-3-O-benzyl-4,6-O-benzylidene-α-D-mannopyranosyl) sulfoxide (7)

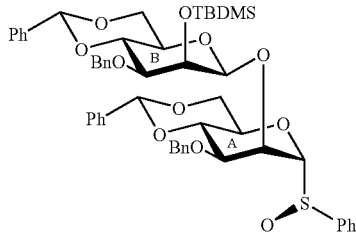

3.0 g (3.31 mmol, 1 eq) of 5 were dissolved in 40 ml of anhydrous dichloromethane. After cooling the reactional medium to –78° C., 0.97 g (5.5 mmol, 1.7 eq) of 3-chloroperoxybenzoic acid at 85%, previously dissolved in 15 ml of dichloromethane, was added via a cannula. After 15 min of agitation at –78° C., the temperature was allowed to climb to –30° C. and several drops of dimethyl sulfide were added. The organic phase was then washed with a solution of sodium bicarbonate, an aqueous solution of NaCl, dried (MgSO$_4$), filtered and evaporated under vacuum. Gel chromatography (elution: cyclohexane/ethyl acetate=4/1, and then 3/1) of the crude product yielded 2.8 g (91%) of a first 7 diastereoisomer in the form of a white foam and 71 mg (2%) of a second diastereoisomer also in the form of a white foam.

Characteristics of the majority diastereoisomer: m.p.: 89–91° C. (hexane); $(\alpha)_D$ –99 (c 1, chloroform).

$^1$H-NMR (400 MHz, CDCl$_3$): δ 7.65–7.4 (m, 25H, arom.), 5.63 and 5.62 (2s, 2H, by), 4.89 (1d, 1H, $J_{gem}$=12 Hz, CHPh), 4.85 (d, 1H, $J_{gem}$=12.4 Hz, CHPh), 4.81 (dd, 1H, $J_{2-1}$=1.1 Hz and $J_{2-3}$=3.4 Hz, H-2A), 4.78 (d, 1H, $J_{gem}$=12.4 Hz, CHPh), 4.76 (1d, 1H, $J_{gem}$=12 Hz, CHPh), 4.42 (d, 1H, $J_{1-2}$=1.1 Hz, H-1A), 4.37 (t, 1H, $J_{4-3}$=$J_{4-5}$=10.1 Hz, H-4A), 4.33 (dd, 1H, $J_{3-2}$=3.4 Hz and $J_{3-4}$=10.1 Hz, H-3A), 4.28 (dd, 1H, $J_{6b-6a}$=10.2 Hz and $J_{6b-5}$=4.8 Hz, H-6Ab), 4.26 (bs, 1H, H-1B), 4.18–4.10 (m, 3H, H-5A, H-6Bb and H-4B), 4.08 (bd, 1H, $J_{2-3}$=2.8 Hz, H-2B), 3.75 (t, 1H, $J_{6a-6b}$=$J_{6a-5}$=10.1 Hz, H-6Aa), 3.74 (dd, 1H, $J_{6b-6a}$=$J_{6b-5}$=10.2 Hz, H-6Ba), 3.52 (dd, 1H, $J_{3-2}$=2.8 Hz and $J_{3-4}$=9.7 Hz, H-3B), 3.18 (dt, 1H, $J_{5-4}$=$J_{5-6}$=9.8 Hz and $J_{5-6}$=4.8 Hz, H-5B), 1 (s, 9H, SiC(CH$_3$)$_3$), 0.22 and 0.17 (2s, 6H, Si(CH$_3$)$_2$).

$^{13}$C-NMR (100 MHz): δ 141.3, 138.4, 138.3, 137.5, 137 (5 C arom.), 131.8–124.3 (25 CH arom.), 101.7 (CH by), 101.4 (CH by), 99.8 ($^1J_{CH}$=156 Hz, C-1B), 97.5 ($^1J_{CH}$=163 Hz, C-1A), 78.7 (C-4B), 77.5 (C-3B), 77.1 (C-4A), 74.2 (C-3A), 72.4 (CH$_2$Ph), 71.7 (C-2B), 71.4 (C-2A), 70.9 (CH$_2$Ph), 70.1 (C-5A), 68.4 (C-6B), 68.1 (C-6A), 67.5 (C-5B), 26 (C(CH$_3$)$_3$), 18.5 (C(CH$_3$)$_3$), –4 (SiCH$_3$), –4.5 (SiCH$_3$).

Analysis for C$_{46}$H$_{46}$O$_{10}$S (921.198): calculated=C: 67.8 H: 6.56; found=C: 67.68 H: 6.90).

7) Phenyl 2-O-(2-O-(2-O-(3-O-benzyl-4,6-O-benzylidene-2-O-tertbutyldimethylsilyl-β-D-mannopyranosyl)-3-O-benzyl-4,6-O-benzylidene-β-D-mannopyranosyl)-3-O-benzyl-4,6-O-benzylidene-β-D-mannopyranosyl)-3-O-benzyl-4,6-O-benzylidene-1-thio-α-D-mannopyranoside (8)

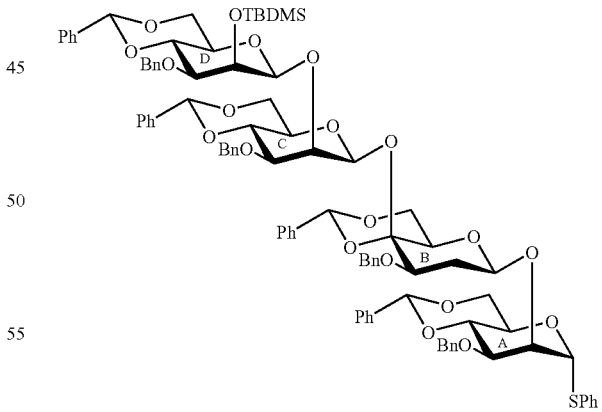

The experimental protocol was the same as that for the synthesis of disaccharide 5. We obtained from 6 (1.140 g, 2 eq) and 7 (0.664 g, 1 eq) compound 8 (580 mg, 55%) in the form of a white foam after silica gel chromatography (elution: cyclohexane/ethyl acetate=85/15). m.p.: 111–114° C. (hexane); $(\alpha)_D$ –53.5 (c 0.6, chloroform).

$^1$H-NMR (400 MHz, CDCl$_3$): δ 7.5–7.15 (m, 45H, arom.), 5.615*2, 5.61 and 5.6 (4s, 4H, by), 5.53 (d, 1H, $J_{1-2}$=1.1 Hz, H-1A), 5.35 (bs, 1H, H-1B), 5.03 (bs, 1H, H-1C), 4.82 (d, 1H, $J_{gem}$=12.8 Hz, CHPh), 4.76 (s, 2H, CH$_2$Ph), 4.73 (d, 1H, $J_{gem}$=12.8 Hz, CHPh), 4.72 (bs, 1H, H-1D), 4.72 (d, 1H, $J_{gem}$=11.6 Hz, CHPh), 4.67 (d, 1H, $J_{gem}$=11.6 Hz, CHPh), 4.67 (d, 1H, $J_{gem}$=17.7 Hz, CHPh), 4.57 (d, 1H, $J_{gem}$=11.6 Hz, CHPh), 4.58–4.57 (m, 1H, H-2A), 4.57 (bd, 1H, $J_{2-3}$=3.2 Hz, H-2B), 4.57 (2bd, 2H, $J_{2-3}$=3.2 Hz, H-2C and H-2D), 4.42–4.37 (m, 1H, H-5A), 4.39–4.35 (m, 2H, H-6Db and H-6Bb), 4.38 (d, 1H, $J_{gem}$=11.7 Hz, CHPh), 4.29 (dd, 1H, $J_{6b-6a}$=10.2 and $J_{6b-4}$=4.8 Hz, H-6Ab), 4.24 (dd, 1H, $J_{4-3}$=10 and $J_{4-5}$=9.6 Hz, H-4b), 4.16 (t, 1H, $J_{4-3}$=$J_{4-5}$=9.7 Hz, H-4C), 4.13 (dd, 1H, $J_{6b-6a}$=10.2 and $J_{6b-5}$=4.7 Hz, H-6Cb), 4.05 (t, 1H, $J_{4-3}$=$J_{4-5}$=10 Hz, H-4A), 4.02 (t, 1H, $J_{4-3}$=$J_{4-5}$=10 Hz, H-4D), 4.05–4.02 (m, 1H, H-3A), 4 (t, 1H, $J_{6a-6b}$=$J_{6a-5}$=10.3 Hz, H-6Ba), 3.89 (t, 1H, $J_{6a-6b}$=$J_{6a-5}$=10.2 Hz, H-6Da), 3.8 (t, 1H, $J_{6a-6b}$=$J_{6a-5}$=10.2 Hz, H-6Aa), 3.79 (t, 1H, $J_{6a-6b}$=$J_{6a-5}$=10.2 Hz, H-6Aa), 3.79 (t, 1H, $J_{6a-6b}$=$J_{6a-5}$=10.2 Hz, H-6Ca), 3.69 (dd, 1H, $J_{3-2}$=3.2 Hz and $J_{3-4}$=9.9 Hz, H-3D), 3.58 (dd, 1H, $J_{3-2}$=2.7 Hz and $J_{3-4}$=9.7 Hz, H-3C), 3.55 (dd, 1H, $J_{3-2}$=3.2 Hz and $J_{3-4}$=10 Hz, H-3B), 3.49 (ddd, 1H, $J_{5-4}$=9.6 Hz and $J_{5-6b}$=10.3 Hz and $J_{5-6a}$=4.8 Hz, H-5B), 3.42 (ddd, 1H, $J_{5-4}$=9.8 Hz and $J_{5-6b}$=4.8 Hz and $J_{5-6a}$=10.2 Hz, H-5D), 3.31 (ddd, 1H, $J_{5-4}$=9.7 Hz and $J_{5-6b}$=4.75 Hz and $J_{5-6a}$=10.1 Hz, H-5D), 0.95 (s, 9H, SiC(CH$_3$)$_3$), 0.25 and 0.14 (2s, 6H, Si(CH$_3$)$_2$).

$^{13}$C-NMR (100 MHz): δ 138.6, 138.4, 138.1, 138, 137.7, 137.4, 136.95, 136.93, 133.2 (9 C arom.), 131-65-126 (45 CH arom.), 103.1 ($^1J_{CH}$=159 Hz, C-1C), 102.05 (CH by), 102.02 (CH by), 101.6 (CH by), 101.2 (CH by), 101.19 (($^1J_{CH}$=158.5 Hz, C-1B), 99 (($^1J_{CH}$=167 Hz, C-1A), 85.4 (($^1J_{CH}$=159.2 Hz, C-1D), 79.7 (C-3C), 79.05 (C-4C), 78.9 (C-4A), 78.5 (C-4D), 77.6 (C-4B), 76.9 (C-3B), 75.8 (C-3D), 75.3 (C-2B), 75.2 (C-2A), 74.4 (C-3A), 73.1 (C-2C or C-2D), 72.8 (CH$_2$Ph), 71.9 (CH$_2$Ph), 71.2 (C-2C or C-2D), 70.9 (CH$_2$Ph), 70.1 (CH$_2$Ph), 68.8 (C-6a), 68.7 (C-6D and C-6B), 68.5 (C-6C), 68.1 (C-5B), 67.8 (C-5C), 67.7 (C-5D), 65.1 (C-5A), 26.1 (C(CH$_3$)$_3$), 18.5 (C(CH$_3$)$_3$), −3.7 (SiCH$_3$), −4.7 (SiCH$_3$).

Mass spectrum: m/z 1602 (M+NH4)$^+$.

Analysis for C$_{92}$H$_{100}$O$_{20}$SSi (1585.956): calculated=C: 69.67 H: 6.35; found=C: 69.57 H: 6.41.

8) 8-methoxycarbonyloctyl 2-O-(2-O-(2-O-(3-O-benzyl-4,6-O-benzylidene-2-O-tertbutyldimethylsilyl-β-D-mannopyranosyl)-3-O-benzyl-4,6-O-benzylidene-β-D-mannopyranosyl)-3-O-benzyl-4,6-O-benzylidene-β-D-mannopyranosyl)-3-O-benzyl-4,6-O-benzylidene-D-mannopyranoside (10)

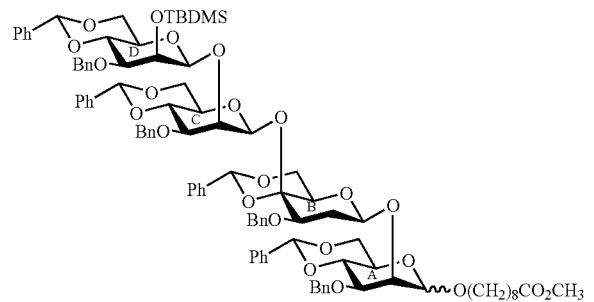

562 mg (354 μmol, 1 eq) of 8, 166 mg (885 μmol, 2.5 eq) of methoxycarbonyl-octan-1-ol (prepared according to H. Gerlach, P. Künzler, K. Oertle, *Helv. Chim. Acta*, 61 (1978), 1226–1231) and 700 mg of 4-Å molecular sieve in powder form were put in suspension in 10 ml of anhydrous dichloromethane. The entire mixture was put under an argon atmosphere and agitated for 30 min. The solution was cooled to −20° C. and 126 mg (709 μmol, 2 eq) of N-bromosuccinimide as well as 6.3 μl (7.08 μmol, 0.2 eq) of trifluoromethanesulfonic acid were added to it. After 1 hour at −20° C., a solution of sodium bicarbonate was added. The entire mixture was filtered over a Celite bed. The organic phase was washed with a sodium thiosulfate solution and with an aqueous solution of NaCl. It was then dried over magnesium sulfate, filtered and evaporated under vacuum. The crude product was chromatographed over silica gel (elution: cyclohexane/ethyl acetate=3.5/1) and yielded 412 mg (70%) of compound 10 (α/β=1/6) not separable in the form of a white foam.

$^1$H-NMR (400 MHz, CDCl$_3$) of the β-O-connector product: δ 7.48–7.16 m, 40H, arom.), 5.64, 5.62 and 5.6, 5.34 (4s, 4H, by), 5.34 (s, 1H, H-1A), 5.16 (s, 1H, H-1B), 4.86 (d, 1H, $J_{gem}$=12.3 Hz, CHPh), 4.84 (s, 1H, H-1C), 4.82 (d, 1H, $J_{gem}$=12 Hz, CHPh), 4.79 (d, 1H, $J_{gem}$=12.4 Hz, CHPh), 4.74 (2, 1H, $J_{2-3}$=3.2 Hz, H-2C), 4.73 (d, 1H, $J_{gem}$=12 Hz, CHPh), 4.68 (d, 1H, $J_{gem}$=12.3 Hz, CHPh), 4.67 (d, 1H, $J_{gem}$=11.8 Hz, CHPh), 4.65 (d, 1H, $J_{2-3}$=3.4 Hz, H-2A), 4.63 (d, 1H, $J_{gem}$=12.4 Hz, CHPh), 4.56 (d, 1H, $J_{gem}$=11.8 Hz, CHPh), 4.51 (d, 1H, $J_{2-3}$=3.2 Hz, H-2B), 4.47 (s, 1H, H-1D), 4.41 (dd, 1H, $J_{6b-6a}$=10.4 Hz and $J_{6b-5}$=4.8 Hz, H-6Cb), 4.36 (dd, 1H, $J_{6b-6a}$=10.3 Hz and $J_{6b-5}$=4.8 Hz, H-6Ab), 4.32 (dd, 1H, $J_{6b-6a}$=10.3 Hz, and $J_{6b-5}$=4.5 Hz, H-6Db), 4.28 (t, 1H, $J_{4-3}$=$J_{4-5}$=9.6H, H-4A), 4.23 (dd, 1H, $J_{6b-6a}$=10.4 Hz and $J_{6b-5}$=4.6 Hz, H-6Bb), 4.21 (d, 1H, $J_{2-3}$=3.15 Hz, H-2D), 4.17 (t, 1H, $J_{4-3}$=$J_{4-5}$=9.3 Hz, H-4B), 4.01 (t, 1H, $J_{6a-6b}$=$J_{6a-5}$=10.3 Hz, H-6Aa), 3.99 (t, 1H, $J_{4-3}$$J_{4-5}$=9.5 Hz, H-4C), 3.91 (t, 1H, $J_{6a-6b}$=$J_{6a-5}$=10.4 Hz, H-6Ca), 3.95–3.88 (m, 1H, —O—CH—CH$_2$—), 3.88 (t, 1H, $J_{4-3}$=$J_{4-5}$=9.8 Hz, H-4D), 3.85 (t, 1H, $J_{6a-6b}$=$J_{6a-5}$=10.4 Hz, H-6Ba), 3.69 (s, 3H, —C:O—OCH$_3$), 3.64 (dd, 1H, $J_{3-2}$=3.2 Hz and $J_{3-4}$=9.5 Hz, H-3C), 3.6 (dd, 1H, $J_{3-2}$=3.4 Hz and $J_{3-4}$=9.6 Hz, H-3A), 3.59 (dd, 1H, $J_{3-2}$=3.15 Hz and $J_{3-2}$=9.8 Hz, H-3D, 3.60–3.57 (m, 1H, H-6Da), 3.54 (dd, 1H, $J_{3-2}$=3.2 Hz and $J_{3-4}$=−9.3 Hz, H-3B), 3.5–3.27 (m, 5H, H-5A, H-5B, H-5C, H-5D and —O—CH—CH$_2$—), 2.31 (t, 2H, $J_{3-2}$=7.5 Hz, —CH$_2$C:O—OCH$_3$), 1.64–1.58, 1.34–1.31 (m, 12H, —CH$_2$—), 0.94 (s, 9H, SiC(CH$_3$)$_3$), 0.25 and 0.14 (2s, 6H, Si(CH$_3$)$_2$).

$^{13}$C-NMR (100 MHz): δ 138.5, 138.4, 138.39, 138.2, 137.7, 137.5, 137.1, 137.08 (8 C arom.), 129–126 (40 CH arom.), 103.9 (159.7C-1C), 102.7 ($^1J_{CH}$=160 Hz, C-1D), 101.8 (CH by), 101.6 (CH by), 101.58 ($^1J_{CH}$=155 Hz, C-1A), 101.5 (CH by), 101.35 ($^1J_{CH}$=158.5 Hz, C-1B), 101.2 (CH by), 79.9 (C-3B), 78.97 (C-4B), 78.46 (C-4D), 78.4 (C-4C), 77.9 (C-4A), 77.6 (C-2D), 76.29 (C-3D), 76.27 (C-3C), 76.23 (C-3A), 75.22 (C-2A), 72.83 (C-2C), 72.8 (CH$_2$Ph), 71.9 (CH$_2$Ph), 71.16 (C-2B), 70.62 (CH$_2$Ph), 70.14 (—O—CH$_2$—), 69.8 (CH$_2$Ph), 68.87, 68.82*2, 68.5 (C-6A, C-6B, C-6C and C-6D), 67.88 (C-5B), 67.83 (C-5C), 67.7 (C-5A), 67.4 (C-5B), 34 (—CH$_2$—C:O—O—CH$_3$), 29.5, 29.2, 29.1, 29, 25.5, 24.8 (—CH$_2$—), 25.9 (C(CH$_3$)$_3$), 18.5 (C(CH$_3$)$_3$), −3.7 (SiCH$_3$), −4.7 (SiCH$_3$).

Mass spectrum: m/z 1663.7 (M+H)$^+$.

Analysis for C$_{96}$H$_{114}$O$_{23}$Si (1664.03): calculated=C: 69.29 H: 6.905; found=C: 69.13 H: 7.06.

9) 8-carboxyloctyl 2-O-(2-O-(2-O-(β-D-mannopyranosyl)-β-D-mannopyranosyl)-β-D-mannopyranosyl)-D-mannopyranoside (I, R=connector)

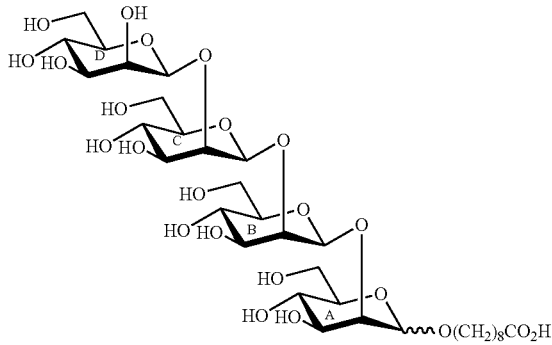

Step 1: Desilylation 305 mg (183 μmol, 1 eq) of compound 10 and 405 mg (1.28 mmol, 7 eq), of tetrabutylammonium trihydrate fluoride were put in solution in 10 ml tetrahydrofuran. After 12 hours of heating at 60° C., the reactional medium was diluted with dichloromethane and washed with water. The organic phase was dried over magnesium sulfate, filtered and evaporated under reduced pressure. Chromatography of the crude product over silica gel (elution: cyclohexane/ethyl acetate=2/1) yielded 230 mg (80%) of the desilylated product in the form of a white foam.

Step 2: Saponification 140 mg (85 μmol) of the preceding product was dissolved in 5 ml of tetrahydrofuran. To this was added 4.5 ml (0.1N) of sodium hydroxide. The mixture was heated at 60° C. overnight. The solution was then acidified with a solution of hydrochloric acid (1M) and extracted 3 times with dichloromethane. The organic phase was dried over MgSO$_4$, filtered and evaporated under vacuum. Chromatography of the crude product over silica gel (elution: dichloromethane/methanol=50/1) yielded 115 mg (82%) of the product in the form of a white foam.

Step 3: Hydrogenolysis 66 mg (42 μmol) of the preceding product was dissolved in 2 ml of methanol and agitated under a dihydrogen atmosphere (1.4 bar) in the presence of Pd/C (10%) in a catalytic quantity so as to yield (I, R=connector) (29.3 mg, 83%), after lyophilization, in the form of an amorphous white powder (α/β 1/6 mixture at the level of the aglycone).

$^1$H-NMR (400 MHz, D$_2$O) of the product β-O-connector: δ 4.99 (bs, 1H, H-1A), 4.89 (bs, 1H, H-1B), 4.84 (bs, 1H, H-1C), 4.68 (bs, 1H, H-1D), 4.36 (d, 1H, $J_{2-3}$=3 Hz, H-2A), 4.28 (d, 1H, $J_{2-3}$=3.2 Hz, H-2C), 4.18 (d, 1H, $J_{2-3}$=3.19 Hz, H-2D), 4.11 (d, 1H, $J_{2-3}$=3.2 Hz, H-2B), 3.9–3.84 (m, 5H, H-6Ab, H-6Bb, H-6Cb, H-6Db and —O—CH—CH$_2$), 3.73–3.65 (m, 4H, H-6Aa, H-6Ba, H-6Ca, H-6Da), 3.63 (dd, 1H, $J_{3-2}$=3.19 Hz and $J_{3-4}$=9.7 Hz, H-3D), 3.62–3.57 (m, 2H, —O—CH—CH$_2$ and H-3C), 3.59 (dd, 1H, $J_{3-2}$=3 Hz and $J_{3-4}$=10.3 Hz, H-3A), 3.57 (dd, 1H, $J_{3-2}$=3.2 Hz and $J_{3-4}$=9.7 Hz, H-3B), 3.55 (t, 1H, $J_{4-3}$=$J_{4-5}$=10.3 Hz, H-4A), 3.51 (t, 1H, $J_{4-3}$=$J_{4-5}$=9.7 Hz, H-4B), 3.46 (t, 1H, $J_{4-2}$=$J_{4-5}$=9.7 Hz, H-4C), 3.44 (t, 1H, $J_{24-3}$=$J_{4-5}$=9.7 Hz, H-4D), 3.36–3.3 (m, 4H, H-5A, H-5B, H-5C and H-5D), 2.25 (t, 2H, $J_{CH2—CH2}$=7.4 Hz, —CH$_2$—COOH), 1.6–1.52 and 1.3–1.28 (m, 12H, —CH$_2$—).

$^{13}$C-NMR (100 MHz): δ 181.7 (COOH), 101.58, 101.46, 101.26, 100.32 (C-1A, C-1B, C-1C, C-1D), 79.5, 79.3, 78.7, 76.6, 76.5*, 73.2, 72.6, 72.3*2, 70.7, 67.8, 67.4, 67.2, 67.1, 61.5, 61.06, 61.02, 60.9 (20 CH ring), 70.4 (—O—CH$_2$—), 34 (—CH$_2$—CO$_2$H), 29, 28.7, 28.65, 28.6, 25.7, 25.5 (6 —CH$_2$—).

Mass spectrum (FAB) m/z calculated C$_{33}$H$_{58}$O$_{23}$Na: 845.32. Found 845.24.

10) 2-O-(2-O-(2-O-(3-O-benzyl-4,6-O-benzylidene-β-D-mannopyranosyl)-3-O-benzyl-4,6-O-benzylidene-β-D-mannopyranosyl)-3-O-benzyl-4,6-O-benzylidene-β-D-mannopyranosyl)-3-O-benzyl-4,6-O-benzlidene-D-mannopyranose (9)

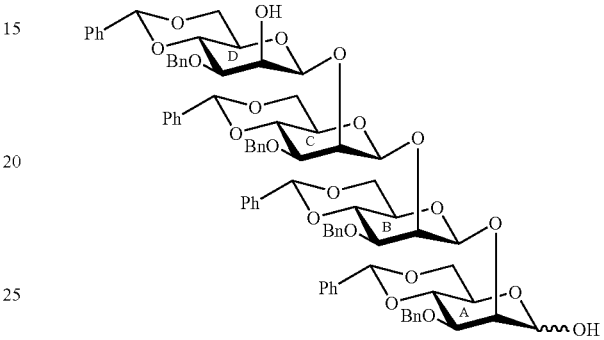

Step 1: Desilylation

For the experimental protocol, see step 1 of compound I (R=connector).

When 8 was treated with tetrabutylammonium fluoride it yielded phenyl 2-O-(2-O-(2-O-(3-O-benzyl-4,6-O-benzylidene β-D-mannopyranosyl)-3-O-benzyl-4,6-O-benzylidene-β-D-mannopyranosyl)-3-O-benzyl-4,6-O-benzylidene-β-D-mannopyranosyl)-3-O-benzyl-4,6-O-benzylidene-1-thio-α-D-mannopyranoside (202 mg, 92%) in the form of a white foam after silica gel chromatography (elution: cyclohexane/ethyl acetate=2.5/1) and after recrystallization in methanol.

m.p.: 133–136° C. (methanol); (α)$_D$ –42 (c 0.5, chloroform).

$^1$H-NMR (400 MHz, CDCl$_3$): δ 7.57–7.32 (m, 45H, arom.), 5.73, 5.71, 5.67 and 5.66 (4s, 4H, by), 5.64 (s, 1H, H-1A), 5.36 (s, 1H, H-1B), 4.92 (s, 1H, H-1D), 4.86 (d, 1H, $J_{gem}$=12.1 Hz, CHPh), 4.83 (d, 1H, $J_{gem}$=11.8 Hz, CHPh), 4.79 (s, 1H, H-1C), 4.78 (s, 2H, CH$_2$Ph), 4.77 (2d, 2H, 2CHPh), 4.71 (d, 1H, $J_{2-3}$=3.2 Hz, H-2A), 4.69 (d, 1H, $J_{gem}$=11.8 Hz, CHPh), 4.64 (d, 1H, $J_{gem}$=11.8 Hz, CHPh), 4.61 (d, 1H, $J_{2-3}$=3 Hz, H-2B), 4.53 (d, 1H, $J_{2-3}$=3.4 Hz, H-2C), 4.51–4.46 (m, 1H, H-5A), 4.47 (dd, 1H, $J_{6b-6a}$=10.3 Hz and $J_{6b-5}$=4.8 Hz, H-6Bb), 4.41–4.36 (m, 4H, H-6Ab, H-6Cb, H-6Db, H-2D), 4.36 (t, 1H $J_{4-3}$=$J_{4-5}$=9.7 Hz, H-4D), 4.32 (t, 1H, $J_{4-3}$=$J_{4-5}$=9.8 Hz, H-4B), 4.21 (t, 1H, $J_{4-3}$=$J_{4-5}$=9.7 Hz, H-4C), 4.13–4.11 (m, 2H, H-4A and H-3A), 4.08 (t, 1H, $J_{6a-6b}$=$J_{6a-5}$=10 Hz, H-6Ba), 3.98 (dd, 1H, $J_{6a-6b}$=10.4 and $J_{6a-5}$=9.7 Hz, H-6Ca), 3.95 (dd, 1H, $J_{6a-6b}$=10.1 and $J_{6a-5}$=9.7 Hz, H-6Da), 3.91 (t, 1H, $J_{6a-6b}$=$J_{6a-5}$=10.2 Hz, H-6Aa), 3.75 (dd, 1H, $J_{3-2}$=3.4 Hz and $J_{3-4}$=9.7 Hz, H-3C), 3.65 (dd, 1H, $J_{3-2}$=3 Hz and $J_{3-4}$=9.8 Hz, H-3B), 3.56 (ddd, 1H, $J_{5-4}$=9.8 Hz and $J_{5-6b}$=4.8Hz and $J_{5-6a}$=9.8 Hz, H-5B), 3.53 (dd, 1H, $J_{3-2}$=3.1 Hz and $J_{3-4}$=9.6 Hz, H-3D), 3.44 (ddd, 1H, $J_{5-4}$=9.7 Hz and $J_{5-6b}$=9.7 Hz and $J_{5-6a}$=4.7 Hz, H-5C), 3.35 (ddd, 1H, $J_{5-4}$=9.7 Hz and $J_{5-6b}$=9.7 Hz and $J_{5-6a}$=4.9 Hz, H-5D), 3.28 (bs, 1H, OH).

$^{13}$C-NMR (100 MHz): δ 138.2*2, 137.9, 137.8, 137.5, 137.2, 137.04, 136.08, 133.05 (9 C arom.), 131.5–125.9)45

CH arom.), 102.1 (CH by), 101.5 (CH by), 101.48 (C-1D), 101.26 (CH by), 101.15 (CH by), 101 (C-1B), 98.2 (C-1C), 85.14 (C-1A), 78.98 (C-4A), 78.4 (C-4D), 78 (C-4B), 77.98 (C-4C), 77.7 (C-3B), 76.9 (C-3D), 75.3 (C-3C), 74.6 (C-3A), 74.4 (C-2A), 74.3 (C-2C), 74.1 (C-2B), 72.4 (CH$_2$Ph), 71.8*2 (CH$_2$Ph), 71 (CH$_2$Ph), 68.9 (C-2D), 68.6 (C-6D), 68.5 (C-6A), 68.4 (C-6B), 68.25 (C-6C), 67.8 (C-5B and C-5C), 66.8 (C-5D), 64.9 (C-5A).

Mass spectrum: m/z 1488 (M+NH$_4$)$^+$.

Analysis for C$_{86}$H$_{86}$O$_{20}$S.1CH$_3$OH (1503.67): calculated=C: 69.49 H: 6.03; found=C: 69.28 H: 5.92.

Step 2: Hydrolysis of the Thiophenyl 175 mg (119 μmol, 1 eq) of the preceding compound was dissolved in a mixture of solvents (acetone/water=4.5 ml/0.5 ml). The mixture was cooled to 0° C. We then added 106 mg (0.595 mmol, 5 eq) of N-bromosuccinimide. A solution of sodium bicarbonate was poured into the flask after 30 min of agitation at 0° C. The acetone was then evaporated under vacuum. The residue was taken up with dichloromethane, washed with a sodium thiosulfate solution and an aqueous solution of NaCl. The organic phase was then dried over magnesium sulfate, filtered and evaporated. The crude product was chromatographed over silica gel (elution: cyclohexane/ethyl acetate=1.8/1 and then 1.5/1) and yielded 138 mg (yield=84%) of compound 9 of a mixture of α/β configuration (2.6/1) in the form of a white foam.

$^1$H-NMR (400 MHz, CDCl$_3$) of the product α-OH: δ 5.52 (s, 1H, H-1B), 5.22 (bs, 1H, J$_{1-OH}$=3 Hz, H-1A), 4.78 (s, 1H, H-1D), 4.63 (s, 1H, H-1C).

$^{13}$C-NMR (100 MHz): δ 101.7 (C-1D), 101.1 (C-1B), 99.2 (C-1C), 92.09 (C-1A) and disappearance of the characteristic peak at 85.14 of C-1A possessing a thiophenol as aglycone.

Mass spectrum: m/z 1396.8 (M+NH$_4$)$^+$.

Analysis for C$_{80}$H$_{82}$O$_{21}$ (1379.529: calculated=C: 69.65 H: 5.99; found=C: 69.46 H: 6.11).

11) 2-O-(2-O-(2-O-(β-D-mannopyranosyl)-β-D-mannopyranosyl-β-D-mannopyranosyl)-β-D-mannopyranose (I, R=H)

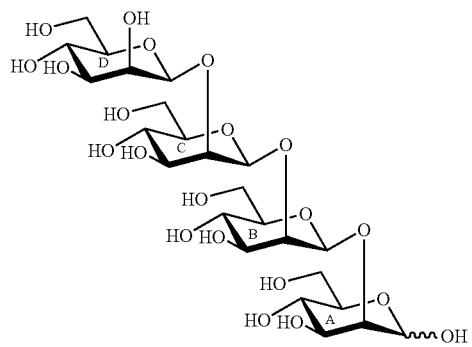

For the experimental protocol, see step 2 of compound I (R=connector).

111.4 mg (80.7 μmol) of compound 9 yielded 46 mg (85%) of compound I (R=H) after lyophilization in the form of an amorphous powder.

$^1$H-NMR (400 MHz, D$_2$O) of the product α-OH: δ 5.24 (d, 1H, J$_{1-2}$=1.64 Hz, H-1B), 4.39 (d, 1H, J$_{2-3}$=3.2 Hz, H-2C), 4.22 (d, 1H, J$_{2-3}$=3.27 Hz, H-2B), 4.11 (d, 1H, J$_{2-3}$=3.1 Hz, H-2D), 4.08 (dd, 1H, J$_{2-1}$=1.64 Hz and J$_{2-3}$=3.02 Hz, H-2A).

$^{13}$C-NMR (100 MHz): δ 101.53, 101.29, 99.46, 92.4 (C-1A, C-1B, C-1C, C-1D), 79.7, 79, 78.7, 76.6, 76.5, 76.4, 73.2, 72.67, 72.5, 72.2, 70.7, 69.4, 67.7, 67.4, 67.26, 67.1, 61.5, 61.1, 60.84, 60.7 (20 CH ring).

Mass spectrum (FAB) m/z: calculated C$_{24}$H$_{42}$O$_{21}$Na: 689.21; obtained: 689.32.

EXAMPLE 2

Preparation of D-Man α(1-2) D-Man α(1-2) D-α(1-2) D-Man of formula (II)

I-Reaction Diagram

Figure 2:
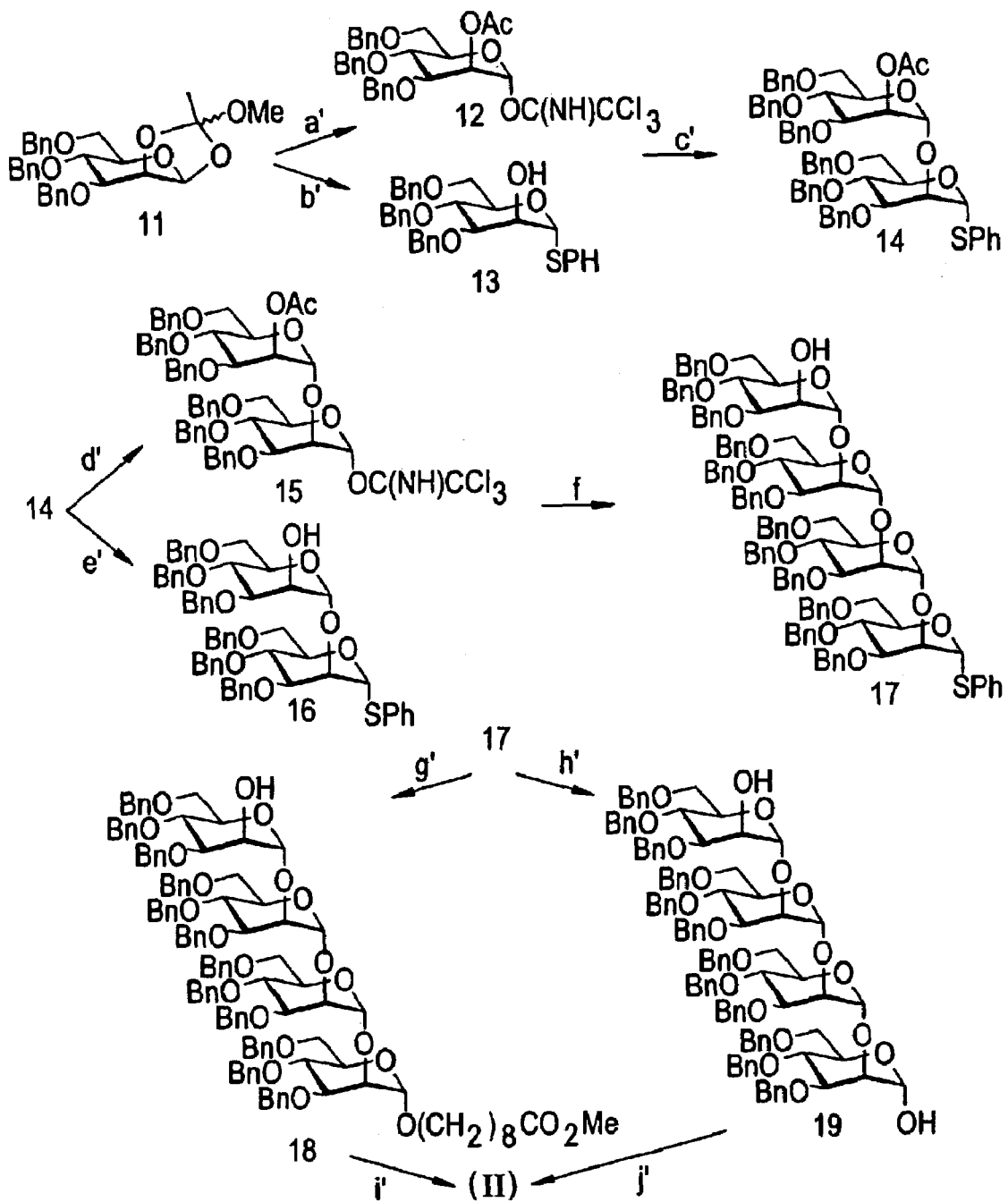
FIG. 2 is a reaction diagram for the preparation of D-Man α(1-2) D-Man α(1-2) D-Man α(1-2) D-Man of formula (II).

FIG. 2 is a reaction diagram for preparing D-Man α(1-2) D-Man α(1-2) D-Man α(1-2) D-Man of formula (II). As was the case in Example 1, a block strategy was used. A thiophenyl group intermediately protected the anomer carbon. Depending on the reaction performed, compound 11 yields compound 12 or 13, which are condensed into the disaccharide 14.

Reaction (a') was performed under the following conditions: CH$_3$COOH, H$_2$O (80/20) and then CCl$_3$CN, DBU, CH$_2$Cl$_2$, 0C.

Reaction (b') was performed under the following conditions: PhSH, HgBr$_2$. CH$_3$CN, 80° C. and then CH$_3$ONa, CH$_3$OH.

Reaction (c') was performed under the following conditions: TMSOTf, 4-Angstrom molecular sieve, CH$_2$Cl$_2$.

The disaccharide 14 was transformed into the disaccharides 15 and 16, which were condensed to yield the key tetrasaccharide 17.

Reaction (d') was performed under the following conditions: NBS, water, acetone, then CCl$_3$CN, DBU, CH$_2$Cl$_2$.

Reaction (e') was performed under the following conditions: MeONa, MeOH.

Reaction (f') was performed under the following conditions: 1) BF$_3$, Et$_2$O, 5-Angstrom molecular sieve, CH$_2$Cl$_2$; 2) MeONa/MeOH.

The key tetrasaccharide 17 is or is not functionalized into one of compounds 18 or 19 and then provides deprotection of the tetramannoside of formula (II) in which R is H or —(CH$_2$)$_8$—CO$_2$Me.

Reaction (g') was performed under the following conditions: NBS, TfOH, 8-methoxycarbonyloctanol, 4-Angstrom molecular sieve, CH$_2$Cl$_2$, −15° C.

Reaction (h') was performed under the following conditions: NBS, water, acetone.

Reaction (i') was performed under the following conditions: 1-NaOH, THF, water, 2-H$_2$, Pd/C, MeOH.

Reaction (j') was performed under the following conditions: H$_2$, Pd/C, MeOH.

II-Experimental Protocol

Compounds 12 (F. Yamazaki, S. Sato, T. Nukuda, Y. Ito, T. Ogawa, Carbohydr. Res., 201 (1990) 31–50) and 13 (Y.-M. Zhang, J.-M. Mallet, P. Sinaÿ, Carbohydr. Res. 236 (1992), 73–88) were prepared according to the literature from the orthoester 11 (N. E. Franks, R. Montgomery, *Carbohydr. Res.* 6 (1968) 286–98).

1) Phenyl 2-O-(2-O-acetyl-3,4,6-tri-O-benzyl-α-D-mannopyranosyl)-3,4,6-tri-O-benzyl-1-thio-α-D-mannopyranoside (14)

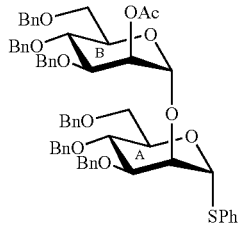

A mixture of 12 (F. Yamazaki, S. Sato, T. Nukuda, Y. Ito, T. Ogawa, *Carbohydr. Res.*, 201 (1990) 31–50) (9.7 g, 15.24 mmol, 1.2 eq) 13 (Y.-M. Zhang, J.-M. Mallet, P. Sinaÿ, *Carbohydr. Res.*, 236 (1992) 73–88) (6.88 g, 12.7 mmol, 1 eq) and 17 g of 4-Å molecular sieve in powder form in 100 ml of anhydrous dichloromethane was agitated under an argon atmosphere. After 30 min of agitation, the reactional medium was cooled to −10° C. Trimethylsilyl trifluoromethanesulfonate (0.44 ml, 1.9 mmol, 0.15 eq) was then added. After 30 min, the solution was neutralized with an aqueous solution of sodium bicarbonate. The organic phase was then washed with a brine solution, dried over magnesium sulfate, filtered and concentrated. Chromatography of the crude product over silica gel (elution: cyclohexane/ethyl acetate=6/1) yielded 14 (9.3 g, 72%) in the form of a colorless syrup. $(\alpha)_D$ +93 (c 0.55, chloroform).

$^1$H-NMR (400 MHz, CDCl$_3$): δ 7.48–7.25 (m, 35H, arom.), 5.69 (d, 1H, $J_{1-2}$=1.62 Hz, H-1A), 5.58 (dd, 1H, $J_{2-1}$=1.7 Hz and $J_{2-3}$=3.3 Hz, H-2B), 5.13 (d, 1H, $J_{1-2}$=1.7 Hz, H-1B), 4.94 (d, 1H, $J_{gem}$=10.8 Hz, CHPh), 4.87 (d, 1H, $J_{gem}$=10.8 Hz, CHPh), 4.79 (d, 1H, $J_{gem}$=11.8 Hz, CHPh), 4.75 (d, 1H, $J_{gem}$=11.8 Hz, CHPh), 4.71 (d, 1H, $J_{gem}$=11.8 Hz, CHPh), 4.71 (d, 1H, $J_{gem}$=10.9 Hz, CHPh), 4.69 (d, 1H, $J_{gem}$=12 Hz, CHPh), 4.64 (d, 1H, $J_{gem}$=10.8 Hz, CHPh), 4.6 (d, 1H, $J_{gem}$=12.3 Hz, CHPh), 4.52 (d, 1H, $J_{gem}$=12 Hz, CHPh), 4.47 (d, 1H, $J_{gem}$=10.8 Hz, CHPh), 4.45 (d, 1H, $J_{gem}$=10.9 Hz, CHPh), 4.43 (d, 1H, $J_{gem}$=12.3 Hz, CHPh), 4.33 (ddd, 1H, $J_{5-4}$=9.3 Hz, $J_{5-6a}$=1.7 Hz and $J_{5-6b}$=5.2 Hz, H-5A), 4.28 (dd, 1H, $J_{2-1}$=1.62 Hz and $J_{2-3}$=2.8 Hz, H-2A), 4.03 (dd, 1H, $J_{3-2}$=3.3 Hz and $J_{3-4}$=9.4 Hz, H-3B), 4.03–3.97 (m, 1H, H-5B), 3.99 (t, 1H, $J_{4-3}$=$J_{4-5}$=9.3 Hz, H-4A), 3.94 (dd, 1H, $J_{3-2}$=2.8 Hz and $J_{3-4}$=9.3 Hz, H-3A), 3.88 (t, 1H, $J_{4-3}$=$J_{4-5}$=9.4 Hz, H-4B), 3.88 (dd, 1H, $J_{6b-6a}$=11.1 and $J_{6b-5}$=5.2 Hz, H-6Ab), 3.77 (dd, 1H, $J_{6b-6a}$=11.1 Hz and $J_{6b-5}$=1.7 Hz, H-6Aa), 3.74 (dd, 1H, $J_{6b-6a}$=10.6 Hz and $J_{6b-5}$=4.5 Hz, H-6Bb), 3.77 (dd, 1H, $J_{6b-6a}$=10.6 Hz and $J_{6b-5}$=1.7 Hz, H-6Ba), 2.19 (s, 3H, —C:O—OCH$_3$).

$^{13}$C-NMR (100 MHz): δ 170.2 (—C:O—OCH$_3$), 138.4, 138.3, 138.27, 138, 137.98, 137.9, 131.6 (7 C arom.), 129–127.3 (35 CH arom.), 99.7 ($^1J_{CH}$=169.2 Hz, C-1B), 87.1 ($^1J_{CH}$=168.8 Hz), C-1A), 79.89 (C-3A), 78 (C-3B), 76.6 (C-2A), 75.2 (CH$_2$Ph), 75 (CH$_2$Ph), 74.7 (C-4A), 74.3 (C-4B), 73.1 (2 CH$_2$Ph), 72.8 (C-5A), 72.2 (CH$_2$Ph), 71.9 (CH$_2$Ph), 71.9 (C-5B), 69.1 (C-6A), 68.7 (C-2B), 68.5 (C-6B), 21.1 (—C:O—OCH$_3$).

Mass spectrum: m/z 1034.4 (M+NH4)$^+$.

Analysis for C$_{62}$H$_{64}$O$_{11}$S (1017.256): calculated=C: 73.20 H: 6.35; found=C: 72.98 H: 6.65.

2) O-[2-O-(2-O-acetyl-3,4,6-tri-O-benzyl-α-D-mannopyranosyl)-3,4,6-tri-O-benzyl-α-D-mannopyranosyl and β-D-mannopyranosyl]trichloroacetimidate (15)

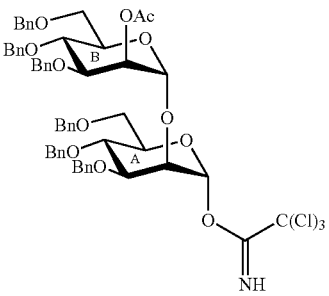

Compound 14 (3 g, 2.95 mmol, 1 eq) was dissolved in 150 ml of 95/5 acetone/water mixture. To this solution we added 2.6 g (11.8 mmol, 4 eq) of N-bromosuccinimide. After 15 min of agitation, a solution of sodium bicarbonate was added and the acetone evaporated under vacuum. The residue was taken up with dichloromethane and washed with a brine solution. Flash chromatography over silica gel of the crude product yielded 2.37 g (yield=87%) of the free OH product in reducing position in the form of a colorless oil. This oil was dissolved in 10 ml of anhydrous dichloromethane. We then added 3.08 ml (12 eq) of trichloroacetonitrile and cooled the solution to 0° C.; we then added 115 μl (0.3 eq) of 1.8-diazabicylco[5.4.0]undec-7-ene to the medium. After 20 min, the solution was injected directly onto a silica gel (elution: cyclohexane/ethyl acetate=3/1) and 2.2 g (yield=81% over the two steps) of compound 15α very majority (α/β=92/8) was thereby obtained in the form of a colorless oil.

$^1$H-NMR (400 MHz, CDCl$_3$) of the product α-O-imidate: δ 8.55 (s, 1H, C=NH), 7.39–7.25 (m, 30H, arom.), 6.36 (d, 1H, $J_{1-2}$=1.95 Hz, H-1A), 5.67 (dd, 1H, $J_{2-1}$=1.6 Hz and $J_{2-3}$=3.4 Hz, H-2B), 5.2 (d, 1H, $J_{1-2}$=1.6 Hz, H-1B), 4.95 (d, 1H, $J_{gem}$=10.6 Hz, CHPh), 4.89 (d, 1H, $J_{gem}$=10.8 Hz, CHPh), 4.81 (d, 1H, $J_{gem}$=11.9 Hz, CHPh), 4.75 (d, 1H, $J_{gem}$=12 Hz, CHPh), 4.73 (d, 1H, $J_{gem}$=11.9 Hz, CHPh), 4.71 (d, 1H, $J_{gem}$=10.8 Hz, CHPh), 4.7 (d, 1H, $J_{gem}$=12.6 Hz, CHPh), 4.65 d, 1H, $J_{gem}$=10.6 Hz, CHPh), 4.55 (d, 1H, $J_{gem}$=12.6 Hz, CHPh), 4.52 (d, 1H, $J_{gem}$=12 Hz), 4.51 (d, 1H, $J_{gem}$=10.8 Hz, CHPh), 4.45 (d, 1H, $J_{gem}$=10.8 Hz, CHPh), 4.13 (dd, 1H, $J_{2-1}$=1.95 Hz and $J_{2-3}$=3.3 Hz, H-2A), 4.09 (t, 1H, $J_{4-3}$=$J_{4-5}$=9.7 Hz, H-4A), 4.08–3.97 (m, 5H, H-5A, H-5B, H-3A, H-3B and H-4B), 3.89 (dd, 1H, $J_{6b-6a}$=11.5 Hz and $J_{6b-5}$=3.6 Hz, H-6Ab), 3.86 (dd, 1H, $J_{6b-6a}$=11.6 Hz and $J_{6b-5}$=4.1 Hz, H-6Bb), 3.78 (dd, 1H, $J_{6b-6a}$=11.5 Hz and $J_{6b-5}$=1.1 Hz, H-6Aa), 3.75 (dd, 1H, $J_{6b-6a}$=11.6 Hz and $J_{6b-5}$=1 Hz, H-6Ba, 2.2 (s, 3H, —C:O—OCH$_3$).

$^{13}$C-NMR (100 MHz): δ 170.25 (—C:O—OCH$_3$), 159.98 (—C=NH), 138.4 138.3, 138.15, 138.07, 137.9, 137.88 (6 C arom.), 128.4–127.4 (30 CH arom., 99.5 (C-1B), 96.7

(C-1A), 78.5 (C-3A), 78.1 (C-3B), 75.4 (CH$_2$Ph), 75.1 (CH$_2$Ph), 74.7 (C-5B), 74.1 (C-4B), 73.8 (C-4A), 73.3 (CH$_2$Ph), 73.2 (CH$_2$Ph), 73 (C-2A), 72.4 (CH$_2$Ph), 71.97 (CHPh), 71.9 (C-5A), 68.62 (C-2B), 68.58 (C-6B), 68.51 (C-6A), 21.15 ( C:O—OCH$_3$).

No elemental analysis was performed on these poorly stable compounds.

3) Phenyl 2-O-(3,4,6-tri-O-benzyl-α-D-mannopyranosyl)-3,4,6-tri-O-benzyl-1-thio-α-D-mannopyranoside (16)

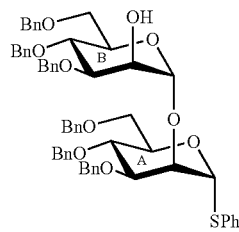

Compound 14 (6 g, 5.9 mmol) was dissolved in 40 ml of a toluene/methanol (1/1) mixture. We then added sodium (cat.). After 15 min, the solution was neutralized with Amberlite resin IR 120 (H+), filtered and concentrated. Silica gel chromatography (elution: cyclohexane/ethyl acetate=3/1) of the crude product yielded 16 (5.45 g, 95%) in the form of a colorless syrup.

$(\alpha)_D$ +93.6 (c 0.51, chloroform).

$^1$H-NMR (400 MHz, CDCl$_3$): δ 7.5–7.2 (m, 35H, arom.), 5.76 (d, 1H, $J_{1-2}$=1.6 Hz, H-1A), 5.22 (d, 1H, $J_{1-2}$=1.6 Hz, H-1B), 4.95 (d, 1H, $J_{gem}$=10.7 Hz, CHPh), 4.85 (d, 1H, $J_{gem}$=10.9 Hz, CHPh), 4.77 (s, 2H, CH$_2$Ph), 4.75 (d, 1H, $J_{gem}$=12 Hz, CHPh), 4.66 (d, 1H, $J_{gem}$=10.7 Hz, CHPh), 4.65 (d, 1H, $J_{gem}$=11.3 Hz, CHPh), 4.6 (d, 1H, $J_{gem}$=11.3 Hz, CHPh), 4.57 (d, 1H, $J_{gem}$=12.4 Hz, CHPh), 4.55 (d, 1H, $J_{gem}$=12 Hz, CHPh), 4.52 (d, 1H, $J_{gem}$=10.9 Hz, CHPh), 4.45 (d, 1H, $J_{gem}$=12.4 Hz, CHPh), 4.37–4.33 (m, 1H, H-5A), 4.34 (dd, 1H, $J_{2-1}$=1.6 Hz and $J_{2-3}$=2.7 Hz, H-2A), 4.21–4.18 (m, 1H, H-2B), 4.01 (t, 1H, $J_{4-3}$=$J_{4-5}$=9.3 Hz, H-4A, 4.03–3.98 (m, 1H, H-5B), 3.96 (Boeuf Bourguignon, 1H, $J_{3-2}$=2.7 Hz and $J_{3-4}$=9.3 Hz, H-3A), 3.95 (dd, 1H, $J_{6b-6a}$=11.2 Hz and $J_{6b-5}$=4.6 Hz, H-6Ab), 3.93 (dd, 1H, $J_{3-2}$=3.1 Hz and $J_{3-4}$=9.4 Hz, H-3B), 3.87 (t, 1H, $J_{4-3}$=$J_{4-5}$=9.4 Hz, H-4B), 3.8 (dd, 1H, $J_{6b-6a}$=11.2 Hz and $J_{6b-5}$=1.6 Hz, H-6Aa), 3.71 (dd, 1H, $J_{6b-6a}$=10.6 Hz and $J_{6b-5}$=4.9 Hz, H-6Bb), 3.64 (dd, 1H, $J_{6b-6a}$=10.6 Hz, and $J_{6b-5}$=1.9 Hz, H-6Ba), 2.53 (d, 1H, $J_{OH-2}$=1.6 Hz, OH).

$^{13}$C-NMR (100 MHz): δ 138.5, 138.3, 138.2, 138, 137.9, 137.86, 131.5 (7 C arom.), 128.9–127.3 (35 CH arom.), 101.2 (C-1B), 87.2 (C-1A), 79.99 (C-3A), 79.9 (C-3B), 76.5 (C-2A), 75.1 (CH$_2$Ph), 75 (CH$_2$Ph), 74.8 (C-4A), 74.2 (C-4B), 73.13 (CH$_2$Ph), 73.1 (CH$_2$Ph), 72.8 (C-5A), 72.3 (CH$_2$Ph), 72.1 (CH$_2$Ph), 71.6 (C-5B), 69.1 (C-6A), 68.5 (C-6B), 68.47 (C-2B).

Mass spectrum: m/z 992/6 (M+NH4)$^+$.

Analysis for C$_{60}$H$_{62}$O$_{10}$S (975.218): calculated=C: 73.78 H: 6.408; found=C: 74.15 H: 6.90.

4) Phenyl 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-O-benzyl-1-thio-α-D-mannopyranoside (17)

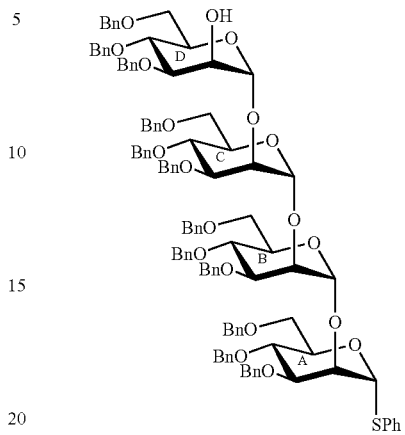

A mixture of 16 (200 mg, 187 μmol, 1 eq), 15 (364 mg, 374 μmol, 2 eq), 600 mg of 4-Å molecular sieve in 6 ml of anhydrous dichloromethane was agitated for 30 min under an argon atmosphere and cooled to −10° C. We then added 71 μl (3 eq) boron trifluoride etherate. After 40 min at −10° C., the mixture was neutralized with a solution of sodium bicarbonate. After filtration on a Celite bed, the organic phase was washed with a brine solution, dried over magnesium sulfate, filtered and concentrated under vacuum. The residue was chromatographed (elution: cyclohexane/ethyl acetate=6/1) and yielded 211 mg (yield=60%) of a colorless oil. The $^1$H-NMR analysis revealed the presence of two products, one of stereochemistry α at the level of the newly created bond and the other β. Unfortunately, it was not possible to separate these products by silica gel chromatography. The mixture was then dissolved in a toluene/methanol mixture to which sodium (cat.) was added. After 15 min, the solution was neutralized with Amberlite resin IR 120 (H+), filtered and evaporated under vacuum. The residue was chromatographed (elution: cyclohexane/ethyl acetate=5/1) and yielded product 17 (153 mg, 71%).

Characteristics of 17: $(\alpha)_D$ +48.7 (c 0.36, chloroform).

$^1$H-NMR (400 MHz, CDCl$_3$): δ 7.51–7.23 (m, 60H, arom.), 5.83 (d, 1H, $J_{1-2}$=1.4 Hz, H-1A), 5.35 (d, 1H, $J_{1-2}$=1.4 Hz, H-1B or H-1C), 5.3 (d, 1H, $J_{1-2}$=1.6 Hz, H-1B or H-1C), 5.21 (d, 1, $J_{1-2}$=1.5 Hz, H-1D), 4.91 (d, 1H, $J_{gem}$=10.7 Hz, CHPh), 4.9 (d, 1H, $J_{gem}$=10.9 Hz, CHPh), 4.89 (d, 1H, $J_{gem}$=10.6 Hz, CHPh), 4.84 (d, 1H, $J_{gem}$=10.8 Hz, CHPh), 4.71 (2d, 2H, $J_{gem}$=12.2 Hz, 2 CHPh), 4.69 (d, 1H, $J_{gem}$=11.3 Hz, CHPh), 4.67 (d, 1H, $J_{gem}$=11.3 Hz, CHPh), 4.65 (s, 2H, CH$_2$Ph), 4.64 (d, 1H, $J_{gem}$=11.3 Hz, CHPh), 4.61 (d, 1H, $J_{gem}$=10.9 Hz, CHPh), 4.59 (d, 1H, $J_{gem}$=12.3 Hz, CHPh), 4.56 (3d, 3H, 3 CHPh), 4.54 (d, 1H, $J_{gem}$=12.2 Hz, CHPh), 4.53 (d, 1H, $J_{gem}$=11.3 Hz, CHPh), 4.51 (d, 1H, $J_{gem}$=10.8 Hz, CHPh), 4.49 (d, 1H, $J_{gem}$=11.9 Hz, CHPh), 4.47 (d, 1H, $J_{gem}$=12.2 Hz, CHPh), 4.46 (d, 1H, $J_{gem}$=12.8 Hz, CHPh), 4.36 (d, 1H, $J_{gem}$=11.9 Hz, CHPh), 4.36–4.34 (m, 2H, H-2A and H-5A, B, C or D), 4.24 (d, 1H, $J_{gem}$=12.3 Hz, CHPh), 4.21 (m, 1H, H-2D), 4.19 (dd, 1H, $J_{2-1}$=1.6 Hz and $J_{2-3}$=2.4 Hz, H-2B or H-2C), 4.17 (dd, 1H, $J_{2-1}$=1.4 Hz and $J_{2-3}$=2.4 Hz, H-2B or H-2C), 4.04–3.95 (m, 6H, H-3D, H-3B or H-3C, H-4A, B, C or D, 3*H-5A, B, C or D), 3.97–3.88 (m, 4H, H-3A, H-3B or H-3C and 2*H-4A, B, C or D), 3.83–3.56 (m, 5H, H-4A, B, C or D, H-6A, H-6B, H-6C and H-6D), 2.47 (d, 1H, $J_{OH-2}$=2.25 Hz, OH).

$^{13}$C-NMR (100 MHz): δ 138.47*2, 138.44, 138.4*2, 138.32*2, 138.29, 138.2, 138.05, 138, 137.9, 134.2 (13 C arom.), 128.8–127.2 (60 CH arom.), 101.4 (C-1B or C-1C, $^1J_{CH}$=171.7 Hz or $^1J_{CH}$=170.9 Hz), 101 (C-1B or C-1C or C-1D, $^1J_{CH}$=171.7 Hz or $^1J_{CH}$=170.9 Hz), 87.1 (C-1A, $^1J_{CH}$=169.1 Hz), 80, 79.6, 79.4, 79 (4*C-3), 77.3 (C-2A), 75.5 (C-2B or C-2C), 75.1 (CH$_2$Ph), 75.07 (C-2B or C-2C), 74.94 (CH$_2$Ph), 74.85*2, 74.77, 72 (4*C-4), 73.26 (CH$_2$Ph), 73.18 (CH$_2$Ph), 73.1 (CH$_2$Ph), 72.8 (CH$_2$Ph), 72.6, 72.26, 72.22, 71.5 (4*C-5), 72.3 (CH$_2$Ph), 72 (CH$_2$Ph), 71.8 (CH$_2$Ph), 69.4, 69.2, 68.9, 68.7 (4*C-6), 68.4 (C-2D).

Mass spectrum: m/z 1861.9 (M+Na)$^+$.

Analysis for $C_{114}H_{118}O_{20}S$ (1840.258): calculated=C: 74.4 H: 6.463; found=C: 74.3 H: 6.54.

5) 8-methoxycarbonyloctyl 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-O-benzyl-α-D-mannopyranoside (18a) and 8-methoxycarbonyloctyl 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-O-benzyl-β-D-mannopyranoside (18b)

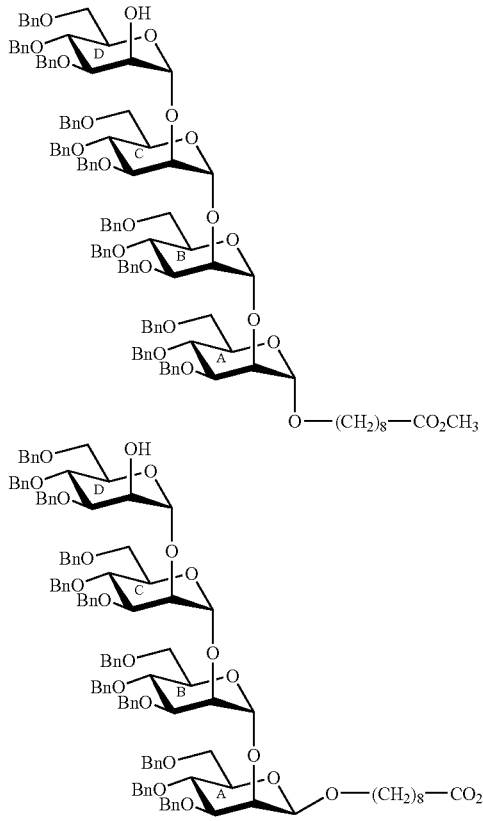

For the experimental protocol, see compound 10.

From 268 mg (146 μmol) of compound 17, we obtained the two diastereoisomers α-O-connector 18a (101 mg, 36%) and β-O connector 18b (100 mg, 36%) after chromatography over silica gel (elution: cyclohexane/ethyl acetate=4/1) in an α/β ratio of 1/1.

Characteristic of α-O connector 18a: (α)$_D$ +35 (c 0.2, chloroform).

$^1$H-NMR (400 MHz, CDCl$_3$): δ 7.36–7.23 (m, 55H, arom.), 5.3 (d, 1H, $J_{1-2}$=1.2 Hz, H-1B or H-1C), 5.27 (d, 1H, $J_{1-2}$=1.6 Hz, H-1B or H-1C), 5.18 (d, 1H, $J_{1-2}$=1.4 Hz, H-1D), 4.99 (d, 1H, $J_{1-2}$=1.4 Hz, H-1A), 4.89 (2d, 2H, $J_{gem}$=10.9 Hz, 2 CHPh), 4.86 (d, 1H, $J_{gem}$=10.9 Hz, CHPh), 4.82 (d, 1H, $J_{gem}$=10.5 Hz, CHPh), 4.72 (2d, 2H, 2 CHPh), 4.67 (d, 1H, $J_{gem}$=12.2 Hz, CHPh), 4.63–4.58 (m, 8H, 8 CHPh), 4.56 (d, 1H, $J_{gem}$=12.3 Hz, CHPh), 4.55 (d, 1H, $J_{gem}$=10.9 Hz, CHPh), 4.54 (d, 1H, $J_{gem}$=10.9 Hz, CHPh), 4.49 (d, 1H, $J_{gem}$=10.5 Hz, CHPh), 4.48 (d, 1H, $J_{gem}$=11.5 Hz, CHPh), 4.47 (d, 1H, $J_{gem}$=11.2 Hz, CHPh), 4.4 (d, 1H, $J_{gem}$=12.2 Hz, CHPh), 4.35 (d, 1H, $J_{gem}$=11.5 Hz, CHPh), 4.21 (d, 1H, $J_{gem}$=12.3 Hz, CHPh), 4.2–4.19 (m, 1H, H-2D), 4.185 (dd, 1H, $J_{2-1}$=1.6 Hz and $J_{2-3}$=2.5 Hz, H-2B or H-2C), 4.15 (dd, 1H, $J_{2-1}$=1.2 Hz and $J_{2-3}$=2.1 Hz, H-2B or H-2C), 4.03 (dd, 1H, $J_{2-1}$=1.4 Hz and $J_{2-3}$=2.5 Hz, H-2A), 4.01–3.89 (m, 9H, 4*H-3, 3*H-5A, B, C or D, 2*H-4A, B, C or D), 3.84–3.72 (m, 5H, 2*H-4A, B, C or D, 1*H-5A, B, C or D, 2*H-6A, B, C or D), 3.71 (s, 3H, —C:O—OCH$_3$), 3.67–3.51 (m, 2H, 2*H-6A, B, C or D), 3.60 (dt, 1H, $J_{CH-CH2}$=6.8 Hz and $J_{gem}$=9.5 Hz, —O—CH—CH$_2$—), 3.28 (dt, 1H, $J_{CH-CH2}$=6.6 Hz and $J_{gem}$=9.5 Hz, —O—CH—CH$_2$—), 2.44 (br, 1H, OH), 2.34 (t, 2H, $J_{3-2}$=7.6 Hz, —CH$_2$C:O—OCH$_3$), 1.69–1.62 (m, 2H, —CH$_2$—), 1.55–1.48 (m, 2H, —CH$_2$—), 1.37–1.27 (m, 8H, —(CH$_2$)$_4$—).

$^{13}$C-NMR (100 MHz): δ 174.2 (—C:O—OCH$_3$), 138.6, 138.55, 138.5*4, 138.44, 138.36*2, 138.3, 138.1, 138 (12 C arom.), 128.4–127.26 (55 CH arom.), 101.1 (C-1B or C-1C, $^1J_{CH}$=171.7 Hz or $^1J_{CH}$=172.9 Hz), 100.9 (C-1B or C-1C and C-1D, $^1J_{CH}$=171.7 Hz or $^1J_{CH}$=172.9 Hz), 98.7 (C-1A, $^1J_{CH}$=168.5 Hz), 80, 79.4*2, 79.1 (4*C-3), 75.8 (C-2A), 75.6 (C-2B or C-2C), 75.13 (C-2B or C-2C), 75.1 (2*CH$_2$Ph), 74.96 (CH$_2$Ph), 73.9*2, 74.8, 74.3 (4*C-4), 73.3 (CH$_2$Ph), 73.2 (CH$_2$Ph), 73.18 (2*CH$_2$Ph), 72.33 (2*CH$_2$Ph), 72.3, 72, 71.76, 71.73 (4*C-5), 72 (CH$_2$Ph), 71.76 (CH$_2$Ph), 71.73 (CH$_2$Ph), 69.6, 69.5, 63.35, 68.8 (4*C-6), 68.5 (C-2D), 67.65 (—O—CH$_2$—), 69.8 (CH$_2$Ph), 51.4 (—C:O═OCH$_3$), 34 (—CH$_2$—C:O—O—CH$_3$), 29.4, 29.2, 29.1, 29, 26, 24.9 (—CH$_2$—).

Mass spectrum: m/z 1934.8 (M+NH4)$^+$.

Analysis for $C_{118}H_{132}O_{23}$ (1918.35): calculated=C: 73.88 H: 6.93; found=C: 73.76 H: 7.12.

Characteristic of β-O connector 18b: (α)$_D$ +2 (c 0.2, chloroform).

$^1$H-NMR (400 MHz, CDCl$_3$): δ 7.38–7.25 (m, 55H, arom.), 5.39 (d, 1H, $J_{1-2}$=1.5 Hz, H-1B or H-1C), 5.34 (d, 1H, $J_{1-2}$=1.5 Hz, H-1B or H-1C), 5.23 (d, 1H, $J_{1-2}$=1.45 Hz, H-1D), 4.9 (d, H, $J_{gem}$=10.6 Hz, CHPh), 4.89 (d, 1H, $J_{gem}$=10.9 Hz, CHPh), 4.87 (d, 1H, $J_{gem}$=10.6 Hz, CHPh), 4.82 (d, H, $J_{gem}$=12.3 Hz, CHPh), 4.81 (d, 1H, $J_{gem}$=10.1 Hz, CHPh), 4.79 (d, 1H, $J_{gem}$=11.5 Hz, CHPh), 4.69 (d, 1H, $J_{gem}$=12.2 Hz, CHPh), 4.68–4.55 (m, 11H, 11 CHPh), 4.54 (d, 1H, $J_{gem}$=11.7 Hz, CHPh), 4.52 (d, 1H, $J_{gem}$=10.6 Hz, CHPh), 4.51 (d, 1H, $J_{gem}$=11.5 Hz, CHPh), 4.48 (d, 1H, $J_{gem}$=10.1 Hz, CHPh), 4.41–4.38 (m, 1H, H-5B or H-5C), 4.38 (d, 1H, $J_{gem}$=12.2 Hz, CHPh), 4.3 (s, 1H, H-1A), 4.27 (d, 1H, $J_{gem}$=12.4 Hz, CHPh), 4.25–4.24 (m, 2H, H-2B and H-2C), 4.2–4.19 (m, 1H, H-2D), 4.13 (d, 1J, $J_{2-3}$=2.3 Hz, H-2A), 4.09 (dd, 1H, $J_{3-2}$=2.8 Hz and $J_{3-4}$=9.6 Hz, H-3B or H-3C), 4.05 (dd, 1H, $J_{3-2}$=2.8 Hz and $J_{3-4}$=9.1 Hz, H-3B or H-3C), 4.047–3.88 (m, 7H, H-3D, 3*H-4B, C or D, 3*H-5B, C or D), 3.92–3.89 (m, 1H, —O—CH—CH$_2$—), 3.8–3.5 (m, 8H, H-4A, 4*H-6A, B, C and D, —C:O—OCH$_3$), 3.48 (dd, 1H, $J_{3-2}$=2.5 Hz and $J_{3-4}$=9.4 Hz, H-3A), 3.44–3.39 (m, 2H, H-5A and —O—CH—CH$_2$—), 2.44 (br, 1H, OH), 2.34 (t, 2H, $J_{3-2}$=7.6Hz, —CH$_2$C:O—OCH$_3$), 1.67–1.57 (m, 4H, —(CH$_2$)$_2$—), 1.39–1.28 (m, 8H, —(CH$_2$)$_4$—).

$^{13}$C-NMR (100 MHz): δ 174.2 (—C:O—OCH$_3$), 138.9, 138.77, 138.66, 138.65, 138.56*2, 138.37, 138.35, 138.12*2, 138.07, 137.9 (12 C arom.), 128.4–127.2 (55 CH arom.), 100.8 (C-1D), 100.5 (C-1B or C-1C), 99.9 (C-1A), 99.5 (C-1B or C-1C), 82.3 (C-3A), 80 (C-3D), 79.7 (C-3B or C-3C), 79.5 (C-3B or C-3C), 75.6 (C-5A), 75.3 (C-2B or C-2C), 75.02 (CH$_2$Ph), 75*2 (CH$_2$Ph), 74.93 (C-4A), 74.9 (C-2B or C-2C), 74.88, 74.84, 74.2 (C-4B, C-4C, C-4D), 73.35 (CH$_2$Ph), 73.23 (CH$_2$Ph), 73.21 (CH$_2$Ph), 73.17 (CH$_2$Ph), 73.12 (CH$_2$Ph), 72.5 (C-2A), 72.34 (CH$_2$Ph), 72.2, 71.6, 71.5 (C-5B, C-5C, C-5D), 72.1 (CH$_2$Ph), 72 (CH$_2$Ph), 71.8 (CH$_2$Ph), 69.7, 69.4, 63.37, 69.2 (4*C-6), 68.48 (—O—CH$_2$—), 68.46 (C-2D), 51.4 (—C:O—OCH$_3$), 34 (—CH$_2$—C:O—O—CH$_3$), 29.6, 29.2, 29.16, 29.1, 26, 24.9 (—CH$_2$—).

Mass spectrum: m/z 1934.95 (M+NH4)$^+$.

Analysis for C$_{118}$H$_{132}$O$_{23}$ (1918.35): calculated=C: 73.88 H: 6.93; found=C: 73.84 H: 7.1.

6) 8-carboxyloctyl 2-O-(2-O-(2-O-(α-D-mannopyranosyl)-α-D-mannopyranosyl)-α-D-mannopyranosyl)-α-D-mannopyranoside and β-D-mannopyranoside (II, R=connector).

From the two isomers 18a and 18b, two compounds (II R=connector) were prepared:

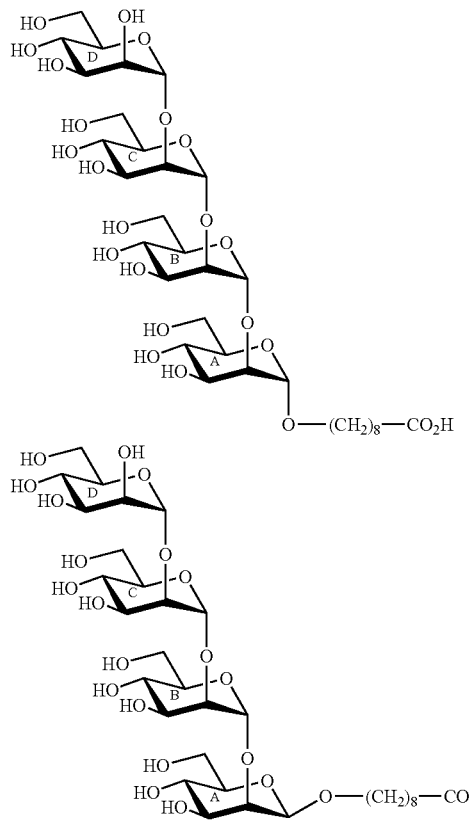

α-aglycone Compound

Step 1: Saponification

For the experimental protocol, see step 2 of I (R=connector).

18a (90 mg, 47 μmol) yields 70 mg (78%) of 8-carboxyloctyl 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-benzyl-α-D-mannopyranoside after silica gel chromatography (elution: cyclohexane/ethyl acetate=2/1): (α)$_D$ +17 (c 1, chloroform).

$^1$H-NMR (400 MHz, CDCl$_3$): δ 7.36–7.23 (m, 55H, arom.), 5.3 (d, 1H, J$_{1-2}$=1.2 H, H-1B or H-1C), 5.27 (d, 1H, J$_{1-2}$=1.6 Hz, H-1B or H-1C), 5.18 (d, 1H, J$_{1-2}$=1.4 Hz, H-1D), 4.99 (d, 1H, J$_{1-2}$=1.4 Hz, H-1A. Absence of the characteristic methyl peak of the methyl ester.

Mass spectrum: m/z 1920.86 (M+NH4)$^+$.

Analysis for C$_{117}$H$_{130}$O$_{23}$ (1904.32): calculated=C: 73.79 H: 6.88; found=C: 73.36 H: 7.12.

Step 2: Hydrogenolysis

For the protocol, see step 3 of I (R=connector).

From 48 mg (25 μmol) of the precursor, 20 mg (yield=95%) were obtained for the compound α-O-connector II (R=connector).

$^1$H-NMR (400 MHz, D$_2$O) of the compound α-O-connector: δ 5.25 (d, 1H, J$_{1-2}$=1.6 Hz, H-1B or H-1C), 5.24 (d, 1H, J$_{1-2}$=1.5 Hz, H-1B or H-1C), 5.04 (d, 1H, J$_{1-2}$=1.3 Hz, H-1D), 4.99 (d, 1H, J$_{1-2}$=2 Hz, H-1A), 3.69–3.63 (m, 1H, —O—CH—CH$_2$—), 3.48 (dt, 1H, J$_{CH—CH2}$=6.2 Hz and J$_{gem}$=9.9 Hz, —O—CH—CH$_2$—), 2.22 (t, 2H, J$_{3-2}$=7.5 Hz, —CH$_2$COOH), 1.58–1.48 (m, 4H, —(CH$_2$)$_2$—), 1.3–1.24 (m, 8H, —(CH$_2$)$_4$—).

$^{13}$C-NMR (100 MHz): δ 102.5, 100.96, 100.91, 98.29 (4 C-1).

Mass spectrum (FAB): calculated C$_{33}$H$_{58}$O$_{23}$Na: m/z 845.32; obtained: 845.37.

β-aglycone Compound

Step 1: Saponification

For the experimental protocol, see step 2 of I (R=connector).

18b (89 mg, 46.3 μmol) yielded 64 mg (72%) of 8-carboxyloctyl 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-O-benzyl-β-D-mannopyranoside: (α)$_D$ +19 (c 1, chloroform).

$^1$H-NMR (400 MHz, CDCl$_3$): δ 7.38–7.25 (m, 55H, arom.), 5.39 (d, 1H, J$_{1-2}$=1.5 Hz, H-1B or H-1C), 5.34 (d, 1H, J$_{1-2}$=1.5 Hz, H-1B or H-1C), 5.23 (d, 1H, J$_{1-2}$=1.45 Hz, H-1D), 4.3 (s, 1H, H-1A). Absence of the characteristic methyl peak of the methyl ester.

Mass spectrum: m/z 1920.9 (M+NH4+)$^+$.

Analysis for C$_{117}$H$_{130}$O$_{23}$ (1904.32): calculated=C: 73.79 H: 6.88; found: C: 73.37 H: 7.28.

Step 2: Hydrogenolysis

For the protocol, see step 3 of compound I (R=connector).

18 mg (92%) II (R=connector) β-O-connector were obtained from 45 mg (23.6 μmol):

$^1$H-NMR (400 MHz, D$_2$O) of the compound β-O-connector: δ 5.33 (d, 1H, J$_{1-2}$=1.3 Hz, H-1B or H-1C), 5.24 (d, 1H, J$_{1-2}$=1.8 Hz, H-1B or H-1C), 4.98 (d, 1H, J$_{1-2}$=1.9 Hz, H-1D), 4.63 (s, 1H, H-1A), 3.84–3.79 (m, 1H, —O—CH—CH$_2$—), 3.53 (dt, 1H, J$_{CH—CH2}$=5.8 Hz and J$_{gem}$=9.9 Hz, —O—CH—CH$_2$—), 2.22 (t, 2H, J$_{3-2}$=7.5 Hz, —CH$_2$COOH), 1.59–1.49 (m, 4H, —(CH$_2$)$_2$—), 1.3–1.24 (m, 8H, —(CH$_2$)$_4$—).

$^{13}$C-NMR (100 MHz): δ 102.5, 100.95, 100.91, 99.99 (4 C-1).

Mass spectrum (FAB): calculated C$_{33}$H$_{58}$O$_{23}$Na: m/z 845.32; obtained: 845.4.

7) 2-O-(2-O-(2-O-(3,4,6-tri-O-benzyl-α-D-mannopyranosyl)-3,4,6-tri-O-benzyl-α-D-mannopyranosyl)-3,4,6-tri-O-benzyl-α-D-mannopyranosyl)-3,4,6-tri-O-benzyl-D-mannopyranose (19)

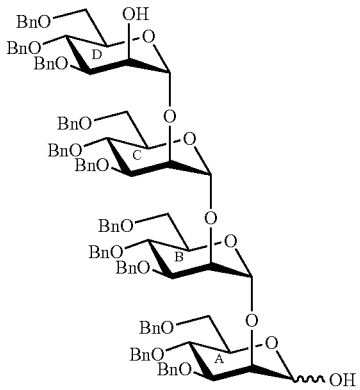

For the experimental protocol, see step 2 of compound I (R=H).

From 105 mg (57 μmol) of compound 17, 84 mg (85%) of compound 19 (α/β=87/13) were obtained after silica gel chromatography (elution: cyclohexane/ethyl acetate=3/1 and then 2/1).

$^1$H-NMR (400 MHz, CDCl$_3$) of the α compound: δ 7.4–7.27 (m, 60H, arom.), 5.38–5.37 (m, 1H, H-1A), 5.34 (d, 1H, $J_{1-2}$=1.5 Hz, H-1B or H-1C), 5.35 (d, 1H, $J_{1-2}$=1.7 Hz, H-1B or H-1C), 5.23 (d, 1H, $J_{1-2}$=1.6 Hz, H-1D), 2.83 (br, 1H, OH), 2.51 (br, 1H, OH).

$^{13}$C-NMR (100 MHz): δ 100.94 (C-1D), 100.9 (C-1B or C-1C), 100.85 (C-1B or C-1C), 93.3 (C-1A).

Mass spectrum: m/z 1769.54 (M+Na)$^+$.

Analysis for C$_{117}$H$_{130}$O$_{23}$ (1748.1): calculated=C: 74.2 H: 6.57; found=C: 74.15 H: 6.7.

8) 2-O-(2-O-(2-O-(α-D-mannopyranosyl)-α-D-mannopyranosyl)-α-D-mannopyranosyl)-D-mannopyranose II (R=H)

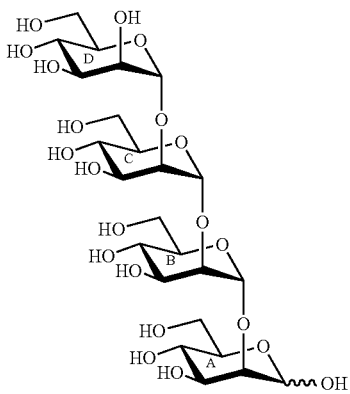

For the experimental protocol, see step 3 of compound I (R=connector).

30 mg (18 μmol) of the preceding compound yielded 18 mg (yield=95%) of compound II (R=H) after lyophilization.

$^1$H-NMR (400 MHz, D$_2$O) of the α-OH compound: δ 5.23 (s, 1H, H-1A), 5.15 (bs, 2H, H-1B and H-1C), 4.91 (d, 1H, $J_{1-2}$=1.6 Hz, H-1D).

Mass spectrum: calculated C$_{24}$H$_{42}$O$_{21}$Na: m/z 689.21; obtained 689.41.

EXAMPLE 3

Preparation of D-Manα(1-3)D-Manα(1-2)D-Manα(1-2)D-Manα(1-2) of formula (III)

I-Reaction Diagram

Figure 3:
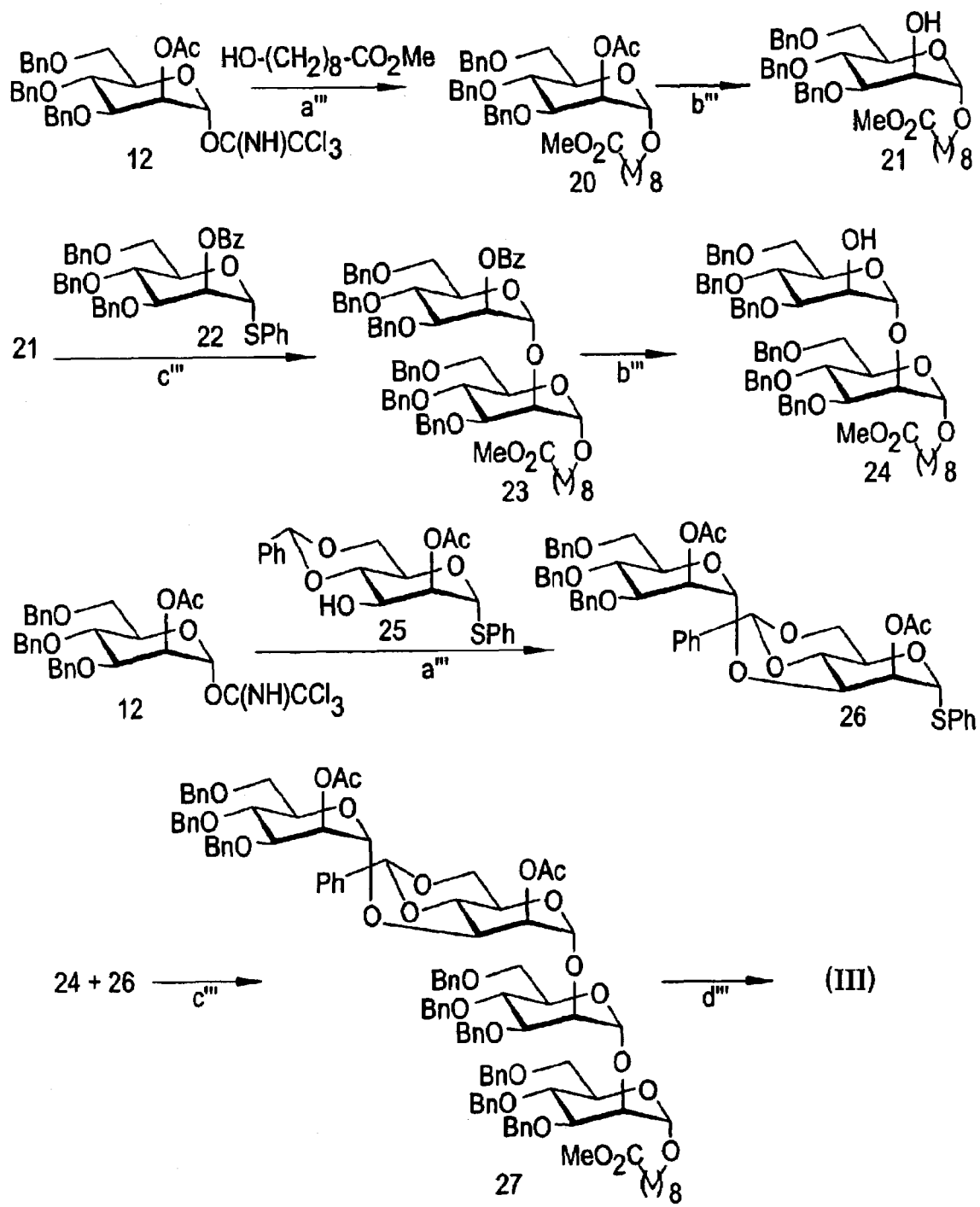
FIG. 3 is a reaction diagram for the preparation of D-Man α(1-3) D-Man α(1-2) D-Man α(1-2) D-Man α(1-2) of formula (III).

FIG. 3 is a reaction diagram for preparing D-Manα(1-3)D-Manα(1-2)D-Manα(1-2)D-Manα(1-2) of formula (III). This compound was prepared by condensation of an α(1-3) block with a starting group SPh and an α(1-2) block, with one having a connector according to reactions (a''') to (d''') below.

Reaction (a''') was performed under the following conditions: TfOTMS, 4-Angstrom molecular sieve, CH$_2$Cl$_2$, −20° C.

Reaction (b''') was performed under the following conditions: MeONa, MeOH.

Reaction (c''') was performed under the following conditions: NIS, TfOH, 4-Angstrom molecular sieve, CH$_2$Cl$_2$, −20° C.

Reaction (d''') was performed under the following conditions: 1-NaOH, THF-water, 2-H$_2$, Pd/C, MeOH, AcOEt.

II-Experimental Protocol

Compounds 22 (Y.-M. Zhang, J.-M. Mallet, P. Sinaÿ, Carbohydr. Res. 236, (1992), 73–88) and 21 (P. J. Garegg, H. Hultberg, T. Norberg, Carbohydr. Res. 96 (1981) 59–64) were prepared according to the protocols in the literature.

1) 8-methoxycarbonyloctyl 2-O-(2-O-benzoyl-3,4,6-tri-O-benzyl-α-D-mannopyranosyl)-3,4,6-tri-O-benzyl-α-D-mannopyranoside (23)

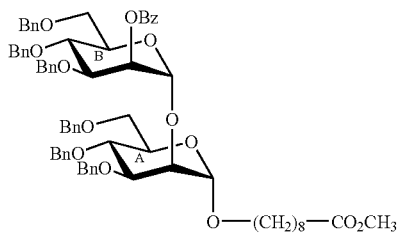

430 mg (665 μmol, 1 eq) of phenyl 2-O-benzoyl-3,4,6-tri-O-benzyl-1-thio-α-D-mannopyranoside (22) (Y.-M. Zhang, J.-M. Mallet, P. Sinaÿ, Carbohydr. Res. 236, (1992), 73–88), 412 mg (1 eq) of 8-methoxycarbonyl 3,4,6-tri-O-benzyl-1-α-D-mannopyranoside (21) (P. J. Garegg, H. Hultberg, T. Norberg, Carbohydr. Res. 96, (1981) 59–64) and 1 g of molecular sieve were put into suspension in 9 ml of anhydrous dichloromethane under an argon atmosphere. After 30 min of agitation at ambient temperature, the solution was cooled to −20° C. 306 mg (2.2 eq) of N-iodosuccinimide and 11.7 ml (0.2 eq) of trifuloromethanesulfonic acid were then added successively. After 30 min at −20° C., the reactional medium was neutralized with a solution of sodium bicarbonate. This was then filtered on a Celite bed; the organic phase was washed with a sodium thiosulfate solution and with an aqueous solution of NaCl. It was then dried over magnesium sulfate, filtered and concentrated under reduced pressure. Chromatography (elution: cyclohexane/ethyl acetate=4/1) of the crude product yielded 615 mg (80%) of product 23 in the form of a colorless oil.

(α)$_D$ +5.2 (c 0.56, chloroform).

¹H-NMR (400 MHz, CDCl₃): δ 8.15–7.25 (m, 35H, arom.), 5.85 (dd, 1H, $J_{2-1}$=1.8 Hz and $J_{2-3}$=3.3 Hz, H-2B), 5.27 (d, 1H, $J_{1-2}$=1.8 Hz, H-1B), 4.96 (d, 1H, $J_{1-2}$=1.66 Hz, H-1A), 4.93 (d, 1H, $J_{gem}$=10.7 Hz, CHPh), 4.92 (d, 1H, $J_{gem}$=10.9 Hz, CHPh), 4.83 (d, 1H, $J_{gem}$=11.1 Hz, CHPh), 4.78 (d, 1H, $J_{gem}$=12 Hz, CHPh), 4.76 (s, 2H, CH₂Ph), 4.74 (d, 1H, $J_{gem}$=12.2 Hz, CHPh), 4.62 (d, 1H, $J_{gem}$=12.2 Hz, CHPh), 4.62 (d, 1H, $J_{gem}$=10.7 Hz, CHPh), 4.58 (d, 1H, $J_{gem}$=12 Hz, CHPh), 4.57 (d, 1H, $J_{gem}$=10.9 Hz, CHPh), 4.51 (d, 1H, $J_{gem}$=11.1 Hz, CHPh), 4.19 (dd, 1H, $J_{3-2}$=3.3 Hz and $J_{3-4}$=9 Hz, H-3B), 4.12–4.09 (m, 2H, H-5B and H-4B), 4.07 (dd, 1H, $J_{2-1}$=1.66 Hz and $J_{2-3}$=2.9 Hz, H-2A), 4 (dd, 1H, $J_{3-2}$=2.9 Hz and $J_{3-4}$=9.2 Hz, H-3A), 3.94 (dd, 1H, $J_{6b-6a}$=10.5 Hz and $J_{6b-5}$=3 Hz, H-6Bb), 3.92 (t, 1H, $J_{4-2}=J_{4-5}$=9.2 Hz, H-4A), 3.85–3.77 (m, 4H, H-6A, H-6Ba and H-5A), 3.71 (s, 3H, —C:O—OCH₃), 3.67 (dt, 1H, $J_{gem}$=9.5 Hz and $J_{CH-CH2}$=6.7 Hz, —O—CH—CH₂—), 3.35 (dt, 1H, $J_{gem}$=9.5 Hz and $J_{CH-CH2}$=6.7 Hz, —O—CH—CH₂—), 2.36 (t, 2H, $J_{CH2-CH2}$=7.5 Hz, —CH₂—CO₂CH₃), 1.69–1.65, 1.57–1.54 and 1.35⎓1.33 (m, 12H, —CH₂—).

¹³C-NMR (100 MHz): δ 174.2 (—C:O—OCH₃), 165.4 (—O—C:O), 138.5, 138.4, 138.32, 138.3, 138.26, 137.98, 129,9 (7 C arom.), 133–127.35 (35 CH arom.), 99.5 (C-1B), 98.6 (C-1A), 79.73 (C-3A), 78.07 (C-3B), 75.2 (C-2A), 75.1 (CH₂Ph), 75 (CH₂Ph), 74.6 (C-4B), 74.3 (C-4A), 73.3 (CH₂Ph), 73.2 (CH₂Ph), 72.1 (CH₂Ph), 71.9 (C-5B), 71.7 (C-5A), 71.6 (CH₂Ph), 69.2 (C-6A), 69.15 (C-6B), 69.98 (C-2B), 67.64 (—O—CH₂), 51.4 (—C:O—OCH₃),34 (—CH₂—COOCH₃), 29.36, 29.17, 29.11, 29, 26, 24.9 (—CH₂—).

Mass spectrum: m/z 1174.5 (M+NH4)⁺.

Analysis for C₇₁H₈₀O₁₄ (1157.40): calculated=C: 73.68 H: 6.96; found=C: 73.61 H: 7.11.

2) 8-methoxycarbonyloctyl 2-O-(3,4,6-tri-O-benzyl-α-D-mannopyranosyl)-3,4,6-tri-O-benzyl-α-D-mannopyranoside (24)

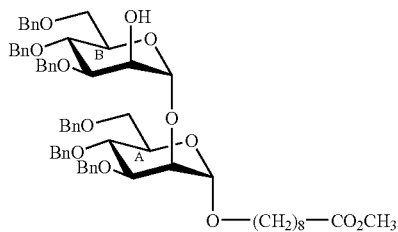

540 mg (467 μmol) of compound 23 was dissolved in 5 ml of a methanol/dichloromethane 1/1 solvent mixture. Sodium (cat.) was then added to the mixture. After 1 hour at ambient temperature, the solution was neutralized with Amberlite resin IR 120 (H+). This was filtered and concentrated under vacuum. Chromatography of the crude product (elution: cyclohexane/ethyl acetate=2.75/1) yielded 442 mg (yield=90%) of product 24 in the form of a colorless oil.

$(\alpha)_D$ +34 (c 0.71, chloroform).

¹H-NMR (400 MHz, CDCl₃): δ 7.4–7.3 (m, 30H, arom.), 5.21 (d, 1H, $J_{1-2}$ =1.45 Hz, H-1B), 4.95 (d, 1H, $J_{1-2}$=1.75 Hz, H-1A), 4.89 (d, 1H, $J_{gem}$=10.6 Hz, CHPh), 4.87 (d, 1H, $J_{gem}$=10.9 Hz, CHPh), 4.75 (d, 1H, $J_{gem}$=12.2 Hz, CHPh), 4.75 (d, 1H, $J_{gem}$=11.6 Hz, CHPh), 4.71 (d, 1H, $J_{gem}$=11.6 Hz, CHPh), 4.69 (d, 1H, $J_{gem}$=12.1 Hz, CHPh), 4.64 (d, 1H, $J_{gem}$=11.4 Hz, CHPh), 4.59 (d, 1H, $J_{gem}$=10.6 Hz, CHPh), 4.59 (d, 1H, $J_{gem}$=12.2 Hz, CHPh), 4.58 (d, 1H, $J_{gem}$=11.4 Hz, CHPh), 4.56 (d, 1H, $J_{gem}$=12.1 Hz, CHPh), 4.54 (d, 1H, $J_{gem}$=10.9 Hz, CHPh), 4.2–4.17 (m, 1H, H-2B), 4.08 (dd, 1H, $J_{2-1}$=1.75 Hz and $J_{2-3}$=2.9 Hz, H-2A), 4.03–3.99 (m, 1H, H-5B), 3.99 (dd, 1H, $J_{3-2}$=2.9 Hz and $J_{3-4}$=9.3 Hz, H-3A), 3.93 (dd, 1H, $J_{3-2}$=3.2 Hz and $J_{3-4}$=9.1 Hz, H-3B), 3.89 (t, 1H, $J_{4-3}=J_{4-5}$=9.3 Hz, H-4A), 3.86 (t, 1H, $J_{4-3}=J_{4-5}$=9.1 Hz, H-4B), 3.86 (dd, 1H, $J_{6b-6a}$=11.1 Hz and $J_{6b-4}$=4.95 Hz, H-6Ab), 3.82–3.75 (m, 4H. H-6Aa, H-6B and H-5A), 3.71 (s, 3H, —C:O—OCH₃), 3.65 (dt, 1H, $J_{gem}$=9.5 Hz and $J_{CH-CH2}$=6.8 Hz, —O—CH—CH₂—), 3.3 (dt, 1H, $J_{gem}$=9.5 Hz and $J_{CH=CH2}$=6.8 Hz, —O—CH—CH₂—), 2.51 (d, 1H, $J_{OH-2}$=1.9 Hz, OH), 2.34 (t, 2H, $J_{CH2-CH2}$=7.6 Hz, —CH₂—CO₂CH₃), 1.7–1.63, 1.56–1.49 and 1.37–1.27 (m, 12H, —CH₂—).

¹³C-NMR (100 MHz): δ 174.3 (—C:O—OCH₃), 138.5, 138.35, 138.3, 138.25, 138.1, 137.9 (6 C arom.), 128.4–127.3 (30 CH arom.), 101 (C-1B), 98.7 (C-1A), 79.92 (C-3B), 79.79 (C-3A), 75.1 (CH₂Ph), 74.95 (CH₂)h), 74.93 (C-2A), 74.76 (C-4A), 74.3 (C-4B), 73.3 (CH₂Ph), 73.2 (CH₂Ph), 72.8 (CH₂Ph), 72 (CH₂Ph), 71.7 (C-5B), 71.7 (C-5A), 69.2 (C-6A), 69 (C-6B), 68.45 (C-2B), 67.63 (—O—CH₂—), 51.4 (—C:O—OCH₃), 34 (—CH₂—COOCH₃), 29.4, 29.2, 29.1, 29, 26, 24.9 (—CH₂—).

Mass spectrum: m/z 1070.5 (M+NH4)⁺.

Analysis for C₆₄H₇₆O₁₃ (1053.30): calculated=C: 72.98 H: 7.27; found=C: 72.89 H: 7.43.

3) Phenyl 2-O-acetyl-4,6-O-benzylidene-1-thio-α-D-mannopyranoside (25)

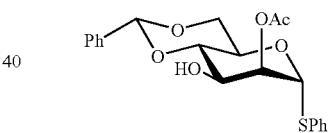

2 g (5.5 mmol, 1 eq) of phenyl 4,6-O-benzylidene-1-thio-α-D-mannopyranoside 1 and 292 mg (1.2 mmol, 0.2 eq) of 10-DL-camphorsulfonic acid were dissolved in 10 ml of triethyl orthoacetate. After 30 min at ambient temperature, 14.4 ml of 80% acetic acid was added to the solution which had previously been cooled to 0° C. After 1 hour, the temperature was allowed to climb to ambient temperature, the mixture was concentrated and chromatographed over silica gel (elution: cyclohexane/ethyl acetate=2/1). After evaporation of the solvents, 1.67 g (75%) of compound 25 was obtained in the form of a white powder.

m.p.: 157–158° C.; $(\alpha)_D$ +169 (c 1.05, chloroform).

¹H-NMR (400 MHz, CDCl₃): δ 7.56–7.3 (m, 10H, arom.), 5.66 (s, 1H, by), 5.52 (s, 1H, H-1), 5.51 (dd, 1H, $J_{2-1}$=1.3 Hz and $J_{2-3}$=3.3 Hz, H-2), 4.41 (ddd, 1H, $J_{5-4}$=9.7 Hz, $J_{5-6a}$=10.3 Hz and $J_{6b-5}$=4.9 Hz, H-6b), 4.28–4.25 (m, 1H, H-3), 4.04 (t, 1H, $J_{4-3}=J_{4-5}$=9.7 Hz, H-4), 3.89 (t, 1H, $J_{6b-6a}=J_{6b-5}$=10.3 Hz, H-6a), 2.65 (d, 1H, $J_{OH-3}$=3.5 Hz, OH), 2.21 (s, 3H, O—C:O—CH₃).

¹³C-NMR (100 MHz): δ 170.3 (—O—C:O—CH₃), 136.9, 133 (2 C arom.), 132–126.2 (10 CH arom.), 102.2

(by), 86.8 (C-1), 79 (C-4), 73.5 (C-2), 68.3 (C-6), 67.7 (C-3), 64.5 (C-5A), 20.9 (—O—C:O—CH$_3$).

Mass spectrum: m/z 403.2 (M+H)$^+$.

Analysis for C$_{21}$H$_{22}$O$_6$S (402.46): calculated=C: 62.67 H: 5.509; found=C: 62.66 H.54.

4) Phenyl 3-O-(2-O-acetyl-3,4,6-tri-O-benzyl-α-D-mannopyranosyl)-2-O-acetyl-4,6-O-benzylidene-1-thio-α-D-mannopyranoside (26)

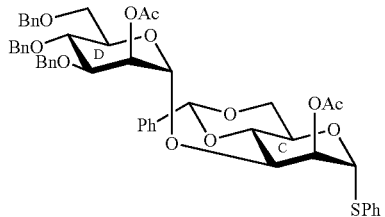

731 mg (1.15 mmol, 1.1 eq) of O-(2-O-acetyl-3,4,6-tri-O-benzyl-α-D-manno-pyranose)trichloroacetimidate (12), 420 mg (1.044 mmol, 1 eq) of compound 25 and 1.3 g of molecular sieve were put into suspension in 12 ml of anhydrous dichloromethane and maintained under an argon atmosphere. After 30 min of agitation at ambient temperature, the solution was cooled to −20° C. and 22 μl (0.1 eq) of trimethylsilyl trifluorometh-anesulfonate was injected. After 1 hour of agitation, the solution was neutralized with a solution of sodium bicarbonate and filtered over Celite. The separated-out organic phase was washed with an aqueous solution of NaCl, dried over magnesium sulfate, filtered and concentrated under vacuum. The crude product was chromatographed over silica gel (elution: cyclohexane/ethyl acetate=4/1) and 626 mg (yield=68%) of compound 26 was thereby isolated in the form of a white foam. m.p.: 58–59° C.

(α)$_D$ +119 (c 0.55 m chloroform).

$^1$H-NMR (400 Hz. CDCL$_3$): δ 7.47–7.25 (m, 25H, arom.), 5.69 (s, 1H, by), 555 (dd, 1H, J$_{2-1}$=1.8Hz and J$_{2-3}$=2.7 Hz, H-2D), 5.52 (dd, 1H, J$_{2-1}$=1.3 Hz and J$_{2-3}$=3.4 Hz, H-2C), 5.49 (d, 1H, J$_{1-2}$=1.3 Hz, H-1C), 5.34 (d, 1H, J$_{1-2}$=1.8 Hz, H-1D), 4.89 (d, 1H, J$_{gem}$=10.9 Hz, CHPh), 4.77 (d, 1H, J$_{gem}$=12.2 Hz, CHPh), 4.74 (d, 1H, J$_{gem}$=11.4 Hz, CHPh), 4.56 (d, 1H, J$_{gem}$=12.2 Hz, CHPh), 4.56 (d, 1H, J$_{gem}$=11.4 Hz, CHPh), 4.54 (d, 1H, J$_{gem}$=10.9 Hz, CHPh), 4.42 (ddd, 1H, J$_{5-4}$=9.8 Hz, J$_{5-6b}$=4.9 Hz and J$_{5-6a}$=10.3 Hz, H-5C), 4.4 (dd, 1H, J$_{3-2}$=3.4 Hz and J$_{3-4}$=9.8 Hz, H-3C), 4.3 (dd, 1H, J$_{6b-6a}$=10.4 Hz and J$_{6b-5}$=4.9 Hz, H-6Cb), 4.2 (t, 1H, J$_{4-3}$=J$_{4-5}$=9.8 Hz, H-4C), 3.97–3.87 (m, 4H, H-5D, H-4D, H-3D and H-6Ca), 3.86 (dd, 1H, J$_{6b-6a}$=12 Hz and J$_{6b-5}$=3.9 Hz, H-6Db), 3.78 (dd, 1H, J$_{6a-6b}$=12 Hz and J$_{6a-5}$=3.3 Hz, H-6Da), 2.21 and 2.16 (2s, 6H, 2 O—C:O—CH$_3$).

$^{13}$C-NMR (100 MHz): δ 170.1 and 169.7 (2 —O—C: O—CH$_3$), 138.4, 138.2, 137.9, 136.9, 133 (C arom.), 132–125.9, (25 CH arom.), 101.3 (by), 98.8 (C-1D), 86.8 (C-1C), 78.9 (C-4C), 75.6, 74.1 and 72.1 (C-3D, C-4D and C-5D), 74.9 (CH$_2$Ph), 73.4 (CH$_2$Ph), 73.1 (C-2C), 71.7 (CH$_2$Ph), 70.8 (C-3C), 68.6 (C-6D), 68.4 (C-2D), 68.2 (C-6C), 64.6 (C-5C), 21 and 20.8 (2 —O—C:O—CH$_3$).

Mass spectrum: m/z 894.3 (M+NH$_4$)$^+$.

Analysis for C$_{50}$H$_{52}$O$_{12}$S (877.02): calculated=C: 68.47 H: 5.976; found=C: 68.36 H: 6.15.

5) 8-methoxycarbonyloctyl 2-O-(2-O-(3-O-(2-O-acetyl-3,4,6-tri-O-benzyl-α-D-manno-pyranosyl)-2-O-acetyl-4,6-O-benzylidene-α-D-mannopyranosayl)-3,4,6-tri-O-benzyl-α-D-mannopyranosyl)-3,4,6-tri-O-benzyl-α-D-mannopyranoside (27)

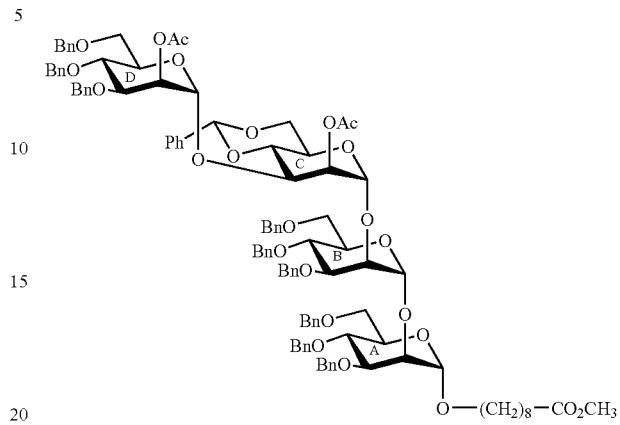

158 mg (180 μmol, 1 eq) of compound 26, 186 mg (1 eq) of compound 24 and 500 mg of molecular sieve were put into solution in 5 ml of anhydrous dichloromethane and maintained under an argon atmosphere. After 30 min of agitation, the solution was cooled to −20° C., and 81 mg (2 eq of N-iodosuccinimide as well as 4 μl (0.3) of trifluoromethanesulfonic acid were added to the medium. After 30 min of agitation, the medium was neutralized with a solution of sodium bicarbonate and filtered over a Celite bed. The organic phase was then washed with a sodium thiosulfate solution, by an aqueous solution of NaCl, dried over magnesium sulfate, filtered and concentrated under reduced pressure. The crude product was chromatographed over silica gel (elution: cyclohexane/ethyl acetate=5/1) and 236 mg (yield=72%) of product 27 was thereby isolated in the form of a colorless oil.

(α)$_D$ +29 (c 0.85 m chloroform).

$^1$H-NMR (400 MHz, CDCl$_3$): δ 7.38–7.25 (m, 50H, arom.), 5.66 (s, 1H, by), 5.56 (dd, 1H, J$_{2-1}$=1.5 Hz and J$_{2-3}$=3 Hz, H-2D), 5.44 (dd, 1H, J$_{2-1}$=1.3 Hz and J$_{2-3}$=3.5 Hz, H-2C), 5.32 (bs, 1H, H-1D), 5.2 (bs, 1H, H-1B), 5.04 (bs, 1H, H-1C), 4.94 (bs, 1H, H-1A), 4.88 (d, 1H, J$_{gem}$=10.6 Hz, CHPh), 4.88 (d, 1H, J$_{gem}$=10.7 Hz, CHPh), 4.87 (d, 1H, J$_{gem}$=10.9 Hz, CHPh), 4.75 (d, 1H, J$_{gem}$=12.4 Hz, CHPh), 4.75 (d, 1H, J$_{gem}$=11.2 Hz, CHPh), 4.72 (s, 2H, CH$_2$Ph), 4.67 (d, 1H, J$_{gem}$=12.3 Hz, CHPh), 4.67 (d, 1H, J$_{gem}$=12 Hz, CHPh), 4.61 (d, 1H, J$_{gem}$=12.4 Hz, CHPh), 4.6 (d, 1H, J$_{gem}$=10.6 Hz, CHPh), 4.6 (d, 1H, J$_{gem}$=12 Hz, CHPh), 4.58 (s, 2H, CH$_2$Ph), 4.57 (d, 1H, J$_{gem}$=11.2 Hz, CHPh), 4.53 (d, 1H, J$_{gem}$=10.9 Hz, CHPh), 4.52 (d, 1H, J$_{gem}$10.7 Hz, CHPh), 4.33 (d, 1H, J$_{gem}$=12.3 Hz, CHPh), 4.43 (dd, 1H, J$_{3-2}$=3.5 Hz, and J$_{3-2}$=9.3 Hz, H-3C), 4.21 (dd, 1H, J$_{6b-6a}$=10.4 Hz and J$_{6b-5}$=4.5 Hz, H-6Cb), 4.1404.12 (m, 1H, H-2B), 4.09 (t, 1H, J$_{4-2}$=J$_{4-5}$=9.3 Hz, H-4C), 4.07–4.04 (m, 1H, H-5C), 4.03 (t, 1H, J$_{4-3}$=J$_{4-5}$=9.9 Hz, H-4D), 4.01–4 (m, 1H, H-2A), 3.98–3.96 (m, 1H, H-3B), 3.93 (dd, 1H, J$_{3-2}$=3 Hz and J$_{3-4}$=9.9 Hz, H-3D), 3.88–3.85 (m, 1H, H-5D), 3.71 (s, 3H, —C:O—OCH$_3$), 3.62–3.59 (m, 1H, H-6Da), 3.6–3.56 (m, 1H, —O—CH—CH$_2$—), 3.25 (dt, 1H, J$_{gem}$=9.4 Hz and J$_{CH-CH2}$=6.6 Hz, —O—CH—CH$_2$—), 2.34 (t, 2H, J$_{CH2-CH2}$=7.5 Hz, —CH$_2$—CO$_2$CH$_3$), 2.14 and 2.13 (2s, 6H, 2 O—C:O—CH$_3$), 1.7–1.62, 1.54–1.47 and 1.35–1.25 (m, 12H, —CH$_2$—).

$^{13}$C-NMR (100 MHz): δ 174.3 (—C:O—OCH$_3$), 170.1 and 169.5 (2 —O—C:O—CH$_3$), 138.6, 138.55, 138.3*2, 138.29*2, 138.23, 138.2, 137.98, 137 (10 C arom.), 128.7–125.9 (50 CH arom.), 101.2 (by), 100.6 (C-1B, $^1J_{CH}$=171.3 Hz), 99.8 (C-1C, $^1J_{CH}$=172.2 Hz), 98.8 (C-1D, $^1J_{CH}$=174 Hz), 98.6 (C-1A, $^1J_{CH}$=170.5 Hz), 79.3 (C-3B), 78.9 (C-4C), 77.7 (C-3D), 75.56 (C-2A), 75.4 (C-2B), 75.12 (CH$_2$Ph), 75.06 (CH$_2$Ph), 74.87 (CH$_2$Ph), 73.9 (C-4D), 73.24 (CH$_2$Ph), 73.22 (CH$_2$Ph), 73.2 (CH$_2$Ph), 72.17 (CH$_2$Ph), 72.09 (CH$_2$Ph), 72 (C-5D), 71.7 (CH$_2$Ph), 71.4 (C-2C), 70.8 (C-3C), 68.05 (C-2D), 687.4 (C-6C), 67.63 (—O—CH$_2$—), 51.4 (—C:O—OCH$_3$), 34 (—CH$_2$—COOCH$_3$), 29.4, 29.2, 29.1, 29, 26, 24.9 (—CH$_2$—), 21 and 20.8 (2 —O—C:O—CH$_3$).

Mass spectrum: m/z 1836.5 (M+NH4)$^+$.

Analysis for C$_{108}$H$_{122}$O$_{25}$ (1820.026): calculated=C: 71.27 H: 6.75; found=C: 71.08 H: 6.94.

6) 8-carboxyloctyl 2-O-(2-O-(3-O-α-D-mannopyranosyl)-α-D-mannopyranosyl)-α-D-mannopyranosyl)-α-D-mannopyranoside III

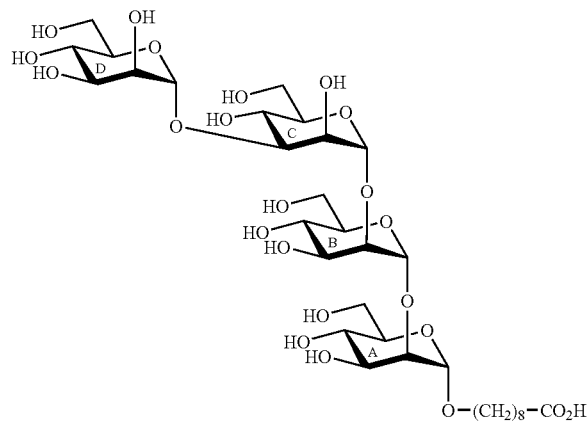

Step 1: Saponification 200 mg (110 μmol, 1 eq) of the precursor 27 were dissolved in 10 ml of a 1/1 mixture of tetrahydrofuran/sodium hydroxide solution (0.1 N). After being left overnight at reflux, the reactional medium was acidified and extracted three times with dichloromethane. The organic phase was then dried over magnesium sulfate, filtered and concentrated under vacuum. The crude product was chromatographed over silica gel (elution: cyclohexane/ethyl acetate=1.5/1) and 155 mg (yield=82%) of the compound was isolated in the form of a colorless oil.

8-carboxyloctyl 2-O-(2-O-(3-O-(3,4,6-tri-O-benzyl-α-D-mannopyranosyl)-4,6-O-benzylidene-α-D-mannopyranosyl)-3,4,6-tri-O-benzyl-α-D-mannopyranosyl)-3,4,6-tri-O-benzyl-α-D-mannopyranoside $(α)_D$ +33.3 (c 0.52 m chloroform).

$^1$H-NMR (400 MHz, CDCl$_3$): δ 7.57.25 (m, 50H, arom.), 5.6 (s, 1H, by), 5.21 (d, 1H, J$_{1-2}$=1.3 Hz, H-1B), 5.16 (d, 1H, J$_{1-2}$=1.45 Hz, H-1D), 5.12 (d, 1H, J$_{1-2}$=1.1 Hz, H-1C), 4.97 (d, 1H, J$_{1-2}$=1.2 Hz, H-1A), 4.42–4.41 (m, 1H, H-2C), 4.18–4.17 (m, 1H, H-2B), 4.08 (m, 1H, H-2D), 4 (dd, 1H, J$_{2-1}$=1.2 Hz and J$_{2-3}$=3.1 Hz, H-2A), 3.6 (dt, 1H, J$_{gem}$=9.5 Hz and J$_{CH-CH2}$=6.5 Hz, —O—CH—CH$_2$—), 2.35 (t, 2H, J$_{CH2-CH2}$=7.5 Hz, —CH$_2$—CO$_2$H), 1.7–1.6, 1.54–1.47 and 1.35–1.25 (m, 12H, —CH$_2$—).

Absence of the three peaks corresponding to the methyls of the esters.

$^{13}$C-NMR (100 MHz): δ 178.5 (—CO$_2$H), 102.3 (C-1C), 101.7 (by), 100.9 (C-1B), 99.8 (C-1D), 98.5 (C-1A), 75.7 (C-2A), 74.8 (C-2B), 69.65 (C-2C), 68.5 (C-2D), 67.6 (—O—CH$_2$—), 33.8 (—CH$_2$—COOH), 29.3, 29, 28.9, 28.7, 25.9, 24.5 (—CH$_2$—), 21 and 20.8 (2 —O—C:O—CH$_3$).

Mass spectrum: m/z 1738.9 (M+NH4)$^+$.

Analysis for C$_{103}$H$_{116}$O$_{23}$ (1722.059): calculated=C: 71.84 H: 6.789; found=C: 71.73 H: 6.91.

Step 2

For the experimental protocol, see step 3 of compound I (R=connector).

100 mg (58 μmol) of the preceding compound yielded 40 mg (yield=83%) of compound III in the form of an amorphous white powder after lyophilization.

$^1$H-NMR (400 MHz, D$_2$O): δ 5.25 (d, 1H, J$_{1-2}$=1.2 Hz, H-1B), 5.1 (d, 1H, J$_{1-2}$=1.3 HZ, H-1D), 5.05 (D, 1H, J$_{1-2}$=0.8 HZ, H-1A), 4.99 (D, 1H, J$_{1-2}$=1.4 HZ, H-1C), 4.19 (dd, 1H, J$_{2-1}$=1.42 Hz and J$_{2-3}$=3 Hz, H-2C), 4.07 (dd, 1H, J$_{2-1}$=1.2 Hz and J$_{2-3}$=3.1 Hz, H-2B), 4.03 (dd, 1H, J$_{2-1}$=1.3 Hz and J$_{2-3}$=3.3 Hz, H-2D), 3.9–3.88 (m, 1H, H-2A), 3.92 (dd, 1H, J$_{3-2}$=3.1 Hz and J$_{3-4}$=9.6 Hz, H-3B), 3.91 (dd, 1H, J$_{3-2}$=3 Hz and J$_{3-4}$=9.4 Hz, H-3C), 3.72 03.65 (m, 1H, —O—CH—CH$_2$—), 3.49 (dt, 1H, J$_{gem}$=10 Hz and J$_{1a-CH2}$=6.2 Hz, —O—CH—CH$_2$—), 2.32 (t, 2H, J$_{CH2-CH2}$=7.4 Hz, —CH$_2$—CO$_2$H), 1.6–1.5 and 1.33–1.26 (m, 12H, —CH$_2$—).

$^{13}$C-NMR (100 MHz): δ 178.3 (—CO$_2$H), 102.5 (C-1D), 102.49 (C-1C), 100.99 (c-1B), 98.3 (C-1A), 79.3 (C-2A), 78.9 (C-2B), 78.2 (C-3C), 73.66, 73.6*2, 73 (4*C-5), 70.63 (C-3D), 70.61 (C-3A), 70.34 (C-2D), 70.28 (C-3B), 69.9 (C-2C), 68.3 (—O—CH$_2$—), 67.4, 67.24, 67.2, 66.5 (4*C-4), 61.4*2, 61.3 61.2 (4*C-6), 34.6 (—CH$_2$—COOH), 28.7, 28.56, 28.55, 28.48, 25.6, 24.6 (—CH$_2$—).

Mass spectrum (negative FAB): calculated C$_{33}$H$_{57}$O$_{23}$: m/z 821.32; obtained: 821.32.

EXAMPLE 4

Synthesis of the Dimannosides VII

Figure 4:
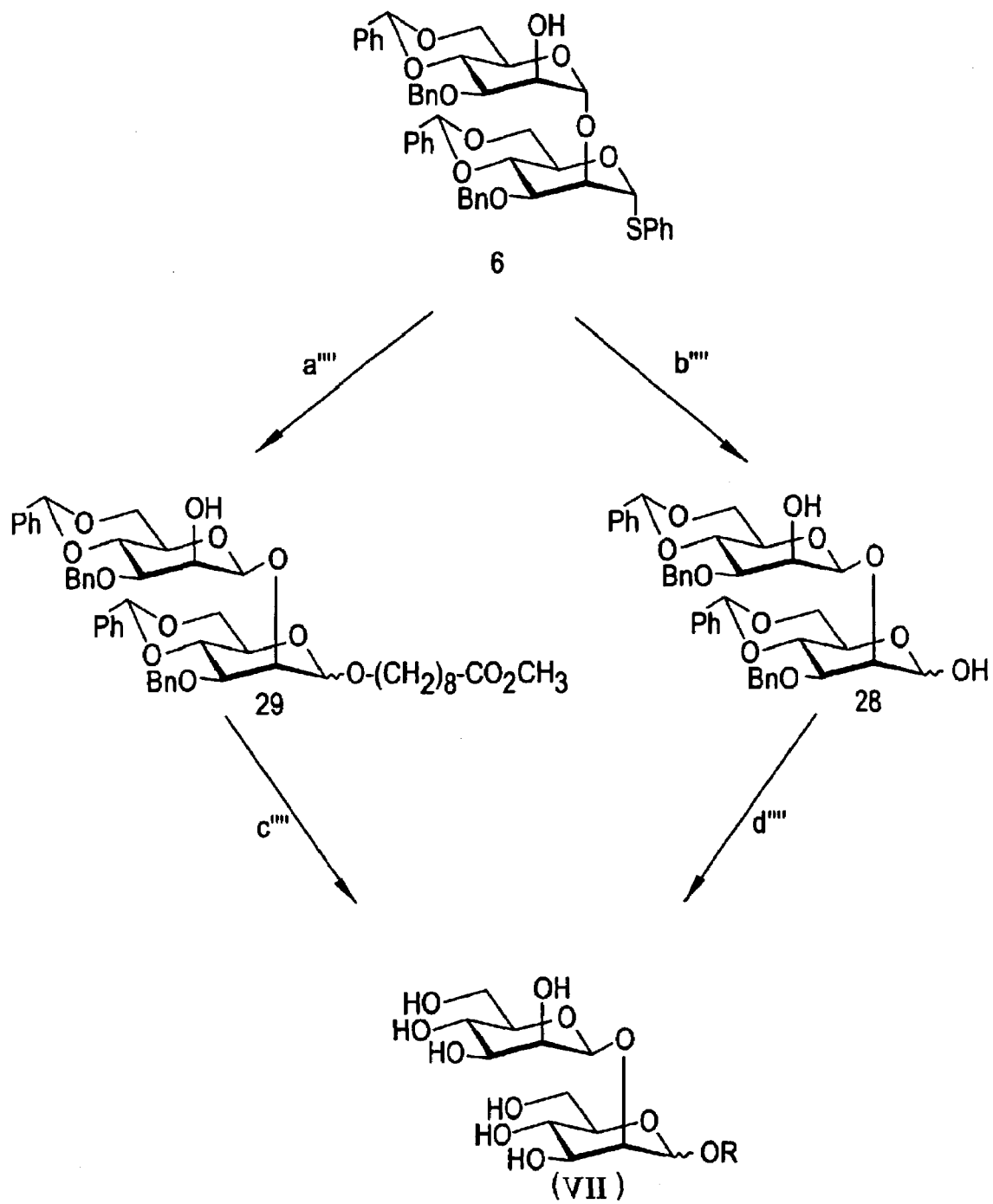
FIG. 4 is a reaction diagram for the preparation of Man β(1-2) Man dimannosides.

FIG. 4 is a reaction diagram for the protocol described below.

1) 2-O-(3-O-benzyl-4,6-O-benzylidene-β-D-mannopyranosyl)-3-O-benzyl-4,6-O-benzylidene-D-mannopyranoside (28)

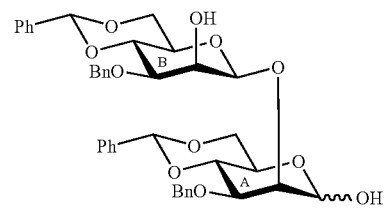

For the experimental protocol, see step 2 of compound 9.

Compound 6 (200 mg, 252 μmol, 1 eq) yielded 160 mg (yield=90%) of compound 28 (α/β=1/1) in the form of a white foam after silica gel chromatography (elution: cyclohexane/ethyl acetate=1.5/1).

$^1$H-NMR (250 MHz, CDCl$_3$) of the α-OH and β-OH mixture: δ 7.46–7.16 (m, 20H, arom.), 5.49*3 and 5.43 (2s, 4H, 4*by), 5.21 (bs, 1H, H-1), 4.89–4.59 (m, 11H, 3*H-1 and 4*CH$_2$Ph), 4.35–3.55 (m, 20H, 4*H-2, 4*H-3, 4*H-4 and 4*H-6), 3.4–3.21 (m, 4H, 4*H-5).

Mass spectrum: m/z 716 (M+NH4)$^+$.

Analysis for $C_{40}H_{42}O_{11}$ (698.77): calculated=C: 68.75 H: 6.058; found=C: 68.50 H: 6.26.

1) 2-O-(β-D-mannopyranosyl)-D-mannopyranose (IV, R=H)

For the experimental protocol, see step 3 of the compound (I, R=connector).

Compound 28 (130 mg, 35 μmol) yielded 56.7 mg (yield=85%) of (IV, R=H) in the form of an amorphous white powder after lyophilization.

$^1$H-NMR (400 MHz, D$_2$O) of the α-OH compound: δ 5.27 (d, 1H, $J_{1-2}$=1.7 Hz, H-1A), 4.76 (s, 1H, H-1B), 4.11 (dd, 1H, $J_{2-1}$=1.7 Hz and $J_{2-3}$=3.3 Hz, H-2A), 4.03 (d, 1H, $J_{2-3}$=3.1 Hz, H-2B), 3.84 (dd, 1H, $J_{3-2}$=3.3H and $J_{3-4}$=9.7 Hz, H-3A), 3.63 (dd, 1H, $J_{3-2}$=3.1 Hz and $J_{3-4}$=9.5 Hz, H-3B).

$^{13}$C-NMR (100 MHz): δ 99.01 (C-1B), 92.25 C-1A), 78.30 (C-2A), 71.13 (C-2B).

$^1$H-NMR (400 MHz, D$_2$O) of the β-OH compound: δ 4.97 (s, 1H, H-1A), 4.83 (s, 1H, H-1A), 4.17 (d, 1H, $J_{2-3}$=3 Hz, H-2A), 4.16 (d, 1H, $J_{2-3}$=3.3 Hz, H-2B), 3.65–3.61 (m, 2H, H-3A and H-3B).

$^{13}$C-NMR (100 MHz): δ 101.18 (C-1B), 93.99 (C-1A), 79.68 (C-2A), 70.63 (C-2B).

HRMS mass spectrum: (M–OH+NH$_3$) calculated 342.1400 observed: 342.1391

(M+NH$_4$)$^+$ calculated: 360.1506 observed: 360.1517.

2) 8-methoxycarbonyloctyl 2-O-(3-O-benzyl-4,6-O-benzylidene-β-D-mannopyranosyl)-3-O-benzyl-4,6-O-benzylidene-D-mannopyranoside (29)

For the experimental protocol, see compound 10.

Compound 6 (250 mg, 316 μmol) yielded 190 mg (yield=70%) of compound 29 (α/β mixture=1/1, not separable) in the form of a colorless oil after silica gel chromatography (elution: cyclohexane/ethyl acetate=1.5/1).

1H-NMR (250 MHz, CDCl3): δ 7.45–7.18 (m, 20H, arom.), 5.51*2. 5/49 and 5.43 (2s, 4H, 4*by), 4.86 (s, 1H, H-1), 4.80–4.67 (m, 10H, 2*H-1 and 4*CH$_2$Ph), 4.41 (s, 1H, H-1), 4.31–3.53 (m, 28H, 4*H-2, 4*H-3, 4*H-4, 4*H-6, 2*—C:O—O—CH$_3$ and 2*—O—CH$_2$—), 3.42–3.21 (m, 6H, 4*H-5 and 2*—O—CH$_2$—), 2.26–2.18 (m, 4H, 2*—CH$_2$—CO$_2$CH$_3$), 1.54–1.18 (m, 24H, —O—CH$_2$—(CH$_2$)6-CH$_2$—C:O—).

Mass spectrum: m/z 886 (M+NH4)$^+$.

Analysis for $C_{50}H_{60}O_{13}$ (869.028): calculated=69.10 H: 6.959; found=C: 68.55 H: 7.41.

3) 8-carboxyloctyl 2-O-(β-D-mannopyranosyl)-D-mannopyranoside (VII, R=connector)

Step 1: For the experimental protocol, see step 2 of the compound (I, R=connector).

60 mg (69 μmol) of the precursor 29 yielded 42 mg (yield=72%) after silica gel chromatography (elution: cyclohexane/ethyl acetate=1/1) in the form of a white powder.

$^1$H-NMR (250 MHz, CDCl$_3$): δ 7.45–7.18 (m, 20H, arom.), 5.51*2, 5.49 and 5.43 (2s, 4H, 4*by). Absence of characteristic methyl peak of the methyl ester.

HRMS mass spectrum: m/z calculated: 855.3956; observed: 855.3958.

Analysis for $C_{40}H_{42}O_{11}$ (855.0008): calculated=C: 68.83 H: 6.837; found=C: 68.64 H: 7.10.

Step 2: For the experimental protocol, see step 3 of the compound (I, R=connector).

From 30 mg (35 μmol) of the preceding intermediary, 15 mg (yield=92%) of (VII, R=connector) was recovered in the form of an amorphous powder after lyophilization.

$^1$H-NMR (400 MHz, D$_2$O) of the α-O-connector compound: α 4.97 (s, 1H, H-1A), 4.75 (s, 1H, H-1B), 4.12 (d, 1H, $J_{2-3}$=3 Hz, H-2A), 4.03 (d, 1H, $J_{2-3}$=2.9 Hz, H-2B), 3.91–3.87 (m, 1H, —O—CH—), 3.81 (dd, 1H, $J_{3-2}$=3 Hz and $J_{3-4}$=9.8 Hz, H-3A), 3.65–3.61 (m, 1H, —O—CH—), 3.62–3.59 (m, 1H, H-3B), 2.3 (t, 2H, $J_{CH2=CH2}$=7.4 Hz, —CH$_2$—CO$_2$H), 1.63–1.56 (m, 4H, —(CH$_2$)$_2$—), 1.35–1.29 (m, 8H, —(CH$_2$)$_4$—).

$^{13}$C-NMR (100 MHz): δ 98.94 (C-1B, $^1J_{C-H}$=155 Hz), 97.83 (C-1A, $^1J_{C-H}$=170 Hz), 77.58 (C-2A), 71.1 (C-2B).

$^1$H-NMR (400 MHz, D$_2$O) of the β-O-connector: δ 4.83 (s, 1H, H-1B), 4.72 (s, 1H, H-1A), 4.24 (d, 1H, $J_{2-3}$=2.9 Hz, H-2A), 4.11 (d, 1H, $J_{2-3}$=2.9 Hz, H-2B), 3.77–3.72 (m, 1H, —O—CH—), 3.66–3.61 (m, 2H, H-3A and H-3B), 3.57–3.51 (m, 1H, —O—CH—), 2.3 (t, 2H, $J_{CH2-CH2}$=7.4 Hz, —CH$_2$—CO$_2$H), 1.63–1.56 (m, 4H, —(CH$_2$)$_2$—), 1.35–1.29 (m, 8H, —(CH$_2$)$_4$—).

$^{13}$C-NMR (100 MHz): δ(101.04 (C-1B, $^1J_{C-H}$=157.5 Hz), 78.4 (C-2A), 70.7 (C-2B).

HRMS mass spectrum: (M–OH+NH3) calculated: 498.2551; observed 498.2531.

(M+NH4)$^+$ calculated: 516.2656; observed: 516.2671.

EXAMPLE 5

Procedures for Covalent Coupling of the Synthetic Oligomannosides of the Invention This coupling has the following advantages:
robust surface, adapted to immunoanalytic tests,
better orientation of the biomolecule,
higher density of epitopes,
fewer problems of antibody recognition: accessible antigenic site.

Use of the Carbodiimide:

This method consists of activating the carboxylic acid groups of the biomolecules themselves for the carbodiimide, which leads to an activated ester, then to the formation of amide bonds with the primary amine groups of the surface (Nunc TechNote Vol. 4 No. 27–28). The water-soluble carbodiimide (EDC: 1-ethyl-3-(3-dimethylaminopropyl)carbodiimide) is used for activating the —COOH groups of the biomolecule in the presence of sulfo-N-hydroxy succinimide (sulfo-NHS: N-hydroxysuccinimide) (Timkovich, R., 1977, Anal. Biochem. 79: 139–143; Staros, J. V. et al., 1986, Anal. Biochem. 156: 220–222; Rasmussen, S. E., 1990, Ann. Biol. Clin. 48: 647–650). Sulfo-NHS suppresses effectively the hydrolysis of the activated product and enables affixation of the synthetic sugar on the surface of the plate that has already been sensitized by the NH2 group.

1) Material:

Dissolve all of the coupling reagents in distilled water. The remaining reagents are reconstituted in demineralized water.

Covalink NH2 C8 (Cat. Polylabo. No. N70897).
Synthetic tetramannose sugars β-bound to an 8-carbon chain (bras Lemieux): 200 mg.
Sulfo-NHS: sulfo-N-hydroxysuccinimide, PIERCE cat. No. 24510.
EDC: 1-ethyl-3-(3-dimethylaminopropyl)-carbodiimide, Novabiochem, PIERCE No. 01-62-0011.
PBS 0.15 M Na+, pH 7.2, Sigma.
PBS/Tween PBS, 0.05%; Tween 20, Sigma.
PBS/Tween/BSA: PBS/Tween, 0.5% BSA.
Skimmed milk.

2) Protocol:

The synthetic tetramannoside is used on two different plates.

From a mother sugar solution at 0.8 mg/ml, 6 dilutions are made at the rate of 2 each to obtain a range of concentration of 40 to 1.25 µg/ml in distilled water.

A solution of the following is prepared in an extemporaneous manner:

NHS 3.48 mg/ml
EDC 3.07 mg/ml

Multiple wells are provided for the blank and the controls (sugars without coupling reagents, a control for the conjugate).

Activation and Coupling:

The sugar solution is deposited successively at the rate of 100 µl per well:
NHS 50 µl/well
EDC 50 µl/well
The plates are covered with a plastic film.
The plates are incubated overnight at ambient temperature with gentle agitation.

Washings and Saturation:

Three washings with water (300 µl/well).
Saturation with 300 µl/well of a 5% solution of skimmed milk in the PBS buffer.
Incubation for 1 hour at ambient temperature.
Five washings with PBS-Tween 20 (0.05%) at the rate of 300 µl/well.

Detection by the ELISA Method:

The coupled sugars can be detected by monoclonal antibody B52 diluted to the $250^{th}$ in a PBS-Tween-BSA solution and then deposited at the rate of 100 µl/well.
Five washings with a PBS-Tween solution.

Developing:

Deposit 100 µl/well of conjugate (example: rat anti-IgM diluted to the $500^{th}$ for developing 5B2) in a PBS-Tween-BSA solution then incubate for 1 hour at ambient temperature.
5 PBS/Tween washings (300 µl/well).
Development by addition of a tetramethylbenzidine (TMB) based chromogenic substrate.
200 µl of TMB (Development kit, Sanofi Diagnostics Pasteur, Marnes-La-Coquettes).
Incubate the plates at ambient temperature for 30 minutes.
Stop the reaction with 100 µl/well of a 2N $H_2SO_4$ solution.

Reading:

450-nm reading filter
620-nm reference filter

EXAMPLE 6

Reactivity of the Synthetic Oligomannosides Versus Antibodies Produced Against Natural Oligomannosides 1) Synthetic Oligomannosides Mimicking the Antigenic Activities of the Natural Oligomannosides of Yeasts from the Genus *Candida* a) Polyclonal Antibodies

Monospecific polyclonal antibodies from Iatron were prepared by immunization of rabbits with whole yeasts then adsorbed by yeasts of heterologous species. Used as a battery, they enable identification by agglutination of the principal species of *Candida* implicated in human pathology. Each of these "factors" reacts with specific epitopes which were identified by any entire series of immunochemical studies performed in Japan. The results of these studies were summarized in the publication by S. Suzuki (Suzuki, S. et al., 1997, Curr. Top. Med. Mycol. 8: 57–70).

Figure 5:
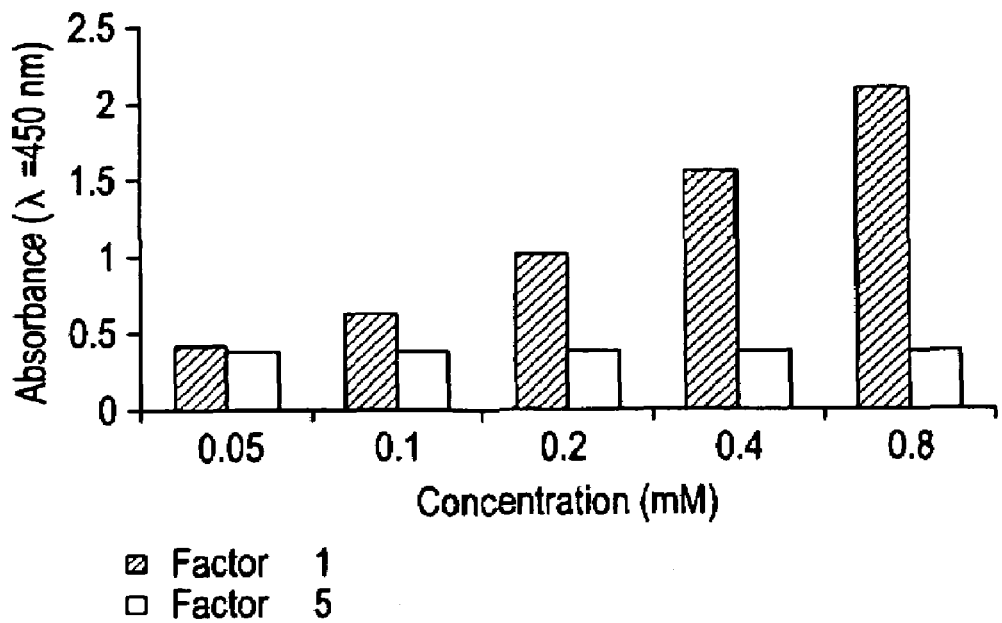
FIGS. 5 and 6 represent tests performed with D-Man α(1-2) D-Man α(1-2) D-Man α(1-2) D-Man α(1-2) and D-Man β(1-2) D-Man β(1-2) D-Man β(1-2) D-Man, respectively, on factor 5 specific of the β-1,2 oligomannosides and factor 1 reacting with the α-1,2 oligomannosides in relation to the synthetic mannotetraoses of α and β-1,2 anomery.
Figure 6:
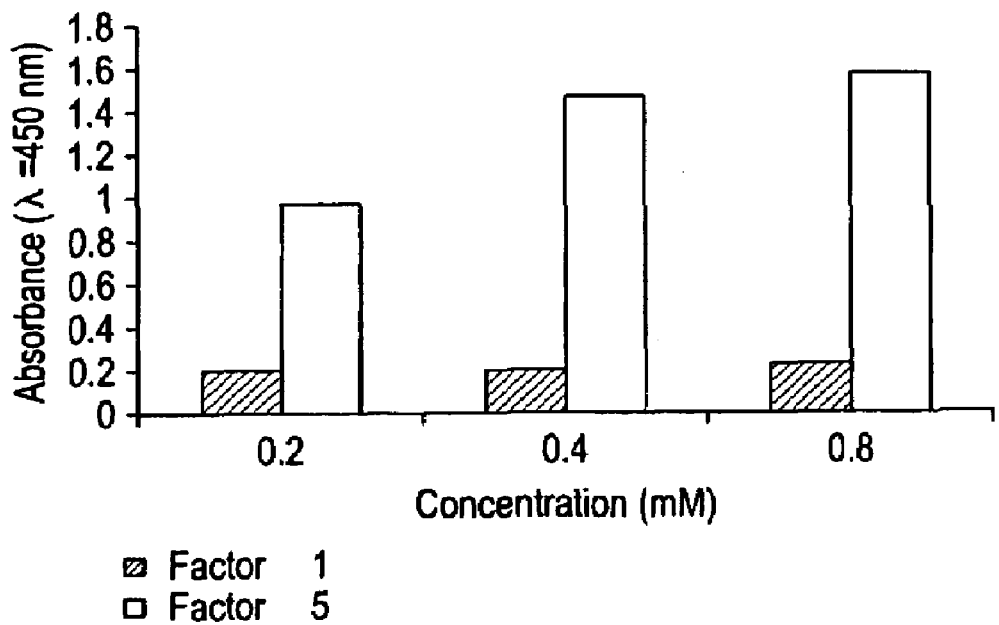

FIGS. 5 and 6 present tests performed on factor 5 (white bar), specific of the β-1,2 oligomannosides, and factor 1 (black bar), reacting with the α-1,2 oligomannosides versus the synthetic mannotetraoses of anomery α and β-1,2.

FIGS. 5 and 6 are evidence of the specificity of the reactions observed.

b) Monoclonal Antibodies

Figure 7:
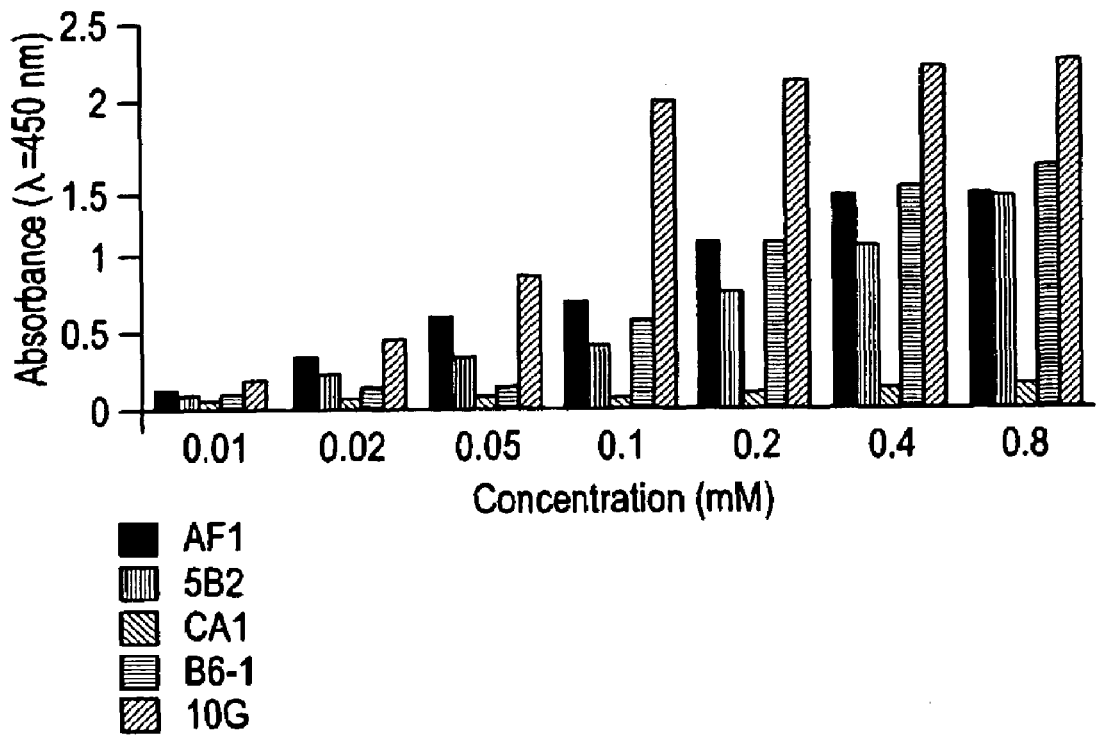
FIG. 7 shows the reactivity of D-Man β(1-2) D-Man β(1-2) D-Man β(1-2) D-Man with various monoclonal antibodies.

Various monoclonal antibodies have been described in the literature for reacting with the β-1,2 oligomannosides of *C. albicans*. FIG. 7 shows the reactivity of D-Man β(1-2) D-Man β(1-2) D-Man β(1-2) D-Man with some of these monoclonal antibodies.

Antibody 5B2 (Cailliez, J. C. et al., 1988, Ann. Inst. Pasteur Microbiol. 139: 171–88; Hopwood, V. et al. 1986, Infect. Immun. 54: 222–227; Poulain, D. et al., 1991, Mycoses 34: 221–226; Trinel, P. A., 1992, Infect. Immun. 60: 3845–3851) was generated. This antibody detects the oligomannosides circulating in the serums of animals and patients infected by *C. albicans*.

Antibody AF1 was generated by A. Cassone (De Bernardis, F. et al., 1993, J. Clin. Microbiol., 31: 3142–3146; De Bernardis, F. et al., 1994, Infect. Immun. 62: 509–519; Girmenia, C. et al., 1997, J. Clin. Microbiol. 35: 903–906; Torosantucci, A. et al., 1990, J. Gen. Microbiol. 136: 2155–2263). This antibody protects the rats in the experimental models of vaginal candidiasis.

Antibodies 1-G and B6.1 were generated by J. Cutler (Li, R. et al., 1991, J. Gen. Microbiol. 137: 455–464; Li, R. et al., 1993, J. Biol. Chem. 268: 18393–8; Kanbe, T. et al., 1994, Infect. Immun. 62: 1662–8; Han, Y. et al., 1995, Infect. Immun. 63: 2714–9; Han, Y. et al., 1997, J. Infect. Dos. 175: 1169–75; Han, Y. et al., 1997, Infect. Immun. 65: 4100–7; Han, Y. et al., 1998, Infect. Immun. 66: 5771–6; Zhang, M. X. et al., 1998, Infect. Immun. 66: 6027–9). These antibodies react against the adhesins of $C$, $albicans$ and protect the mice in the experimental models of disseminated candidiasis.

As a control, we used the monoclonal antibody CA1 produced by Sanofi-Diagnostic Pasteur which recognizes the $\alpha$a-1,2 sequences (Jacquinot, P. M. et al., 1998, FEMS Microbiol. Lett. 169: 131–8; Poulain, D. et al., 1991, Mycoses 34: 221–226; Trinel, P. A., 1992, Infect. Immun. 60: 3845–3851.

The results in FIG. 7 show that the synthetic sugars react in the anticipated manner with the monoclonal antibody and thus mimic the antigens, all of which are of great importance in physiopathology.

2) Synthetic Oligomannosides Mimicking the Antigenic Activities of the Natural Oligomannosides of Yeasts from the Genus *Saccharomyces*

It has been shown that one of the major epitopes against which was directed the ASCA response of patients with Crohn's diseases was a mannotetraose of formula Man $\alpha$-1,3 Man $\alpha$-1,2 Man $\alpha$-1,2 Man (Sendid, B. et al., 1996, Clin. Diagn. Lab. Immunol. 3: 219–26; Young, M. et al., 1998, Glycoconj. J. 15: 815–22).

a) Animal Polyclonal Antibodies

Figure 8:
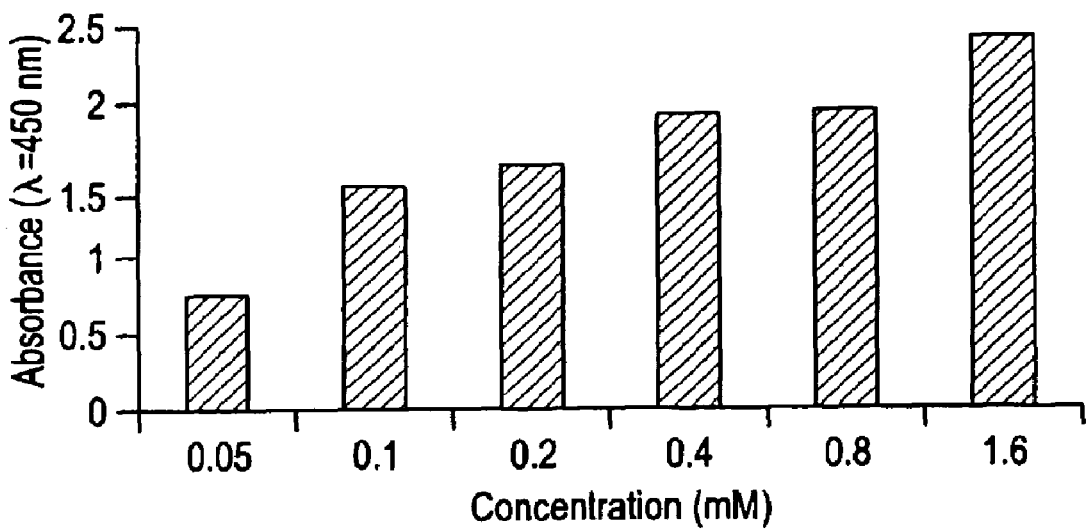
FIG. 8 shows the antigenic reactivity of synthetic mannotetraose D-Man α(1-3) D-Man α(1-2) D-Man α(1-2) D-Man in relation to antigenic factor 34.

According to the immunochemical studies performed on the Iatron serums, this structure should react with Factor 34 (Suzuki, S. et al., 1997, Curr. Top. Med. 8: 57–70). FIG. 8 shows that the results observed correspond to the anticipated results.

b) Patient Antibodies

Figure 9:
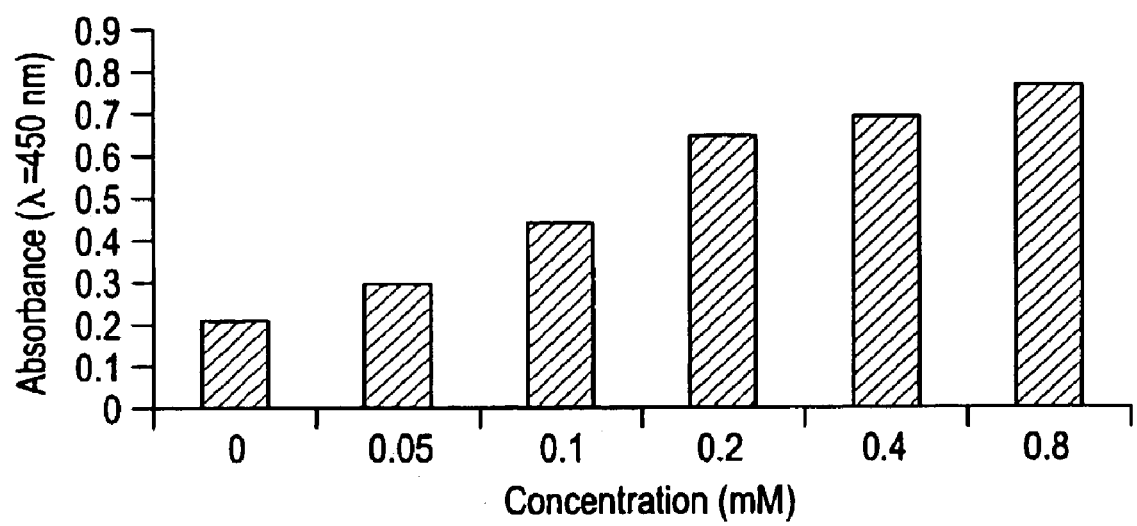
FIG. 9 shows the antigenic reactivity of a pool of serum from patients with Crohn's disease in relation to synthetic mannotetraose.

FIG. 9 shows that the use of the pool of patient serums, which serves to standardize the ASCA test, demonstrates that these antibodies affix according to a reaction dependent on the dose of synthetic antigen used for sensitizing the plates.

EXAMPLE 7

Inhibition of Colonization in an Experimental Model of Vaginal Candidiasis in the Female Rat (F. de Bernardis et al., *Infection and Immunity* 1998, 66: 3317–3325)

Ovarectomized female rats were maintained in pseudo-estrus by subcutaneous injection of 0.5 mg of estradiol benzoate every 2 days during the duration of the experiments.

The animals were inoculated with 0.1 ml of a $10^7$ yeast solution. The kinetics of the infection were monitored by determining the number of yeasts present in the vaginal secretions. 1 µl of secretion was collected with a calibrated plastic loop and spread over a dish of Sabouraud's agar plus antibiotics; the colony-forming units were counted after 48 hours of incubation at 28° C.

Figure 10:
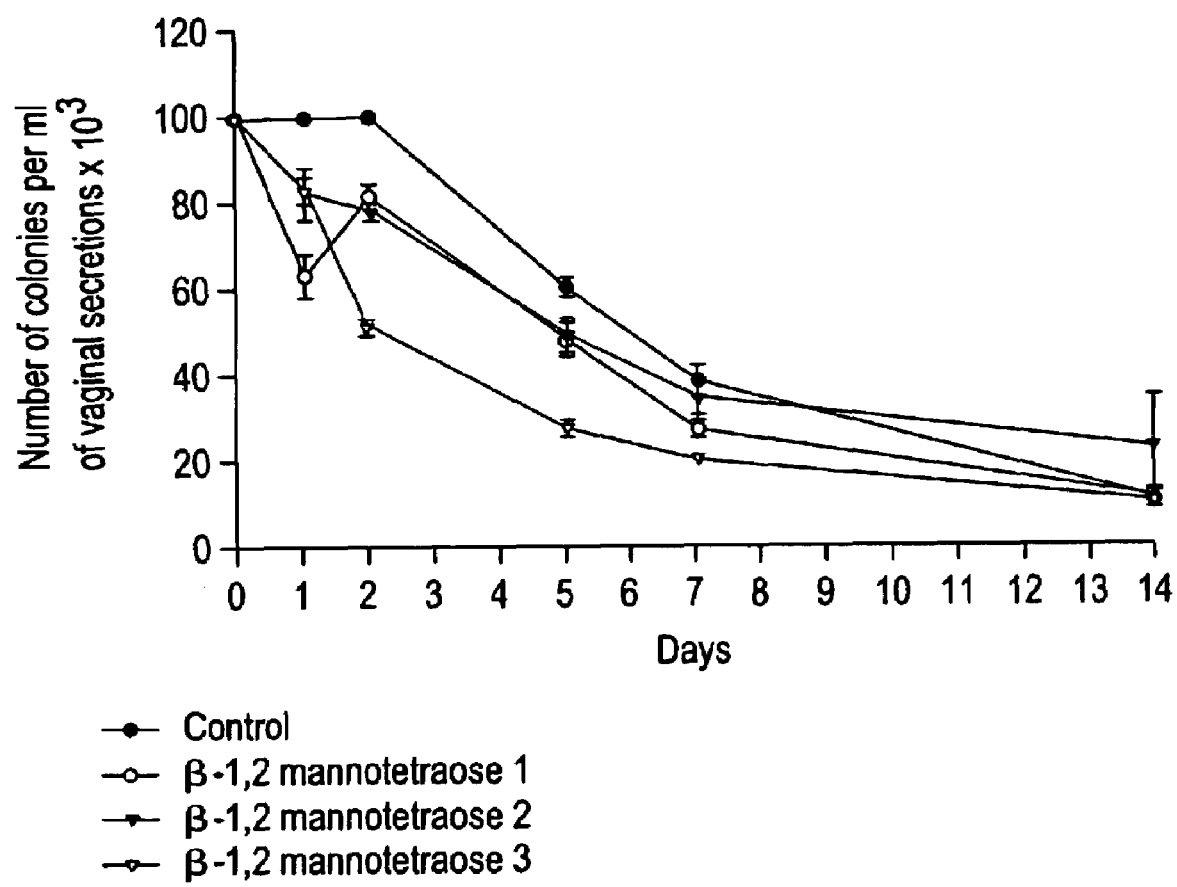
FIG. 10 shows inhibition of colonization in an experimental model of vaginal candidiasis in the rat by tetramannosides of the invention.

The graph in FIG. 10 shows the results observed in 4 series each comprising 5 rats. 1: the β-1,2 mannotetraose (100 µg) was administered 1 hour before inoculation. 2: 1 hour after inoculation. 3: 1 h, 24 h and 48 h after inoculation.

EXAMPLE 8

Inhibition of Intestinal Colonization by *C. albicans* by Synthetic β-1,2 Oligomannosides The increasing incidence of systemic candidiasis is a major medical and economic problem in the hospital environment. This form of candidiasis is principally caused by yeasts whose natural habitat is the human gastrointestinal tract. It is estimated that 40 to 80% of individuals are carriers of *C. albicans* or of *C. glabrata*, the two most pathogenic species of the genus. Systemic candidiasis is generally caused by the species harbored by the patient and which is disseminated. In intensive-care and clinical hematology patients, colonization has been established as an independent risk factor of the development of systemic candidiasis. The nature of the ligand-receptor systems responsible for intestinal colonization by *C. albicans* is unknown.

We have found that the particular sugars of the wall surface of *C. albicans*, the β-1,2 oligomannosides, affix to the macrophage cells by the intermediary of galectin-3. The β-1,2 oligomannosides are massively expressed at the wall surface associated with various types of molecules, mannans, the mannoproteins and a glycolipid, PLM. Galectin-3 is especially known as a lectin expressed on polarized epithelial cells. These results allow us to assume that galectin-3 is likely responsible for fixation of *C. albicans* on the intestine via the β-1,2 oligomannosides.

We simultaneously indirectly established that the β-1,2 oligomannosides apparently had a role in the pathogenesis of candidiasis. The specific antibodies to these residues are protective in contrast to the antibodies directed against the α-bond mannose residues, which are much more ubiquitous. The mechanisms responsible for the protection have not been clarified. There have been no studies to date analyzing the correlations between surface phenotypic expression of β-1,2 oligomannosides and pathogenicity of the strains of *C. albicans*. However, these older studies using anti-glycoprotein monoclonal antibody of *C. albicans* had shown that this antibody reacts to a greater extent with strains isolated in a pathogenic position than with those strains isolated in a saprophyte position. It was subsequently shown that this antibody reacts specifically with the β-1,2 oligomannoside epitopes.

On these bases, the experimental model which was developed to explore the role of the β-1,2 oligomannosides in intestinal colonization attempted first to implicate the strains of *C. albicans* selected for present different levels of phenotypic expression of β-1,2 oligomannosides and then to explore the effect of the administration of β-1,2 oligomannosides on intestinal colonization.

The strains were selected on the basis of studies which demonstrated reproducible differences in pathogenicity among strains of *C. albicans* in two experimental models of systemic infection in the rat and the mouse. The co-agglutination of yeasts with latex particles sensitized by various anti-β-1,2 oligomannoside monoclonal antibodies made it possible to demonstrate that the most virulent strains expressed more β-1,2 oligomannosides at their surface. The model of intestinal colonization used with that of the neonatal mouse developed by Cole et al.

Two strains were implicated: one "virulent", expressing more surface β-1,2 oligomannosides that an "avirulent" strain. On the basis of stool examinations, the virulent strain was shown to be capable of maintaining a more intense and more persistent gastrointestinal colonization than the strain expressing less β-1,2 oligomannosides. It was then attempted to inhibit this intense colonization. For this purpose, β-1,2 oligomannosides obtained by chemical synthesis according to the invention were administered to the mice prior to inoculation of the strain. This procedure provided large quantities of pure products while eliminating the requirement for lengthy procedures for the purification of biological materials.

Administration of synthetic β-1,2 tetramannosides prophylactically yielded a drastic, dose-dependent reduction in the number of yeasts found in the stools in relation to the untreated animals and those treated by synthetic α-1,2 tetramannosides used as a control. These results reinforce the information acquired on the physiopathological importance of the β-1,2 oligomannosides presented specifically by *C. albicans* to the cells and endogenous lectins of its natural hosts. The results also open up opportunities for the development of prophylactic measures based on analogues of natural products of *C. albicans* and capable of decontaminating the gastrointestinal tract of patients at risk.

I-Material and Methods

1) Strains of *C. albicans*

We used 7 strains of *C. albicans* of serotype A for which it had been possible in earlier experiments to demonstrate pathogenicity differences in models of systemic candidiasis in the rat and the mouse [Schmidt, 1996 #2553]. This involved 3 avirulent strains ATCC 44831, ATCC 18804 and ATCC 10231, 3 virulent strains ATCC 44505, ATCC 62342 and ATCC 10261, and one strain of intermediary virulence: ATCC 32354.

2) Agglutination by Latex Particles Sensitized by Anti-β-1,2 Oligomannoside Monoclonal Antibodies.

Two monoclonal antibodies were used to sensitize the latex particles: monoclonal antibody AF1, provided by Professor A. Cassone (Cassone, 1988 #3333) and monoclonal antibody DF9-3, provided by Dr. M. Borg-von-Zepelin (Borg-von-Zepelin, 1993 #283). These monoclonal antibodies were specific to β-1,2 oligomannoside epitopes. They react specifically, on the one hand, with the β-1,2 oligomannosides derived from the mannans converted into neoglycolipids and used for sensitizing the microtitration plates and, on the other hand, with the PLM of *C. albicans* which only expresses this type of epitope (Trinel, 1992 #3603; Trinel, 1993 #3292; Trinel, 1999 #3692).

The latex particles, sensitized according to the previously described method, were of the Bichro-latex® type. They are colored and suspended in a buffer of complementary color to facilitate reading containing a solution which inhibits spontaneous agglutination of the yeasts [Quindos, 1997 #3321]. When performing the test, 15 μml of a suspension of $10^6$ yeasts per ml (McFarland scale) obtained after 48 h of culture at 24° C. on Sabouraud's agar was brought into the presence of 15 μl of Bichro-latex and agitated on a Kline agitator. The agglutination scores were assessed with the naked eye after 1 min, 2 min and 3 min of agitation according to a scale of 0.5 to 2, and cumulated. This method has proven to have excellent reproducibility. The agglutinations were performed on a blind basis on strains provided by Schmidt with arbitrary numbers; the results were decrypted afterward.

3) Animals

The mothers and their litters (10 to 15 baby mice/litter) were received on the $4^{th}$ day of life (line CD-1® (Crl: CD-1® (ICR) BR, Charles River, Saint Aubin les Elbeuf, France). The animals were inoculated on the $6^{th}$ day of life. There was always a separation from the mother for 3 hours prior to gavage and a one hour interval after inoculation.

4) Strains

Two strains of *C. albicans* were used, strain 4276 which expresses a small amount of β-1,2 oligomannosides at its surface and strain 4277 which expresses a large amount. Prior to each use, the strains were re-inoculated on Sabouraud-chloramphenicol (SC) agar from a culture stored at −80° C. in PBS-40% glycerol. After incubation for 24 hours at 35° C., the yeasts were washed 3 time in sterile physiological water (NaCl 0.9%, water φ) and the suspension was adjusted to $2 \times 10^9$/ml. The viability of the inoculum was verified for each experiment by sowing suitable dilutions of the yeast suspensions on SC agar in Petri dishes.

5) Treatment with the Synthetic Sugars

For certain experiments, the synthetic sugars (β-1,2 oligomannosides (βMan) and α-1,2 oligomannosides (αMan) were administered by gavage 1 hour after the inoculation. The sugars were diluted in sterile water to obtain the desired concentration (see results) in a volume of 50 μl. Two independent experiments were carried out. In the first, 4 litters infected with strain 4277 were compared after administration, respectively, of water (litter 1), of 50 μg pf αMan (litter 2), 150 μg of βMan (litter 3) or 150 μg of 0αMan (litter 4). In the second experiment, four litters were infected either with strain 4276 (litters 1 and 2) or with strain 4277 (litters 3 and 4) after treatment with water (litters 1 and 3) or 50 μg of bMan (litters 2 and 4).

6) Monitoring the Infection

Mortality: the cages were monitored once daily and the number of mice was recorded.

Gastrointestinal colonization: sequentially, beginning on day 7 after the inoculation, one dropping was collected from each mouse, ground in 100 μl of sterile water with a small piston adapted to function in 1.5-ml Eppendorf tubes and the total volume was inoculated on SC agar in a Petri dish. The number of colony forming units (CFU) was counted after 24 hours of incubation at 30° C. When the CFU density prevented counting, a score was attributed on the basis of the appearance of the culture so as to allow statistical comparisons: 2 or 1000 CFU, 3 or 10,000 CFU, 4 or 100,000 CFU.

7) Statistical Analysis

The gastrointestinal colonizations according to the infecting strain and according to the treatment preceding the inoculation were compared using a nonparametric test (Mann-Whitney or Kruskall-Wallis test, depending on the number of groups) using the program Statview 4.5 for Macintosh. The percentages of positive cultures or deaths on day 1 were compared with the Fisher exact test.

II-Results

1) Surface Expression of β-1,2 Oligomannosides According to the Virulence of Serotype A Strains of *C. albicans*

The agglutination scores observed on the 7 serotype A strains by Bichro-latex particles sensitized by one of the anti-β-1,2 oligomannoside monoclonal antibodies are presented in Table 1 in relation to their virulence observed in the experimental models of systemic candidiasis. All of the avirulent strains presented an agglutination score lower than that of the virulent strains or of the strain of intermediate virulence.

Table 1 below presents the agglutination scores using Bichro-latex particles sensitized by antibodies DF9-3 and AF1 in relation to the virulence of the strains of *C. albicans*.

TABLE 1

| Strains | DF9-3 | | | | AF1 | | | | Total | Status |
| --- | --- | --- | --- | --- | --- | --- | --- | --- | --- | --- |
| | 1 min | 2 min | 3 min | cum. | 1 min | 2 min | 3 min | cum. | | |
| ATCC 44505 | 1 | 1.5 | 1.5 | 4 | 0.5 | 1 | 1 | 2.5 | 6.5 | virulent |
| ATCC 44831 | 0.5 | 1 | 1 | 2.5 | 1 | 1 | 1 | 3 | 5.5 | avirulent |
| ATCC 62342 | 1 | 1.5 | 2 | 4.5 | 1 | 1.5 | 1.5 | 4 | 8.5 | virulent |
| ATCC 32354 | 1 | 1.5 | 2 | 4.5 | 0.5 | 1 | 1 | 2.5 | 7 | intermediate |
| ATCC 18804 | 1 | 1 | 1 | 3 | 0.5 | 1 | 1 | 2.5 | 5.5 | avirulent |
| ATCC 10261 | 1 | 1.5 | 2 | 4.5 | 1 | 1.5 | 2 | 4.5 | 9 | virulent |
| ATCC 10231 | 1 | 1 | 1.5 | 3.5 | 0.5 | 0.5 | 1 | 2 | 5.5 | avirulent |

2) Differences in Mortality and Gastrointestinal Colonization Observed According to the Inoculation of the Mouse with a Virulent Strain Expressing More β-1,2 Oligomannosides than a Nonvirulent Strain a) Mortality By cumulating the data obtained in the 3 independent experiments, the early mortality (day 1) after inoculation of strain 10261 was higher than that observed after inoculation of strain 10231 (3/63 versus 1/62, p=0.059 Fisher exact test).

b) Gastrointestinal Colonization

The number of CFUs present was significantly higher when the baby mice were inoculated with strain 4277 than when they were inoculated with strain 4276. This finding was true during the entire monitoring period (Table 1). Moreover, the colonization lasted significantly longer (at day 33 after infection, 11/11 mice infected with strain 10261 still had infected droppings versus only 5/11 mice for those inoculated with strain 10231, p=0.006 Fisher exact test).

Figure 11:
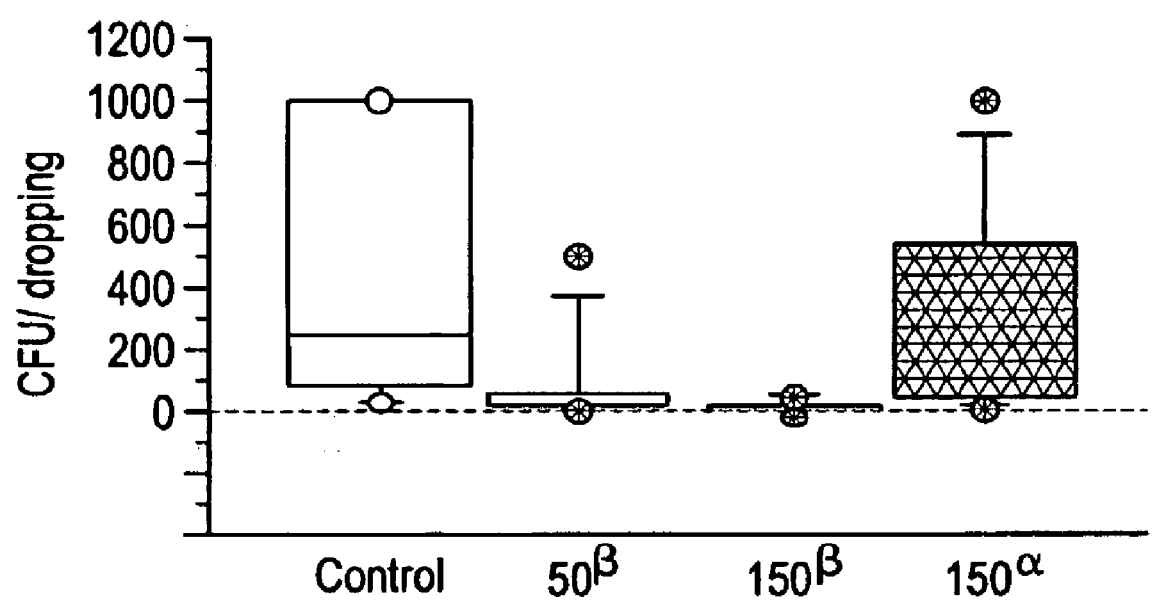
FIG. 11 is a comparison of gastrointestinal colonization by strain 10261 in relation to the prior administration of synthetic sugar. The gastrointestinal colonization was evaluated 7 days after the inoculation by measuring the CFU/dropping for young mice having received water (control), 50 μg (50β) or 150 μg (150β) of βMan or 150 μg of αMan (150α).

3) Prophylactic Effect of Synthetic Tetramannosides of α- or β-1,2 Anomery on Gastrointestinal Colonization Administration of synthetic tetramannosides prior to inoculation of the pathogenic strain 4277 led to different results depending on the anomery of the bond of the sugars used. The results are presented in Table 2 and FIG. 11.

Table 2 below presents the gastrointestinal tract kinetics in relation to the infectious strain.

was increased (median of CFUs=48.5 for 50 μg, p<0.02 vs. control and 5 for 150 μg, p<0.0001 vs. control) (FIG. 1).

III. Discussion

Gastrointestinal colonization is recognized as a difficult to control source of systemic candidiasis infection in hospitalized patients. Despite the biological and medical importance of the natural colonization of humans by *C. albicans*, its detailed molecular mechanisms remain unknown. The recent, unexpected discovery that galectin-3 is an endogenous human lectin functioning as a specific receptor for the β-1,2 oligomannosides has opened up new perspectives in this field because galectin-3 is a lectin that is primarily expressed on the enterocyte. At the same time, although the β-1,2 oligomannosides appear increasingly likely to be molecules implicated in the pathogenesis of candidiasis, there have been no studies regarding the analysis of their phenotypic expression in relation to the pathogenicity of the strains.

We have found that the differences in virulence observed between the strains of *C. albicans* in models of systemic candidiasis are linked at the level of surface expression of β-1,2 oligomannosides. Subsequently, newborn mice were inoculated orally with identical quantities of yeasts stemming from two strains of different virulence and level of expression of oligomannosides. The virulent strain express-

TABLE 2

| | CFU/dropping on average ± standard deviation (n) | | P |
| --- | --- | --- | --- |
| Day after infection | ATCC 10231 | ATCC 10261 | (Mann-Whitney) |
| Day 12 | 154 ± 143 (n = 19) | 609 ± 340 (n = 18) | <0.0001 |
| Day 15 | 393 ± 419 (n = 12) | 5777 ± 4316 (n = 11) | 0.0003 |
| Day 19 | 58 ± 62 (n = 11) | 795 ± 354 (n = 11) | <0.0001 |
| Day 26 | 94 ± 285 (n = 11) | 581 ± 416 (n = 11) | 0.0006 |
| Day 33 | 2 ± 3 (n = 11) | 1515 ± 3008 (n = 11) | <0.0001 |

Administration of αMan prior to inoculation with strain 10261 did not modify the degree of gastrointestinal colonization (median of CFUs=258 vs 196) whereas administration of βMan significantly decreased the degree of colonization, with the results increasing in intensity as the dose ing larger amounts of β-1,2 oligomannosides led to a higher mortality of the baby mice as well as a more intense and persistent colonization. These results suggest that virulence and/or the amount of β-1,2 oligomannosides present at the surface of the cells of the strains of yeast are linked to their ability to cause the death of the mice and to colonize them in a more intense and long-lasting manner.

In order to verify the hypothesis of the role of β-1,2 oligomannosides in the intestinal colonization, these residues were administered in a prophylactic manner prior to inoculation of the more virulent strain. Gavage of the mice with μ-1,2 oligomannosides prior to inoculation with *C. albicans* led to a dose-dependent reduction in colonization. The almost total reduction observed with a dose of 150 μg of β-1,2 tetramannosides was not seen when an α-1,2 tetramannoside was administered under the same conditions, thereby demonstrating the specific role of the β-1,2 oligomannosides in the intestinal colonization by *C. albicans*.

These results allow for prophylactic measures intended to decolonize the gastrointestinal tract of patients at risk of developing systemic candidiasis during their hospitalization. These are patients who are to be subjected to intensive chemotherapy protocols, marrow and organ transplants, gastrointestinal surgery patients and intensive-care patients who can be fed enterally.

More recently, there have been several orders of prophylactic methods targeting gastrointestinal decolonization. The oral administration of amphotericin B, which does not cross the gastrointestinal barrier, did not yield convincing results. More recently, the administration of anti-*C. albicans* immunoglobulins was also proposed without the nature of the epitopes being known nor the true efficacy of this procedure. Administration of *S. boulardii* (*S. cerevisiae*) corresponds to procedures that have been known for a long time regarding the use of probiotics capable of entering into competition with *C. albicans* in the intestinal ecology niche. The data on its efficacy are contradictory and several cases of septicemia caused by *S. boulardii*—albeit rare in relation to the number of patients treated—threaten to cast doubts on this prophylaxis.

The use of yeast molecules having a role in adhesion such as the β-1,2 oligomannosides falls within the framework of prebiotic treatment. These β-1,2 oligomannosides are molecules which, along with the yeasts that express them naturally at their surface, are normally present in the intestine and are thus normally tolerated by the organism. Until the present, the studies on the biological role of these residues have been prepared using material prepared biochemically from yeasts according to procedures which are time-consuming and difficult to standardize, accompanied by all of the risks inherent in the preparation, i.e., the contamination of biological materials.

One of the original features of this invention is found in its use of synthetic sugars with a structure that is perfectly analogous to that of the *C. albicans* sugars. The procedure employed for this synthesis can easily be transposed for the production of large amounts. Numerous questions remain regarding the detailed mechanisms of the inhibition of *C. albicans* colonization by synthetic β-1,2 oligomannosides as well as the optimization of the doses of the chemical constructions. Nevertheless, this invention reinforces on the biological level the information acquired on the physiopathological importance of the β-1,2 oligomannosides presented specifically by *C. albicans* to the cells and endogenous lectins of its natural hosts. It also allows us to envisage innovative prophylactic measures based on analogues of natural products of *C. albicans* and intended to decontaminate the gastrointestinal tract of patients at risk.

This strategy in combination with others already in progress could help resolve a major infectious problem linked to the natural presence in the gastrointestinal tracts of hospitalized patients of an opportunistic agent whose infectious capacities increase in parallel with the progress of the medical and surgical techniques affecting the homeostasis of the patients.

EXAMPLE 9

Therapeutic Effects of Synthetic β-1,2 Oligomannosides on Vaginal Candidiasis

Vaginal candidiasis is an opportunistic infection caused principally by *C. albicans*, a yeast which is generally inoffensive. Its natural habitat is the human gastrointestinal tract (about 50% of individuals) as well as the vagina in about 10% of women. The yeasts multiply in the vagina without any pathological manifestations. Their presence is, however, dependent on the physiological state of the woman. Thus, during pregnancy, the percentage of women whose vagina is colonized by *C. albicans* increases to reach 30%.

In addition to these relations of simply being a surface carrier, *C. albicans* can invade the vaginal sphere and cause very bothersome infections with itching, burning sensations and vaginal discharges. The causes of these invasions have not been elucidated. Their mechanism and the symptoms of the infections are very certainly increased by the defense reactions.

It is known at present that 75% of all women will suffer at least one episode of vaginal candidiasis at least once in their life. More than 20% of these women experience recurrences which are difficult to treat despite antifungal agents which are theoretically very effective. These recurrences have a physical and psychological impact on an unknown percentage of women. Although this is not a sexually transmissible disease in the true sense of the term, it disturbs the lives of millions of women and couples.

We studied the mechanisms brought into play during the transformation of the yeast from its inoffensive saprophyte form to its pathogenic form. The principal biological properties of *C. albicans* implicated in its pathogenesis are those that allow it to adhere to the cells of the host, to penetrate tissues and to avoid the defensive reactions.

On the basis of the analysis of the variations of *C. albicans* in relation to its pathogenicity, we were able to identify the molecules by means of which *C. albicans* adheres to the cells and which are capable of modulating the immune response. These molecules have as a common point the expression of sugars particular to certain species of *Candida* and more particularly to *C. albicans*: the β-1,2 oligomannosides.

Various studies using these purified sugars from *C. albicans* have shown that they affix to human cells and that this fixation via a specific receptor leads to a response of the target cell.

The importance of the β-1,2 oligomannosides in the pathogenesis of candidiasis, on the one hand, and the difficulties inherent in obtaining them in large amounts from the yeast, on the other hand, led us to prepare and use the homologues obtained by chemical synthesis according to the invention.

Research investigations have demonstrated that the presence of β-1,2 oligomannosides in vaginal secretions is an excellent marker of the pathogenic behavior of C. albicans.

Thus, it has been shown that the anti-mannan antibodies and a monoclonal antibody named AF1 recognize the β-1,2 oligomannosides protecting the rat against vaginal candidiasis.

These results allow us to conclude that the production of β-1,2 oligomannosides by *Candida albicans* is an important element in the pathogenesis process of candidiasis. It was, therefore, taken into consideration that the administration of synthetic β-1,2 oligomannosides (as decoys) could saturate the ligands of the vaginal cells with which *C. albicans* interacts and thereby deprive the yeast of specific interaction sites.

We used a model of vaginal candidiasis recognized by the international community and with which the most pertinent animal experiments to date have been performed.

The results obtained in two experimental series were in perfect agreement. They showed a dose-dependent relation of inhibition of colonization/infection by administration of synthetic β-1,2 oligomannosides 1 h, 24 h and 48 h after inoculation. Even at the maximum dose, the α-1,2 oligomannosides administered in the same manner as control has no effect as shown in Table 3 below. Thus, the animals receiving the β-1,2 oligomannosides exhibited a level of colonization that decreased by close to half beginning on the first day of administration and were the only animals to no longer be carriers of *C. albicans* at the end of the experiments.

TABLE 3

| Days | SA-40 Control | SA-40 +βM 4 (150 γ) | SA-40 +βM 4 (100 γ) | SA-40 +βM 4 (50 γ) | SA-40 +αM A N (100 γ) | SA-40 +αM A N (50 γ) |
|---|---|---|---|---|---|---|
| 0 | >100 | >100 | >100 | >100 | >100 | >100 |
| 1 | >100 | 62 ± 7 | 87 ± 6 | >100 | >100 | >100 |
| 2 | >100 | 54 ± 0 | 83 ± 8 | 88 ± 6 | 93 ± 3 | 95 ± 2 |
| 5 | 89 ± 3 | 27 ± 3 | 40 ± 6 | 62 ± 4 | 83 ± 5 | 86 ± 4 |
| 7 | 67 ± 5 | 28 ± 4 | 54 ± 8 | 57 ± 3 | 71 ± 6 | 69 ± 6 |
| 14 | 49 ± 9 | 5.6 ± 3 | 45 ± 14 | 23 ± 5 | 495 | 48 ± 4 |
| 21 | 20.8 ± 1.7 | <1 | <1 | <1 | 22.4 ± 3.4 | 21 ± 4 |

It thus appears possible to inhibit infection by *C. albicans* with inoffensive sugars, completely analogous to the natural sugars, for example, contained in gynecological ovules. The implications of these results are important on the medical and levels, for example, as an adjuvant to conventional antifungal treatments.

The invention claimed is:

1. A process for preparing a synthetic oligomannoside, wherein at least one functional group of the synthetic oligomannoside is a connector comprising a carboxylic acid functional group or a $C_1$ to $C_{10}$ alkyl, the synthetic oligomannoside being devoid of cellular components and homologous to a wall oligomannoside of an infectious organism or pathogen, from monosaccharides or disaccharides by condensation of protected dimannosides comprising:

a) preparing diblocks in which:
at least one of two blocks is the intermediary block in which free hydroxyl functional groups of the monosaccharides are protected by one or more, identical or different protector groups, except for a hydroxyl functional group necessary for condensation with another diblock which is activated by a starting group, and one of the two blocks is a terminal block in which free hydroxyl functional groups of the monosaccharides are protected by one or more, identical or different protector groups, except for a hydroxyl functional group necessary for condensation with another diblock, and optionally a hydroxyl functional group protected by a binding group for attachment of the oligomannoside on a support, b) condensing said diblocks, and c) deprotecting resulting oligomannoside.

2. The process according to claim 1, wherein in step (a), at least one Man α(1-2) Man dimannoside of formula (IV):

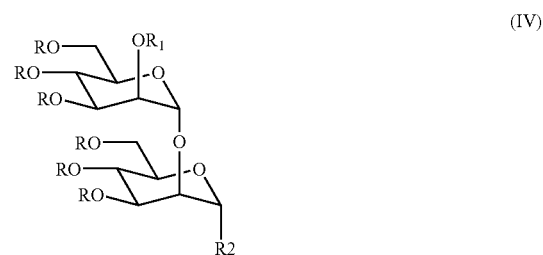

wherein:

R is a permanent protector group,

R1 is a temporary protector group,

R2 is:
in the case of an intermediary block, a starting group associated with the polymer at α or β;
in the case of a terminal block, a group selected from an alkyl group, a benzyl group, or a connector comprising a carboxylic acid functional group or a $C_1$ to $C_{20}$ alkyl at α or β, is prepared.

3. The process according to claim 1, wherein in step (a), at least one Manβ(1-2) Man dimannoside of formula (V):

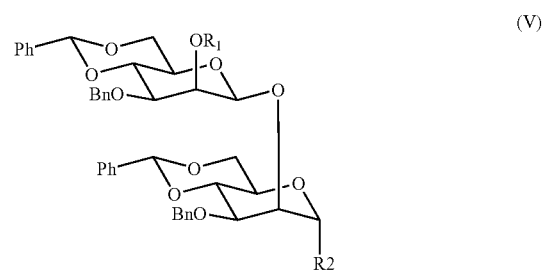

wherein:

R1 is a temporary protector group,

R2 is:
in the case of an intermediary block, a starting group associated with the polymer at α or β;
in the case of a terminal block, a group selected from among an alkyl group, a benzyl group, or a connector comprising a carboxylic acid functional group or a $C_1$ to $C_{20}$ alkyl at α or β, is prepared.

4. The process according to claim 1, wherein in step (a), at least one Man α(1-3) Man dimannoside of formula (VI):

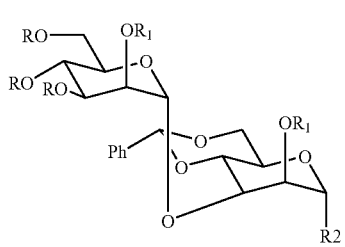

(VI)

wherein:
R is a permanent protector group,
R1 is a temporary protector group,
R2 is:
  in the case of an intermediary block, a starting group associated with the polymer at α;
  in the case of a terminal block, a group selected from among an alkyl group, a benzyl group, or a connector comprising a carboxylic acid functional group or a $C_1$ to $C_{20}$ alkyl at α or β, is prepared.

5. A process for preparing a tetramannoside D-Man β(1-2) D-Man β(1-2) D-Man β(1-2) D-Man of formula (I):

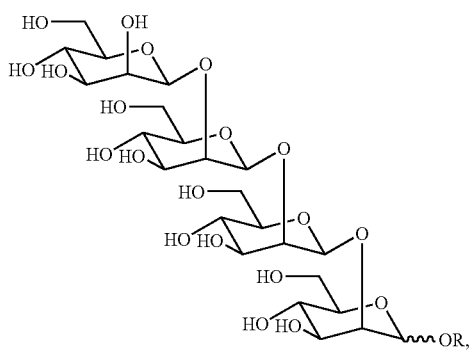

(I)

wherein R represents a hydrogen atom, a $C_1$ to $C_{20}$ alkyl, an optionally labeled connector group comprising a carboxylic acid functional group or a $C_1$ to $C_{20}$ alkyl, comprising condensing two Man β(1-2) blocks of formula (V):

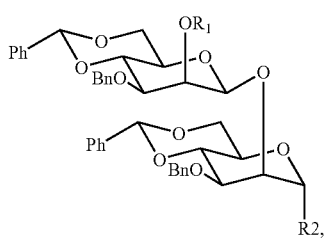

(V)

one of which is an intermediary diblock in which R1 is a temporary protector group, and R2 is a starting group, forming a β bond, and the other of which is a terminal diblock in which R2 is an —SPh group.

6. A process for preparing a tetramannoside D-Man α(1-2) D-Man α(1-2) D-Man α(1-2) D-Man of formula (II):

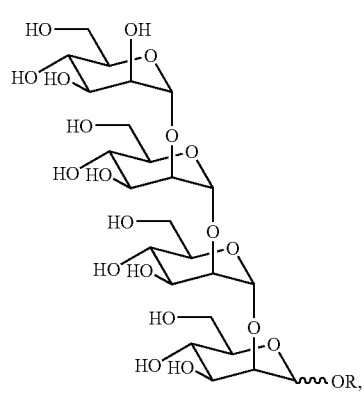

(II)

wherein R represents a hydrogen atom, a $C_1$ to $C_{20}$ alkyl, an optionally labeled connector group comprising a carboxylic acid functional group or a $C_1$ to $C_{20}$ alkyl, comprising condensing two Man α(1-2) Man blocks of formula (IV):

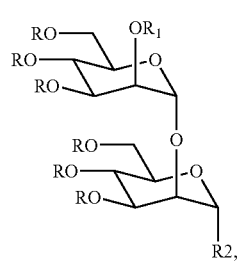

(IV)

one of which is an intermediary diblock in which R is a permanent protector group, R1 is a temporary protector group, and R2 is a starting group, and the other is a terminal diblock in which R2 is an —SPh group.

7. A process for preparing a tetramannoside D-Man α(1-3) D-Man α(1-2) D-Man α(1-2) D-Man α(1-2) of formula (III):

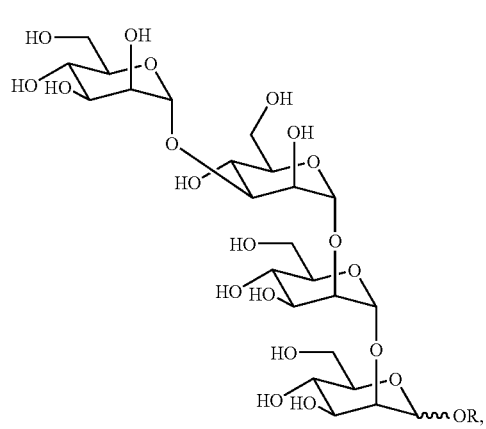

(III)

wherein R represents a hydrogen atom, a $C_1$ to $C_{20}$ alkyl, an optionally labeled connector group comprising a carboxylic acid functional group or a $C_1$ to $C_{20}$ alkyl, comprising condensing a Man α(1-3) diblock of formula (VI):

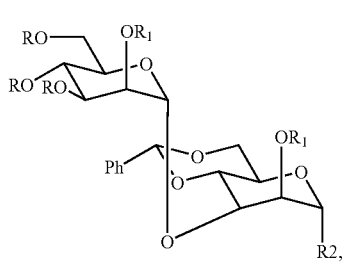

(VI)

and α Man α(1-2) Man diblock of formula (IV):

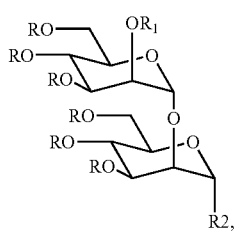

(IV)

with the intermediary diblock being Man α(1-3) Man of formula (VI) in which R is a permanent protector group, R1 is a temporary protector group R2 is a starting group, and the terminal diblock is Man α(1-2) Man in which R2 represents the R group defined in formula (III).

8. A process for in vitro detecting presence of an infection by an infectious organism or pathogen whose membrane contains oligomannosides comprising:

contacting a pharmaceutical composition comprising a therapeutically effective amount of at least one synthetic oligomannoside produced by chemical synthesis, the synthetic oligomannoside being devoid of cellular components and homologous to a wall oligomannoside of an infectious organism or pathogen, and a pharmaceutically acceptable vehicle, the pharmaceutical composition affixed to a solid support, with a biological sample capable of containing antibodies directed against the infectious organism or pathogen, and detecting formation of an antigen-antibody complex.

9. The process according to claim 8, wherein the composition comprises at least one of D-Man β(1-2) D-Man β(1-2) D-Man β(1-2) D-Man of formula (I)

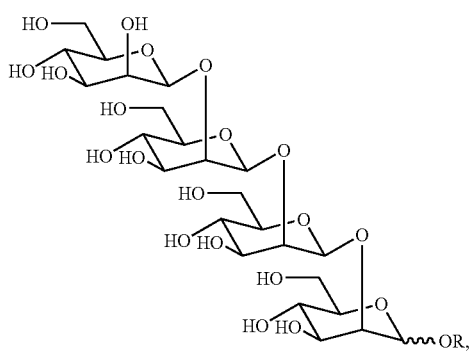

(I)

and D-Man α(1-2) D-Man α(1-2) D-Man α(1-2) D-Man of formula (II)

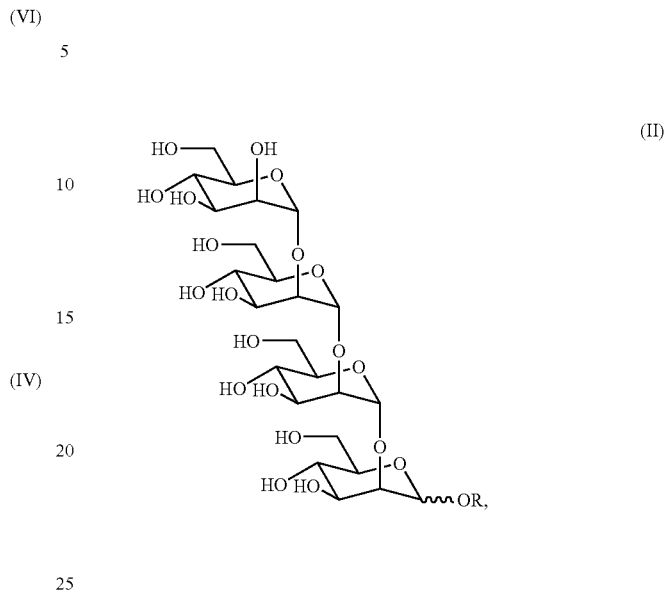

(II)

wherein R represents a connector comprising a carboxylic acid functional group or a $C_1$ to $C_{20}$ alkyl.

10. The process according to claim 8, wherein the infectious organism is *C. albicans*.

11. The process according to claim 8, wherein the composition comprises D-Man α(1-3) D-Man α(1-2) D-Man α(1-2) D-Man α(1-2) of formula (III)

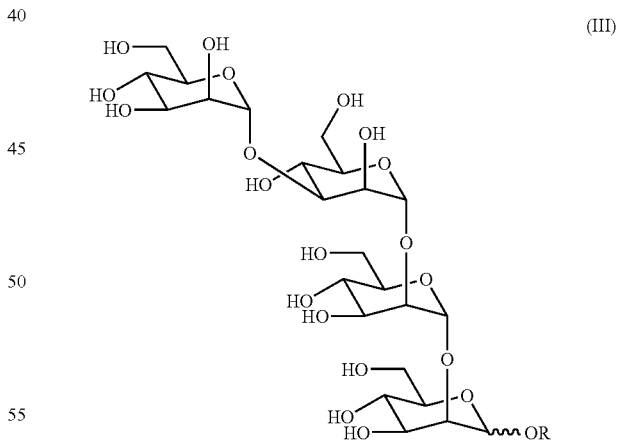

(III)

wherein R represents a connector comprising a carboxylic acid functional group or a $C_1$ to $C_{20}$ alkyl.

12. The process according to claim 8, wherein the infectious organism is *S. Cerevisiae*.

* * * * *

UNITED STATES PATENT AND TRADEMARK OFFICE
CERTIFICATE OF CORRECTION

| | | |
|---|---|---|
| PATENT NO. | : 7,109,182 B2 | Page 1 of 1 |
| APPLICATION NO. | : 10/153936 | |
| DATED | : September 19, 2006 | |
| INVENTOR(S) | : Jacques Esnault et al. | |

It is certified that error appears in the above-identified patent and that said Letters Patent is hereby corrected as shown below:

<u>In column 49</u>
at line 58, after "functional group or a", please change "$C_1$ to $C_{10}$" to read
-- $C_1$ to $C_{20}$ --.

Signed and Sealed this

Twenty-seventh Day of February, 2007

JON W. DUDAS
*Director of the United States Patent and Trademark Office*